(12) United States Patent  
Hamamoto et al.

(10) Patent No.: US 8,993,592 B2  
(45) Date of Patent: Mar. 31, 2015

(54) CYCLIC AMINE COMPOUND AND ACARICIDE

(75) Inventors: Isami Hamamoto, Odawara (JP); Keiji Koizumi, Odawara (JP); Makio Yano, Nagareyama (JP); Masahiro Kawaguchi, Odawara (JP); Hazumi Nomura, Odawara (JP); Tetsuya Haruyama, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 149 days.

(21) Appl. No.: 13/261,330

(22) PCT Filed: Dec. 17, 2010

(86) PCT No.: PCT/JP2010/072766  
§ 371 (c)(1),  
(2), (4) Date: Jun. 18, 2012

(87) PCT Pub. No.: WO2011/078081  
PCT Pub. Date: Jun. 30, 2011

(65) Prior Publication Data  
US 2012/0289700 A1   Nov. 15, 2012

(30) Foreign Application Priority Data

Dec. 21, 2009 (JP) ................... 2009-289576  
Feb. 25, 2010 (JP) ................... 2010-039839  
May 21, 2010 (JP) ................... 2010-117392

(51) Int. Cl.
| | |
|---|---|
| *C07D 451/06* | (2006.01) |
| *A01N 43/90* | (2006.01) |
| *A01N 43/58* | (2006.01) |
| *A01N 43/40* | (2006.01) |
| *A01N 43/42* | (2006.01) |
| *A01N 43/56* | (2006.01) |

(Continued)

(52) U.S. Cl.  
CPC ............... *A01N 43/58* (2013.01); *A01N 43/40* (2013.01); *A01N 43/42* (2013.01); *A01N 43/56* (2013.01); *C07D 401/12* (2013.01); *C07D 401/14* (2013.01); *C07D 405/14* (2013.01); *C07D 409/14* (2013.01); *C07D 451/06* (2013.01); *A01N 43/90* (2013.01)  
USPC ........... 514/304; 546/124; 546/193; 546/194; 544/333

(58) Field of Classification Search  
USPC ............ 514/304; 546/124, 193, 194; 544/333  
See application file for complete search history.

(56) References Cited

U.S. PATENT DOCUMENTS 2,970,144 A  1/1961  Zirkle  
4,808,645 A  2/1989  Ravichandran et al.

(Continued)

FOREIGN PATENT DOCUMENTS

EP  0 200 683 B1  4/1990  
EP  0 456 519 B1  7/1994

(Continued)

OTHER PUBLICATIONS

Exhibit I, search result p. 1 (2014).*  
Improper Markush Fed. Reg. vol. 76 p. 7162-7175, slides 1, 64-67 (2011).*  
Ostrowski et al. "An aza analogue . . . " Eur. J. Org. Chem. p. 1104-1110 (2003).*  
Paulsen et al. "Monosaccharides with . . . " Chemischte Berrichte v.102(11) p. 3864-62 (1969).*  
Holdworth et "World Associate . . . " Vet. Parasit. 136, p. 29-43 (2006).*  
Marchiondo et al. "World associ . . . " Vet. Parasit. 145, 332-344 (2007).*  
Ellis et al., "The synthesis of functionalized chiral bicyclic lactam and lactone N-oxides using a tandem Cope elimination/reverse Cope elimination protocol," Tetrahedron Letters, 2007, 48:1683-1686.  
Sato et al., "Novel glycosylation of the nitroxyl radicals with peracetylated glycosyl fluorides using a combination of $BF_3 \cdot OEt_2$ and an amine base as promoters," Carbohydrate Research, 2001, 334:215-222.

(Continued)

*Primary Examiner* — Celia Chang  
(74) *Attorney, Agent, or Firm* — Foley & Lardner LLP

(57) ABSTRACT

Provided is a cyclic amine compound, represented by the following formula (I) that has superior acaricidal activity, has superior properties and safety, and which can be synthesized industrially advantageously, a salt thereof and an acaricide:

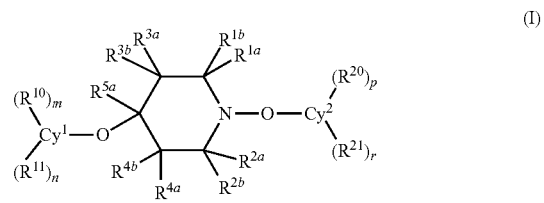

(I)

(wherein, $Cy^1$ and $Cy^2$ respectively and independently represent, for example, an aryl group, $R^{1a}$, $R^{1b}$, $R^{2a}$, $R^{2b}$, $R^{3a}$, $R^{3b}$, $R^{4a}$, $R^{4b}$ and $R^{5a}$ respectively and independently represent, for example, a hydrogen atom, $R^{1a}$ and $R^{2a}$ or $R^{3a}$ and $R^{4a}$ may together form, for example, an ethylene group, $R^{10}$, $R^{11}$, $R^{20}$ and $R^{21}$ respectively and independently represent, for example, an alkyl group, $R^{10}$ or $R^{11}$ may respectively or mutually, or together with an atom that bonds on $Cy^1$, form a ring, $R^{20}$ or $R^{21}$ on $Cy^2$ may respectively or mutually, or with an atom that bonds on $Cy^2$, form a ring, m represents an integer of 0 to 5, n represents an integer of 0 to 5, p represents an integer of 0 to 5, and r represents an integer of 0 to 5).

5 Claims, No Drawings

(51) Int. Cl.
*C07D 401/12* (2006.01)
*C07D 401/14* (2006.01)
*C07D 405/14* (2006.01)
*C07D 409/14* (2006.01)

(56) References Cited

U.S. PATENT DOCUMENTS

| | | | |
|---|---|---|---|
| 5,187,166 | A | 2/1993 | Kikuchi et al. |
| 5,216,156 | A * | 6/1993 | Galbo et al. .................. 544/198 |
| 5,286,865 | A | 2/1994 | Galbo et al. |
| 5,840,654 | A | 11/1998 | Kleemann |
| 8,349,923 | B2 | 1/2013 | Roth |
| 2004/0014784 | A1 | 1/2004 | Jakobi et al. |
| 2008/0280890 | A1 * | 11/2008 | Patil ........................... 514/227.8 |
| 2011/0212938 | A1 | 9/2011 | Xia et al. |

FOREIGN PATENT DOCUMENTS

| | | |
|---|---|---|
| EP | 0 467 848 B1 | 1/1996 |
| EP | 1439169 A1 | 7/2004 |
| JP | 08-034784 A | 2/1996 |
| JP | 08-508277 A | 9/1996 |
| WO | WO 00/71536 A1 | 11/2000 |
| WO | WO 03/017764 A1 | 3/2003 |
| WO | WO 2005/095380 A1 | 10/2005 |
| WO | WO 2007/022502 A2 | 2/2007 |
| WO | WO 2007/039563 A1 | 4/2007 |
| WO | WO 2007/040282 A1 | 4/2007 |
| WO | WO 2008/026658 A1 | 3/2008 |
| WO | WO 2008/101195 A2 | 8/2008 |
| WO | WO 2008/103613 A2 | 8/2008 |
| WO | WO 2008/126795 A1 | 10/2008 |
| WO | WO 2009/023180 A1 | 2/2009 |
| WO | WO 2009/028563 A1 | 3/2009 |
| WO | WO 2009/055331 A2 | 4/2009 |

OTHER PUBLICATIONS

U.S. Appl. No. 13/261,398, filed Feb. 24, 2011, Hamamoto et al.
Sosnovsky et al., "Preparation of 4-phosphorylated 1,4-dihydroxy-2,2,6,6-tetramethylpiperidines by reduction of nitroxyls with L-ascorbic acid," Synthesis, 1977, 9:619-622.
CAS RN 1049104-02-0, STN Entry Date Sep. 12, 2008.
CAS RN 770678-65-4, STN Entry Date Oct. 27, 2004.
International Search Report dated Apr. 5, 2011 in PCT/JP2011/054173.
Office Action dated Dec. 26, 2012 in TW 100106336.
Office Action dated May 24, 2013 in AU 2011221128.
Boehringer et al., "Benzhydryl and substituted benzhydryl ethers of nortropine, granatoline, and homogranatoline derivatives," CA 54:39199, 1960, 2 pages.
Klioze et al., "Benzenesulfenamides as antihypertensive agents. Substituted piperidine and 1-arylpiperazine derivatives," CA 93:46595, 1980, 1 page.
Shah et al., "Preparation of bicyclic piperidinyl- and piperazinylsulfonamides as inhibitors of 11β-hydroxysteroid dehydrogenase type 1 (11β-HSD1)," CA 150:259964, 2009, 2 pages.
Exhibit 1, p. 1-5, 2014.
Office Action dated May 14, 2014, in U.S. Appl. No. 13/261,398.
Supplementary European Search Report dated Sep. 2, 2014, in EP 10839311.7.

* cited by examiner

CYCLIC AMINE COMPOUND AND ACARICIDE

TECHNICAL FIELD

The present invention relates to a cyclic amine compound and an acaricide. More particularly, the present invention relates to a cyclic amine compound and an acaricide that have superior acaricidal activity, superior properties and safety, and which can be synthesized industrially advantageously.

The present application claims priority on the basis of Japanese Patent Application No. 2009-289576, filed in Japan on Dec. 21, 2009, Japanese Patent Application No. 2010-039839, filed in Japan on Feb. 25, 2010, and Japanese Patent Application No. 2010-117392, filed in Japan on May 21, 2010, the contents of which are incorporated herein by reference.

BACKGROUND ART

A compound having the structure represented by formula (A) is disclosed in Patent Document 1 as a compound that is structurally related to the compound of the present invention. This compound is described as being effective as a serotonin-4 receptor stimulator. However, there is no description of the specific synthesis method or efficacy of a compound in which X represents an oxygen atom, Y represents an alkoxy group and q represents 0 in formula (A).

[Chemical Formula 1]

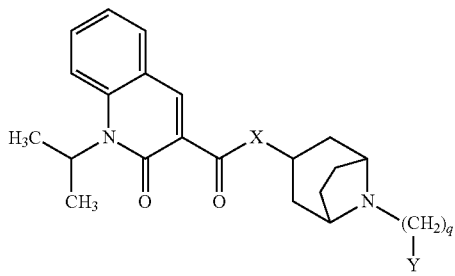

(A)

PRIOR ART DOCUMENTS

Patent Documents

Patent Document 1: Japanese Unexamined Patent Application, First Publication No. H8-34784

DISCLOSURE OF THE INVENTION

Problems to be Solved by the Invention

Previous acaricides were frequently unable to satisfy requirements relating to residual effects and other properties even though they were able to be synthesized industrially advantageously and were able to be used safely. In addition, the levels of requirements pertaining safety, such as reducing chemical damage to plants or reducing or eliminating toxicity to humans, livestock and fish, have annually become increasingly severe.

Therefore, an object of the present invention is to provide a cyclic amine compound and acaricide that have superior acaricidal activity, have superior properties, and safety, and can be synthesized industrially advantageously.

In addition, an object of the present invention is to provide an intermediate that is useful in the synthesis of the cyclic amine compound contained as an active ingredient in the aforementioned acaricide.

Means for Solving the Problems

As a result of conducting extensive studies to solve the aforementioned problems, the inventors of the present invention found that a cyclic amine compound having a specific structure, or a salt thereof, can be used as an acaricide that has superior acaricidal activity and demonstrates favorable properties and a high degree of safety. In addition, the inventors of the present invention found that a hydroxyamine compound having a specific structure, or a salt thereof, is preferable as an intermediate for synthesizing the cyclic amine compound having a specific structure or a salt thereof.

The present invention was completed based on these findings.

Namely, the present invention includes that indicated below.

[1] A cyclic amine compound represented by formula (I) or a salt thereof.

[Chemical Formula 2]

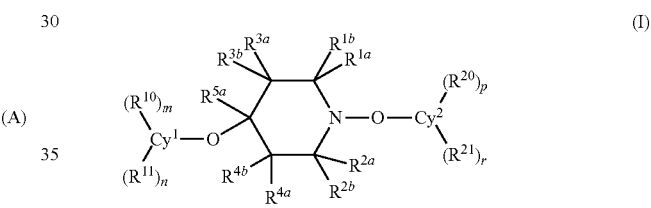

(I)

In formula (I), $Cy^1$ and $Cy^2$ respectively and independently represent a C6-10 aryl group or heterocyclic group.

In formula (I), $R^{1a}$, $R^{1b}$, $R^{2a}$, $R^{2b}$, $R^{3a}$, $R^{3b}$, $R^{4a}$, $R^{4b}$ and $R^{5a}$ respectively and independently represent a hydrogen atom or unsubstituted or substituted C1-6 alkyl group, and $R^{1a}$ and $R^{2a}$ or $R^{3a}$ and $R^{4a}$ may together form a C1-2 alkylene group, vinylene group or group represented by the formula —OCH$_2$—, —CH$_2$O—, —SCH$_2$—, —CH$_2$S—, —C(=O)CH$_2$—, —CH$_2$C(=O)—, —CH$_2$NR$^6$ or —NR$^6$CH$_2$— (wherein, $R^6$ represents a hydrogen atom, unsubstituted or substituted C1-6 alkyl group, unsubstituted or substituted C1-7 acyl group, or unsubstituted or substituted C1-6 alkoxycarbonyl group).

In formula (I), $R^{10}$, $R^{11}$, $R^{20}$ and $R^{21}$ respectively and independently represent an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxyl group, oxo group, unsubstituted or substituted C1-6 alkoxy group, unsubstituted or substituted C3-8 cycloalkoxy group, unsubstituted or substituted C2-6 alkenyloxy group, unsubstituted or substituted C2-6 alkynyloxy group, carboxyl group, unsubstituted or substituted C1-7 acyl group, unsubstituted or substituted C1-6 alkoxycarbonyl group, unsubstituted or substituted C2-6 alkenyloxycarbonyl group, unsubstituted or substituted C2-6 alkynyloxycarbonyl group, unsubstituted or substituted C1-7 acyloxy group, unsubstituted or substituted C1-6 alkylideneaminooxy group, unsubstituted or substituted C6-10 aryl group, unsubstituted or substituted heterocyclic group, unsubstituted or substituted C6-10 aryloxy group, unsubstituted or substituted heterocyclyloxy group, amino group, unsubstituted or substituted C1-6 alkylamino group, unsubstituted or substituted C6-10 arylamino group, unsubstituted or substituted heterocyclylamino group, unsubstituted or substituted C1-7 acylamino group, unsubstituted or substituted C1-6 alkoxycarbonylamino group, unsubstituted or substituted aminocarbonyl group, unsubstituted or substituted ureido group, mercapto group, unsubstituted or substituted C1-6 alkylthio group, unsubstituted or substituted C6-10 arylthio group, unsubstituted or substituted heterocyclylthio group, (unsubstituted or substituted C1-6 alkyl)thiocarbonyl group, (unsubstituted or substituted C1-6 alkoxy)thiocarbonyl group, (unsubstituted or substituted C1-6 alkythio)carbonyl group, (unsubstituted or substituted C1-6 alkylthio)thiocarbonyl group, tri-C1-6 alkyl-substituted silyl group, tri-C6-10 aryl-substituted silyl group, cyano group, nitro group or halogen atom.

In formula (I), $R^{10}$ or $R^{11}$ on $Cy^1$ may respectively or mutually, or together with an atom that bonds on $Cy^1$, form a ring, and $R^{20}$ or $R^{21}$ on $Cy^2$ may respectively or mutually, or with an atom that bonds on $Cy^2$, form a ring.

In formula (I), m represents the number of $R^{10}$ and is an integer of 0 to 5, and when m is 2 or more, $R^{10}$ may be mutually the same or different.

In formula (I), n represents the number of $R^{11}$ and is an integer of 0 to 5, and when n is 2 or more, $R''$ may be mutually the same or different.

In formula (I), p represents the number of $R^{20}$ and is an integer of 0 to 5, and when p is 2 or more, $R^{20}$ may be mutually the same or different.

In formula (I), r represents the number of $R^{21}$ and is an integer of 0 to 5, and when r is 2 or more, $R^{21}$ may be mutually the same or different.

[2] The cyclic amine compound or salt thereof described in [1]above, wherein $Cy^1$ in formula (I) represents a phenyl group, pyrazolyl group, thiadiazolyl group, pyridyl group, pyrimidinyl group or pyridazinyl group, and $Cy^2$ represents a phenyl group, pyrazolyl group, thiadiazolyl group, pyridyl group, pyrimidinyl group or pyridazinyl group.

[3] The cyclic amine compound or salt thereof described in [1] or [2] above, wherein $R^{10}$ in formula (I) represents a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group, $R^{11}$ in formula (I) represents a cyano group, halogen atom, C1-6 haloalkyl group, C2-6 haloalkenyl group or C2-6 haloalkynyl group, $R^{20}$ in formula (I) represents a cyano group, halogen atom, C1-6 haloalkyl group, C2-6 haloalkenyl group or C2-6 haloalkynyl group, and $R^{21}$ in formula (I) represents a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group.

[4] The cyclic amine compound or salt thereof described in any of [1] to [3] above wherein, the formula (I) is formula (II).

[Chemical Formula 3]

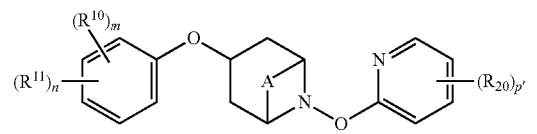

(II)

In formula (II), $R^{10}$, m, $R^{11}$, n and $R^{20}$ are same as previously defined in formula (I).

In formula (II), A represents a C1-2 alkylene group, vinylene group, or group represented by the formula —OCH$_2$—, —CH$_2$O—, —SCH$_2$—, —CH$_2$S—, —C(=O)CH$_2$—, —CH$_2$C(=O)—, —CH$_2$NR$^6$ or —NR$^6$CH$_2$— (wherein, $R^6$ represents a hydrogen atom, unsubstituted or substituted C1-6 alkyl group, unsubstituted or substituted C1-7 acyl group, or unsubstituted or substituted C1-6 alkoxycarbonyl group).

In formula (II), p' represents the number of $R^{20}$ and is an integer of any of 0 to 4, and when p' is 2 or more, $R^{20}$ may be mutually the same or different.

[5] The cyclic amine compound or salt thereof described in [1] or [2], wherein $R^{1a}$ and $R^{2a}$ or $R^{3a}$ and $R^{4a}$ in formula (I) together form a C2 alkylene group.

[6] An acaricide containing as an active ingredient thereof at least one type selected from the cyclic amine compound or salt thereof described in any of [1] to [5] above.

[7] A hydroxyamine compound represented by formula (III) or a salt thereof.

[Chemical Formula 4]

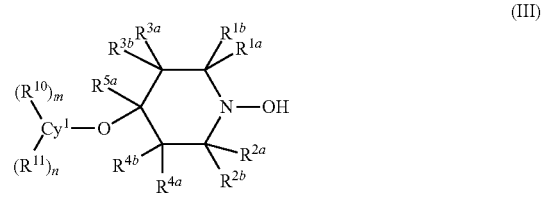

(III)

In formula (III), $Cy^1$ represents a C6-10 aryl group or heterocyclic group.

In formula (III), $R^{1a}$, $R^{1b}$, $R^{2a}$, $R^{2b}$, $R^{3a}$, $R^{3b}$, $R^{4a}$, $R^{4b}$ and $R^{5a}$ respectively and independently represent a hydrogen atom or unsubstituted or substituted C1-6 alkyl group, and $R^{1a}$ and $R^{2a}$ or $R^{3a}$ and $R^{4a}$ may together form a C1-2 alkylene group, vinylene group or group represented by the formula —OCH$_2$—, —CH$_2$O—, —SCH$_2$—, —CH$_2$S—, —C(=O)CH$_2$—, —CH$_2$C(=O)—, —CH$_2$NR$^6$ or —NR$^6$CH$_2$— (wherein, $R^6$ represents a hydrogen atom, unsubstituted or substituted C1-6 alkyl group, unsubstituted or substituted C1-7 acyl group, or unsubstituted or substituted C1-6 alkoxycarbonyl group).

In formula (III), $R^{10}$ and $R^{11}$ respectively and independently represent an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxyl group, oxo group, unsubstituted or substituted C1-6 alkoxy group, unsubstituted or substituted C3-8 cycloalkoxy group, unsubstituted or substituted C2-6 alkenyloxy group, unsubstituted or substituted C2-6 alkynyloxy group, carboxyl group, unsubstituted or substituted C1-7 acyl group, unsubstituted or substituted C1-6 alkoxycarbonyl group, unsubstituted or substituted C2-6 alkenyloxycarbonyl group, unsubstituted or substituted C2-6 alkynyloxycarbonyl group, unsubstituted or substituted C1-7 acyloxy group, unsubstituted or substituted C1-6 alkylideneaminooxy group, unsubstituted or substituted C6-10 aryl group, unsubstituted or substituted heterocyclic group, unsubstituted or substituted C6-10 aryloxy group, unsubstituted or substituted heterocyclyloxy group, amino group, unsubstituted or substituted C1-6 alkylamino group, unsubstituted or substituted C6-10 arylamino group, unsubstituted or substituted heterocyclylamino group, unsubstituted or substituted C1-7 acylamino group, unsubstituted or substituted C1-6 alkoxycarbonylamino group, unsubstituted or substituted aminocarbonyl group, unsubstituted or substituted ureido group, mercapto group, unsubstituted or substituted C1-6 alkylthio group, unsubstituted or substituted C6-10 arylthio group, unsubstituted or substituted heterocyclylthio group, (unsubstituted or substituted C1-6 alkyl)thiocarbonyl group, (unsubstituted or substituted C1-6 alkoxy) thiocarbonyl group, (unsubstituted or substituted C1-6 alkythio)carbonyl group, (unsubstituted or substituted C1-6 alkylthio)thiocarbonyl group, tri-C1-6 alkyl-substituted silyl group, tri-C6-10 aryl-substituted silyl group, cyano group, nitro group or halogen atom.

In formula (III), $R^{10}$ or $R^{11}$ on $Cy^1$ may respectively or mutually, or together with an atom that bonds on $Cy^1$, form a ring.

In formula (III), m represents the number of $R^{10}$ and is an integer of 0 to 5, and when m is 2 or more, $R^{10}$ may be mutually the same or different.

In formula (III), n represents the number of $R^{11}$ and is an integer of 0 to 5, and when n is 2 or more, $R^{11}$ may be mutually the same or different.

[8] The hydroxyamine compound or salt thereof described in [7] above, wherein $Cy^1$ in formula (III) represents a phenyl group, pyrazolyl group, thiadiazolyl group, pyridyl group, pyrimidinyl group or pyridazinyl group.

[9] The hydroxyamine compound or salt thereof described in [7] or [8] above, wherein $R^{10}$ in formula (III) represents a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group, and $R^{11}$ in formula (III) represents a cyano group, halogen atom, C1-6 haloalkyl group, C2-6 haloalkenyl group or C2-6 haloalkynyl group.

[10] The hydroxyamine compound or salt thereof described in [7] or [8] above, wherein $R^{1a}$ and $R^{2a}$ or $R^{3a}$ and $R^{4a}$ in formula (III) together form a C2 alkylene group.

Effects of the Invention

The cyclic amine compound or salt thereof according to the present invention is able to effectively control acari and the like harmful to agricultural crops and in terms of hygiene.

Use of the hydroxyamine compound or salt thereof according to the present invention makes it possible to easily synthesize the cyclic amine compound or salt thereof according to the present invention.

BEST MODE FOR CARRYING OUT THE INVENTION (Cyclic Amine Compound)

The cyclic amine compound according to the present invention is a compound represented by formula (I) or formula (II). In addition, a salt of the cyclic amine compound according to the present invention is a salt of a compound represented by formula (I) or formula (II).

The term "unsubstituted" in the present description refers only to a core group. Unless specifically indicated otherwise, a group has the meaning of being "unsubstituted" when the group is not described as being "substituted" and is described using only the name of the core group.

On the other hand, the term "substituted" refers to any hydrogen of the core group being substituted with a group having a structure that is the same as or different from the core group. Thus, a "substituent" is another group bonded to the core group. A group may have one substituent or two or more substituents. The two or more substituents may be the same or different.

The term "C1-6", for example, means that the number of carbon atoms of the core group is from 1 to 6. The number of carbon atoms present in a substituent or substituents is not included in the number of carbon atoms. For example, a butyl group having an ethoxy group as a substituent thereof is classified as a C2 alkoxy C4 alkyl group.

There are no particular limitations on "substituents" provided they are chemically acceptable and allow the effects of the present invention to be demonstrated.

Examples of groups able to be "substituents" include halogen atoms such as a fluorine atom, chlorine atom, bromine atom or iodine atom; C1-6 alkyl group such as a methyl group, ethyl group, n-propyl group, i-propyl group, n-butyl group, s-butyl group, i-butyl group, t-butyl group, n-pentyl group or n-hexyl group; C3-8 cycloalkyl groups such as a cyclopropyl group, cyclobutyl group, cyclopentyl group, cyclohexyl group or cycloheptyl group; C2-6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group; C3-8 cycloalkenyl groups such as a 2-cyclopropenyl group, 2-cyclopentenyl group, 3-cyclohexenyl group or 4-cyclooctenyl group; C2-6 alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group;

C1-6 alkoxy groups such as a methoxy group, ethoxy group, n-propoxy group, i-propoxy group, n-butoxy group, s-butoxy group, i-butoxy group or t-butoxy group; C2-6 alkenyloxy groups such as a vinyloxy group, allyloxy group, propenyloxy group or butenyloxy group; C2-6 alkynyloxy groups such as a ethynyloxy group or propargyloxy group; C6-10 aryl groups such as a phenyl group or naphthyl group; C6-10 aryloxy groups such as a phenoxy group or 1-naphthoxy group; C7-11 aralkyl groups such as a benzyl group or phenethyl group; C7-11 aralkyloxy groups such as benzyloxy group or phenethyloxy group; C1-7 acyl groups such as a formyl group, acetyl group, propionyl group, benzoyl group or cyclohexylcarbonyl group; C1-7 acyloxy groups such as a formyloxy group, acetyloxy group, propionyloxy group, benzoyloxy group or cyclohexylcarbonyloxy group; C1-6 alkoxycarbonyl groups such as a methoxycarbonyl group, ethoxycarbonyl group, n-propoxycarbonyl group, i-propoxycarbonyl group, n-butoxycarbonyl group or t-butoxycarbonyl group; carboxyl groups;

hydroxyl groups; oxo groups; C1-6 haloalkyl groups such as a chloromethyl group, chloroethyl group, trifluoromethyl group, 1,2-dichloro-n-propyl group, 1-fluoro-n-butyl group or perfluoro-n-pentyl group; C2-6 haloalkenyl groups such as a 2-chloro-1-propenyl group or 2-fluoro-1-butenyl group; C2-6 haloalkynyl groups such as a 4,4-dichloro-1-butynyl group, 4-fluoro-1-pentynyl group or 5-bromo-2-pentynyl group; C1-6 haloalkoxy groups such as a 2-chloro-n-propoxy group or 2,3-dichlorobutoxy group; C2-6 haloalkenyloxy groups such as a 2-chloropropenyloxy group or 3-bromobutenyloxy group; C6-10 haloaryl groups such as a 4-chlorophenyl group, 4-fluorophenyl group or 2,4-dichlorophenyl group; C6-10 haloaryloxy groups such as a 4-fluorophenyloxy group or 4-chloro-1-naphthoxy group; halogen-substituted C1-7 acyl groups such as a chloroacetyl group, trifluoroacetyl group, trichloroacetyl group or 4-chlorobenzoyl group;

cyano groups; isocyano groups; nitro groups; isocyanato groups; cyanato groups; amino groups; C1-6 alkylamino groups such as a methylamino group, dimethylamino group or diethylamino group; C6-10 arylamino groups such as an anilino group or naphthylamino group; C7-11 aralkylamino groups such as a benzylamino group or phenylethylamino group; C1-7 acylamino groups such as a formylamino group, acetylamino group, propanoylamino group, butylylamino group, i-propylcarbonylamino group or benzoylamino group; C1-6 alkoxycarbonylamino groups such as a methoxycarbonylamino group, ethoxycarbonylamino group, n-propoxycarbonylamino group or i-propoxycarbonylamino group; unsubstituted or substituted aminocarbonyl groups such as an aminocarbonyl group, dimethylaminocarbonyl group, phenylaminocarbonyl group or N-phenyl-N-methylaminocarbonyl group; C1-6 alkyl groups substituted with an imino group such as an iminomethyl group, (1-imino)ethyl group or (1-imino)-n-propyl group; C1-6 alkyl groups substituted with a hydroxyimino group such as a hydroxyiminomethyl group, (1-hydroxyimino)ethyl group, (1-hydroxyimino)propyl group, methoxyiminomethyl group or (1-methoxyimino) ethyl group;

mercapto groups; isothiocyanato groups; thiocyanato groups; C1-6 alkylthio groups such as a methylthio group, ethylthio group, n-propylthio group, i-propylthio group, n-butylthio group, i-butylthio group, s-butylthio group or t-butylthio group; C2-6 alkenylthio groups such as a vinylthio group or allylthio group; C2-6 alkynylthio groups such as a ethynylthio group or propargylthio group; C6-10 arylthio groups such as a phenylthio group or naphthylthio group; heteroarylthio groups such as a thiazolylthio group or pyridylthio group; C7-11 aralkylthio groups such as a benzylthio group or phenethylthio group; (C1-6 alkythio)carbonyl groups such as a (methylthio)carbonyl group, (ethylthio)carbonyl group, (n-propylthio)carbonyl group, (i-propylthio) carbonyl group, (n-butylthio)carbonyl group, (i-butylthio) carbonyl group, (s-butylthio)carbonyl group or (t-butylthio) carbonyl group;

C1-6 alkylsulfinyl groups such as a methylsulfinyl group, ethylsulfinyl group or t-butylsulfinyl group; C2-6 alkenylsulfinyl groups such as an allylsulfinyl group; C2-6 alkynylsulfinyl groups such as a propargylsulfinyl group; C6-10 arylsulfinyl groups such as a phenylsulfinyl group; heteroarylsulfinyl groups such as a thiazolylsulfinyl group or pyridylsulfinyl group; C7-11 aralkylsulfinyl groups such as a benzylsulfinyl group or phenethylsulfinyl group; C1-6 alkylsulfonyl groups such as a methylsulfonyl group, ethylsulfonyl group or t-butylsulfonyl group; C2-6 alkenylsulfonyl groups such as an allylsulfonyl group; C2-6 alkynylsulfonyl groups such as a propargylsulfonyl group; C6-10 arylsulfonyl groups such as a phenylsulfonyl group; heteroarylsulfonyl groups such as a thiazolylsulfonyl group or pyridylsulfonyl group; C7-11 aralkylsulfonyl groups such as a benzylsulfonyl group or phenethylsulfonyl group;

5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group or tetrazolyl group; 6-membered heteroaryl groups such as a pyridyl group, pyrazinyl group, pyrimidinyl group, pyridazinyl group or triazinyl group; saturated heterocyclic groups such as a aziridinyl group, epoxy group, pyrrolidinyl group, tetrahydrofuranyl group, piperidyl group, piperazinyl group or morpholinyl group; tri-C1-6 alkyl-substituted silyl groups such as a trimethylsilyl group, triethylsilyl group or t-butyldimethylsilyl group; and triphenylsilyl groups. Among these, C1-6 alkyl groups, C1-6 alkoxy groups, halogen atoms or C1-6 haloalkyl groups are preferable.

In addition, these "substituents" may further have other "substituents".

[$Cy^1$ and $Cy^2$]

$Cy^1$ and $Cy^2$ in formula (I) respectively and independently represent a C6-10 aryl group or heterocyclic group.

A "C6-10 aryl group" represented by $Cy^1$ and $Cy^2$ may have a single ring or multiple rings. Multicyclic aryl groups may be groups in which at least one of the rings is an aromatic ring while the remaining rings are any of saturated aliphatic rings, unsaturated aliphatic rings or aromatic rings. Examples of C6-10 aryl groups include a phenyl group, naphthyl group, azulenyl group, indenyl group, indanyl group or tetralinyl group. Among these, the "C6-10 aryl group" represented by $Cy^1$ and $Cy^2$ is preferably a phenyl group.

A "heterocyclic group" represented by $Cy^1$ and $Cy^2$ is a group in which one to four heteroatoms selected from the group consisting of nitrogen atoms, oxygen atoms and sulfur atoms are contained as atoms that compose the ring. The heterocyclic group may have a single ring or multiple rings.

Examples of heterocyclic groups include 5-membered heteroaryl groups, 6-membered heteroaryl groups, condensed heteroaryl groups, saturated heterocyclic groups and partially unsaturated heterocyclic groups.

Examples of 5-membered heteroaryl groups include pyrrolyl groups such as a pyrrol-1-yl group, pyrrol-2-yl group or pyrrol-3-yl group; furyl groups such as a furan-2-yl group or furan-3-yl group; thienyl groups such as a thiophen-2-yl group or thiophen-3-yl group; imidazolyl groups such as a imidazol-1-yl group, imidazol-2-yl group, imidazol-4-yl group or imidazol-5-yl group; pyrazolyl groups such as a pyrazol-1-yl group, pyrazol-3-yl group, pyrazol-4-yl group or pyrazol-5-yl group; oxazolyl groups such as an oxazoyl-2-yl group, oxazolyl-4-yl group or oxazolyl-5-yl group; isoxazolyl groups such as an isoxazol-3-yl group, isoxazol-4-yl group or isoxazol-5-yl group; thiazolyl groups such as a thiazol-2-yl group, thiazol-4-yl group or thiazol-5-yl group; isothiazolyl groups such as an isothiazol-3-yl group, isothiazol-4-yl group or isothiazol-5-yl group; triazolyl groups such as a 1,2,3-triazol-1-yl group, 1,2,3-triazol-4-yl group, 1,2,3-triazol-5-yl group, 1,2,4-triazol-1-yl group, 1,2,4-triazol-3-yl group or 1,2,4-triazol-5-yl group; oxadiazolyl groups such as a 1,2,4-oxadiazol-3-yl group, 1,2,4-oxadiazol-5-yl group or 1,3,4-oxadiazol-2-yl group; thiadiazolyl groups such as a 1,2,4-thiadiazol-3-yl group, 1,2,4-thiadiazol-5-yl group or 1,3,4-thiadiazol-2-yl group; and tetrazolyl groups such as a tetrazol-1-yl group or tetrazol-2-yl group.

Examples of 6-membered heteroaryl groups include pyridyl groups such as a pyridin-2-yl group, pyridin-3-yl group or pyridin-4-yl group; pyrazinyl groups such as a pyrazin-2-yl group or pyrazin-3-yl group; pyrimidinyl groups such as a pyrimidin-2-yl group, pyrimidin-4-yl group or pyrimidin-5-yl group; pyridazinyl groups such as a pyridazin-3-yl group or pyridazin-4-yl group; and triazinyl groups.

Examples of condensed heteroaryl groups include indol-1-yl group, indol-2-yl group, indol-3-yl group, indol-4-yl group, indol-5-yl group, indol-6-yl group or indol-7-yl group; benzofuran-2-yl group, benzofuran-3-yl group, benzofuran-4-yl group, benzofuran-5-yl group, benzofuran-6-yl group or benzofuran-7-yl group; benzothiophen-2-yl group, benzothiophen-3-yl group, benzothiophen-4-yl group, benzothiophen-5-yl group, benzothiophen-6-yl group or benzothiophen-7-yl group; benzoimidazol-1-yl group, benzoimidazol-2-yl group, benzoimidazol-4-yl group or benzoimidazol-5-yl group; benzoxazol-2-yl group, benzoxazol-4-yl group or benzoxazol-5-yl group; benzothiazol-2-yl group, benzothiazol-4-yl group or benzothiazol-5-yl group; and quinolin-2-yl group, quinolin-3-yl group, quinolin-4-yl group, quinolin-5-yl group, quinolin-6-yl group, quinolin-7-yl group or quinolin-8-yl group.

Examples of other heterocyclic groups include aziridin-1-yl group or aziridin-2-yl group; epoxy groups; pyrrolidin-1-yl group, pyrrolidin-2-yl group or pyrrolidin-3-yl group; tetrahydrofuran-2-yl group or tetrahydrofuran-3-yl group; piperidin-1-yl group, piperidin-2-yl group, piperidin-3-yl group or piperidin-4-yl group; piperazin-1-yl group or piperazin-2-yl group; morpholin-2-yl group, morpholin-3-yl group or morpholin-4-yl group; 1,3-benzodioxazol-4-yl group or 1,3-benzodioxazol-5-yl group; 1,4-benzodioxan-5-yl group, 1,4-benzodioxan-6-yl group, 3,4-dihydro-2H-1,5-benzodioxepin-6-yl group or 3,4-dihydro-2H-1,5-benzodioxepin-7-yl group; and 2,3-dihydrobenzofuran-4-yl group, 2,3-dihydrobenzofuran-5-yl group, 2,3-dihydrobenzofuran-6-yl group or 2,3-dihydrobenzofuran-7-yl group.

Among these, the "heterocyclic group" represented by $Cy^1$ or $Cy^2$ is preferably a 5-membered heteroaryl group or 6-membered heteroaryl group, and more preferable a pyrazolyl group, thiadiazolyl group, pyridyl group, pyrimidinyl group or pyridazinyl group.

In the cyclic amine compound according to the present invention, $Cy^1$ is preferably a phenyl group and $Cy^2$ is preferably a pyridyl group.

[$R^{1a}$, $R^{1b}$, $R^{2a}$, $R^{2b}$, $R^{3a}$, $R^{3b}$, $R^{4a}$, $R^{4b}$ and $R^{5a}$]

In formula (I), $R^{1a}$, $R^{1b}$, $R^{2a}$, $R^{2b}$, $R^{3a}$, $R^{3b}$, $R^{4a}$, $R^{4b}$ and $R^{5a}$ (to be collectively referred to as $R^{1a}$ and the like) respectively and independently represent a hydrogen atom or unsubstituted or substituted C1-6 alkyl group.

A "C1-6 alkyl group" represented by $R^{1a}$ and the like may be linear or branched. Examples of alkyl groups include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methylbutyl group, 2,2-dimethylpropyl group and i-hexyl group.

Examples of a "substituted C1-6 alkyl group" represented by $R^{1a}$ and the like include C3-8 cycloalkyl C1-6 alkyl groups such as a cyclopropylmethyl group, 2-cyclopropylethyl group, cyclopentylmethyl group, 2-cyclohexylethyl group or 2-cyclooctylethyl group; C1-6 haloalkyl groups such as a fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group, perfluorooctyl group, perchlorooctyl group or 2,4,6-trichlorohexyl group;

hydroxy C1-6 alkyl groups such as a hydroxymethyl group or 2-hydroxyethyl group; C1-6 alkoxy C1-6 alkyl groups such as a methoxymethyl group, ethoxymethyl group, methoxyethyl group, ethoxyethyl group, methoxy-n-propyl group, n-propoxymethyl group, i-propoxyethyl group, s-butoxymethyl group or t-butoxyethyl group; C1-6 alkoxy C1-6 alkoxy C1-6 alkyl groups such as a methoxymethoxymethyl group, 1-methoxyethoxymethyl group, 2-methoxyethoxymethyl group, 2-(1-methoxyethoxy)ethyl group or 2-(2-methoxyethoxy)ethyl group; di-C1-6 alkoxy C1-6 alkyl groups such as a dimethoxymethyl group, diethoxymethyl group, 2,2-dimethoxyethyl group, 1,2-dimethoxyethyl group, 3,3-dimethoxy-n-propyl group or 2,2-diethoxyethyl group; C1-7 acyloxy C1-6 alkyl groups such as a formyloxymethyl group, acetoxymethyl group, 2-acetoxyethyl group, propionyloxymethyl group or propionyloxyethyl group; imino-substituted C1-6 alkyl groups such as a iminomethyl group, (1-imino)ethyl group or (1-imino)propyl group; hydroxyimino-substituted C1-6 alkyl groups such as a hydroxyiminomethyl group, (1-hydroxyimino)ethyl group, (1-hydroxyimino)-n-propyl group, methoxyiminomethyl group or (1-methoxyimino)ethyl group; and unsubstituted or substituted C7-11 aralkyl groups such as an unsubstituted or substituted benzyl group or unsubstituted or substituted phenethyl group.

$R^{1a}$ and $R^{2a}$ or $R^{3a}$ and $R^{4a}$ may together form a C1-2 alkylene group, vinylene group or group represented by the formula —OCH$_2$—, —CH$_2$O—, —SCH$_2$—, —CH$_2$S—, —C(=O)CH$_2$—, —CH$_2$C(=O)—, —CH$_2$NR$^6$— or —NR$^6$CH$_2$— (wherein, R$^6$ represents a hydrogen atom, unsubstituted or substituted C1-6 alkyl group, unsubstituted or substituted C1-7 acyl group, or unsubstituted or substituted C1-6 alkoxycarbonyl group).

Examples of a "C1-2 alkylene group" include a methylene group and ethylene group, and an ethylene group is preferable.

$R^6$ represents a hydrogen atom, unsubstituted or substituted C1-6 alkyl group, unsubstituted or substituted C1-7 acyl group, or unsubstituted or substituted C1-6 alkoxycarbonyl group.

Examples of an "unsubstituted or substituted C1-6 alkyl group" represented by $R^6$ are the same as those listed as examples of $R^{1a}$ and the like.

Examples of a "C1-7 acyl group" represented by $R^6$ include a formyl group, acetyl group, propionyl group, benzoyl group and cyclohexylcarbonyl group.

Examples of a "substituted C1-7 acyl group" represented by $R^6$ include a chloroacetyl group, trifluoroacetyl group, trichloroacetyl group and 4-chlorobenzoyl group.

Examples of a "C1-6 alkoxycarbonyl group" represented by $R^6$ include a methoxycarbonyl group, ethoxycarbonyl group, n-propoxycarbonyl group, i-propoxycarbonyl group, n-butoxycarbonyl group and t-butoxycarbonyl group.

Examples of a "substituted C1-6 alkoxycarbonyl group" represented by $R^6$ include C3-8 cycloalkyl C1-6 alkoxycarbonyl groups such as a cyclopropylmethoxycarbonyl group, cyclobutylmethoxycarbonyl group, cyclopentylmethoxycarbonyl group, cyclohexylmethoxycarbonyl group, 2-methylcyclopropylmethoxycarbonyl group, 2,3-dimethylcyclopropylmethoxycarbonyl group, 2-chlorocyclopropylmethoxycarbonyl group or 2-cyclopropylethoxycarbonyl group; and C1-6 haloalkoxycarbonyl groups such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group, 2,2,2-trichloroethoxycarbonyl group, pentafluoroethoxycarbonyl group, 4-fluorobutoxycarbonyl group, 3,3,3-trifluoropropoxycarbonyl group, 2,2,2-trifluoro-1-trifluoromethylethoxycarbonyl group or perfluorohexyloxycarbonyl group.

In the case a crosslinked moiety is specifically represented in formula (I), the crosslinked moiety can be represented with the following partial structural formulas (a1) to (a4). Asterisks (*) in formula (a1) to (a4) indicate the locations of bonds with an oxygen atom bonded by $Cy^1$. Plus symbols (+) in formulas (a1) to (a4) indicate the locations of bonds with oxygen atoms bonded by $Cy^2$. X' respectively and independently represents a carbon atom, oxygen atom, sulfur atom, $-NR^6-$ or carbonyl group. Isomers in which the relationship between a crosslinked moiety and $R^{5a}$ is in an exo or endo relationship as well as mixtures thereof are also included in the present invention.

[Chemical Formula 5]
Error! Objects cannot be created from editing field codes.
$[R^{10}, R^{11}, R^{20} \text{ and } R^{21}]$ $R^{10}, R^{11}, R^{20}$ and $R^{21}$ in formula (I) (to be collectively referred to as $R^{10}$ and the like) respectively and independently represent an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxyl group, oxo group, unsubstituted or substituted C1-6 alkoxy group, unsubstituted or substituted C3-8 cycloalkoxy group, unsubstituted or substituted C2-6 alkenyloxy group, unsubstituted or substituted C2-6 alkynyloxy group, carboxyl group, unsubstituted or substituted C1-7 acyl group, unsubstituted or substituted C1-6 alkoxycarbonyl group, unsubstituted or substituted C2-6 alkenyloxycarbonyl group, unsubstituted or substituted C2-6 alkynyloxycarbonyl group, unsubstituted or substituted C1-7 acyloxy group, unsubstituted or substituted C1-6 alkylideneaminooxy group, unsubstituted or substituted C6-10 aryl group, unsubstituted or substituted heterocyclic group, unsubstituted or substituted C6-10 aryloxy group, unsubstituted or substituted heterocyclyloxy group, amino group, unsubstituted or substituted C1-6 alkylamino group, unsubstituted or substituted C6-10 arylamino group, unsubstituted or substituted heterocyclylamino group, unsubstituted or substituted C1-7 acylamino group, unsubstituted or substituted C1-6 alkoxycarbonylamino group, unsubstituted or substituted aminocarbonyl group, unsubstituted or substituted ureido group, mercapto group, unsubstituted or substituted C1-6 alkylthio group, unsubstituted or substituted C6-10 arylthio group, unsubstituted or substituted heterocyclylthio group, (unsubstituted or substituted C1-6 alkyl)thiocarbonyl group, (unsubstituted or substituted C1-6 alkoxy)thiocarbonyl group, (unsubstituted or substituted C1-6 alkythio)carbonyl group, (unsubstituted or substituted C1-6 alkylthio)thiocarbonyl group, tri-C1-6 alkyl-substituted silyl group, tri-C6-10 aryl-substituted silyl group, cyano group, nitro group or halogen atom.

m represents the number of $R^{10}$, is an integer of 0 to 5, and is preferably 1. When m is 2 or more, $R^{10}$ may be mutually the same or different.

n represents the number of $R^{11}$, is an integer of 0 to 5, and is preferably 1. When n is 2 or more, $R^{11}$ may be mutually the same or different.

p represents the number of $R^{20}$, is an integer of 0 to 5, and is preferably 1. When n is 2 or more, $R^{20}$ may be mutually the same or different.

r represents the number of $R^{21}$, is an integer of 0 to 5, and is preferably 0 or 1. When r is 2 or more, $R^{21}$ may be mutually the same or different.

Examples of an "unsubstituted or substituted C1-6 alkyl group" represented by $R^{10}$ and the like are the same as those listed as examples of the aforementioned $R^{1a}$ and the like.

Examples of a "C3-8 cycloalkyl group" represented by $R^{10}$ and the like include a cyclopropyl group, cyclobutyl group, cyclopentyl group, cyclohexyl group and cycloheptyl group.

Examples of a "substituted cycloalkyl group" represented by $R^{10}$ and the like include a chlorocyclohexyl group, bromocyclohexyl group, 2-methylcyclopropyl group and 2,3-dimethylcyclopropyl group.

Examples of a "C2-6 alkenyl group" represented by $R^{10}$ and the like include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

Examples of a "substituted C2-6 alkenyl group" represented by $R^{10}$ and the like include C2-6 haloalkenyl groups such as a 2-chloro-1-propenyl group and 2-fluoro-1-butenyl group.

Examples of a "C2-6 alkynyl group" represented by $R^{10}$ and the like include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

Examples of a "substituted C2-6 alkynyl group" represented by $R^{10}$ and the like include C2-6 haloalkynyl groups such as a 4,4-dichloro-1-butynyl group, 4-fluoro-1-pentynyl group and 5-bromo-2-pentynyl group.

Examples of a "C1-6 alkoxy group" represented by $R^{10}$ and the like include a methoxy group, ethoxy group, i-propoxy group, n-butoxy group, i-butoxy group, s-butoxy group, t-butoxy group, n-pentyloxy group, i-pentyloxy group and n-hexyloxy group. Among these, C4-6 alkoxy groups are preferable.

Examples of a "substituted C1-6 alkoxy group" represented by $R^{10}$ and the like include C1-6 haloalkoxy groups such as a fluoromethoxy group, chloromethoxy group, bromomethoxy group, difluoromethoxy group, dichloromethoxy group, dibromomethoxy group, trifluoromethoxy group, trichloromethoxy group, tribromomethoxy group, 2,2,2-trifluoroethoxy group, 2,2,2-trichloroethoxy group, pentafluoroethoxy group, 4-fluorobutoxy group, 3,3,3-trifluoropropoxy group, 2,2,2-trifluoro-1-trifluoromethylethoxy group or perfluorohexyloxy group; C1-6 alkoxy C1-6 alkoxy groups such as a methoxymethoxy group, 1-methoxyethoxy group, 2-methoxyethoxy group, ethoxymethoxy group, 1-ethoxyethoxy group, 2-ethoxyethoxy group, 1-methoxy-n-propoxy group, 2-methoxy-n-propoxy group or 3-methoxy-n-propoxy group; C3-8 cycloalkyl C1-6 alkoxy groups such as a cyclopropylmethoxy group, cyclobutylmethoxy group, cyclopentylmethoxy group, cyclohexylmethoxy group, 2-methylcyclopropylmethoxy group, 2,3-dimethylcyclopropylmethoxy group or 2-cyclopropylethoxy group; and C7-11 aralkyloxy groups such as a benzyloxy group or phenethyloxy group.

Examples of a "C3-8 cycloalkoxy group" represented by $R^{10}$ and the like include a cyclopropyloxy group, cyclobutyloxy group, cyclopentyloxy group, cyclohexyloxy group and cycloheptyloxy group.

Examples of a "C2-6 alkenyloxy group" represented by $R^{10}$ and the like include a vinyloxy group, 1-propenyloxy group, 2-propenyloxy group, 1-butenyloxy group, 2-butenyloxy group, 3-butenyloxy group, 1-methyl-2-propenyloxy group, 2-methyl-2-propenyloxy group, 1-pentenyloxy group, 2-pentenyloxy group, 1-methyl-2-butenyloxy group, 2-methyl-2-butenyloxy group, 1-hexenyloxy group and 2-hexenyloxy group.

Examples of a "substituted C2-6 alkenyloxy group" represented by $R^{10}$ and the like include C2-6 haloalkenyloxy groups such as a 2-chloro-1-propenyloxy group and 2-fluoro-1-butenyloxy group.

Examples of a "C2-6 alkynyloxy group" represented by $R^{10}$ and the like include an ethynyloxy group, 1-propynyloxy group, 2-propynyloxy group, 1-butynyloxy group, 2-butynyloxy group, 3-butynyloxy group, 1-methyl-2-propynyloxy group, 2-methyl-3-butynyloxy group, 1-pentynyloxy group, 2-pentynyloxy group, 1-methyl-2-butynyloxy group, 2-methyl-3-pentynyloxy group and 1-hexynyloxy group.

Examples of a "substituted C2-6 alkynyloxy group" represented by $R^{10}$ and the like include C2-6 haloalkynyloxy groups such as a 4,4-dichloro-1-butynyloxy group, 4-fluoro-1-pentynyloxy group and 5-bromo-2-pentynyloxy group.

Examples of a "C1-7 acyl group" represented by $R^{10}$ and the like include a formyl group, acetyl group, propionyl group and benzoyl group.

Examples of a "substituted C1-7 acyl group" represented by $R^{10}$ and the like include halogen-substituted C1-7 acyl groups such as a chloroacetyl group, trifluoroacetyl group, trichloroacetyl group and 4-chlorobenzoyl group.

Examples of a "C1-6 alkoxycarbonyl group" represented by $R^{10}$ and the like include a methoxycarbonyl group, ethoxycarbonyl group, n-propoxycarbonyl group and i-propoxycarbonyl group. Examples of a "substituted C1-6 alkoxycarbonyl group" represented by $R^{10}$ and the like include C3-8 cycloalkyl C1-6 alkoxycarbonyl groups such as a cyclopropylmethoxycarbonyl group, cyclobutylmethoxycarbonyl group, cyclopentylmethoxycarbonyl group, cyclohexylmethoxycarbonyl group, 2-methylcyclopropylmethoxycarbonyl group, 2,3-dimethylcyclopropylmethoxycarbonyl group, 2-chlorocyclopropylmethoxycarbonyl group or 2-cyclopropylethoxycarbonyl group; and C1-6 haloalkoxycarbonyl groups such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group, 2,2,2-trichloroethoxycarbonyl group, pentafluoroethoxycarbonyl group, 4-fluorobutoxycarbonyl group, 3,3,3-trifluoropropoxycarbonyl group, 2,2,2-trifluoro-1-trifluoromethylethoxycarbonyl group or perfluorohexyloxycarbonyl group.

Examples of a "C2-6 alkenyloxycarbonyl group" represented by $R^{10}$ and the like include an ethenyloxycarbonyl group, 2-propenyloxycarbonyl group and 1-propenyloxycarbonyl group.

Examples of a "substituted 2-6 alkenyloxycarbonyl group" represented by $R^{10}$ and the like include a 1-methyl-2-propenyloxycarbonyl group and 2-methyl-1-propenyloxycarbonyl group.

Examples of a "C2-6 alkynyloxycarbonyl group" represented by $R^{10}$ and the like include an ethynyloxycarbonyl group, propargyloxycarbonyl group and 2-butynyloxycarbonyl group.

Examples of a "substituted C2-6 alkynyloxycarbonyl group" represented by $R^{10}$ and the like include a 1-methylpropargyloxycarbonyl group.

Examples of a "C1-7 acyloxy group" represented by $R^{10}$ and the like include a formyloxy group, acetyloxy group and propionyloxy group.

Examples of a "substituted C1-7 acyloxy group" represented by $R^{10}$ and the like include halogen-substituted C1-7 acyloxy groups such as a chloroacetyloxy group, trifluoroacetyloxy group, trichloroacetyloxy group or 4-chlorobenzoyloxy group.

Examples of a "C1-6 alkylideneaminooxy group" represented by $R^{10}$ and the like include a methylideneaminooxy group, ethylideneaminooxy group, n-propylideneaminooxy group, i-propylideneaminooxy group, n-butylideneaminooxy group, i-butylideneaminooxy group and s-butylideneaminooxy group.

Examples of a "C6-10 aryl group" represented by $R^{10}$ and the like are the same as those listed as examples represented by the aforementioned $Cy^1$ and the like.

Examples of a "heterocyclic group" represented by $R^{10}$ and the like are the same as those listed as examples represented by the aforementioned $Cy^1$ and the like.

Examples of a "C6-10 aryloxy group" represented by $R^{10}$ and the like include a phenoxy group and naphthoxy group.

Examples of a "heterocyclyloxy group" represented by $R^{10}$ and the like include a pyridyloxy group and pyridazinyloxy group.

Examples of a "C1-6 alkylamino group" represented by $R^{10}$ and the like include a methylamino group, dimethylamino group and diethylamino group.

Examples of a "C6-10 arylamino group" represented by $R^{10}$ and the like include an anilino group and naphthylamino group.

Examples of a "heterocyclylamino group" represented by $R^{10}$ and the like include a pyridylamino group and pyridazinylamino group.

Examples of a "C1-7 acylamino group" represented by $R^{10}$ and the like include a formylamino group, acetylamino group, propanoylamino group, butylylamino group, 1-propylcarbonylamino group and benzoylamino group.

Examples of a "C1-6 alkoxycarbonylamino group" represented by $R^{10}$ and the like include a methoxycarbonylamino group, ethoxycarbonylamino group, n-propoxycarbonylamino group and i-propoxycarbonylamino group.

Examples of a "substituted aminocarbonyl group" represented by $R^{10}$ and the like include a dimethylaminocarbonyl group, phenylaminocarbonyl group and N-phenyl-N-methylaminocarbonyl group.

Examples of a "substituted ureido group" represented by $R^{10}$ and the like include 3-(C1-6 alkyl)ureido groups such as a 3-methylureido group or 3-ethylureido group; and 1,3-di(C1-6 alkyl)ureido groups such as a 1,3-dimethylureido group.

Examples of a "C1-6 alkylthio group" represented by $R^{10}$ and the like include a methylthio group, ethylthio group, n-propylthio group, i-propylthio group, n-butylthio group, i-butylthio group, s-butylthio group and t-butylthio group.

Examples of a "C6-10 arylthio group" represented by $R^{10}$ and the like include a phenylthio group and naphthylthio group.

Examples of a "heterocyclylthio group" represented by $R^{10}$ and the like include a pyridylthio group and pyridazinylthio group.

Examples of a "(C1-6 alkyl)thiocarbonyl group" represented by $R^{10}$ and the like include a methyl(thiocarbonyl) group, ethyl(thiocarbonyl) group, n-propyl(thiocarbonyl) group, i-propyl(thiocarbonyl) group, n-butyl(thiocarbonyl) group, i-butyl(thiocarbonyl) group, s-butyl(thiocarbonyl) group and t-butyl(thiocarbonyl) group.

Examples of a "(C1-6 alkoxy)thiocarbonyl group" represented by $R^{10}$ and the like include a methoxy(thiocarbonyl) group, ethoxy(thiocarbonyl) group, n-propoxy(thiocarbonyl) group, i-propoxy(thiocarbonyl) group, n-butoxy(thiocarbonyl) group, i-butoxy(thiocarbonyl) group, s-butoxy(thiocarbonyl) group and t-butoxy(thiocarbonyl) group.

Examples of a "(C1-6 alkylthio)carbonyl group" represented by $R^{10}$ and the like include a (methylthio)carbonyl group, (ethylthio)carbonyl group, (n-propylthio)carbonyl group, (i-propylthio)carbonyl group, (n-butylthio)carbonyl group, (i-butylthio)carbonyl group, (s-butylthio)carbonyl group and (t-butylthio)carbonyl group.

Examples of a "(C1-6 alkylthio)thiocarbonyl group" represented by $R^{10}$ and the like include a (methylthio)thiocarbonyl group, (ethylthio)thiocarbonyl group, (n-propylthio)thiocarbonyl group, (i-propylthio)thiocarbonyl group, (n-butylthio)thiocarbonyl group, (i-butylthio)thiocarbonyl group, (s-butylthio)thiocarbonyl group and (t-butylthio)thiocarbonyl group.

Examples of a "tri-C1-6 alkyl-substituted silyl group" represented by $R^{10}$ and the like include a trimethylsilyl group, triethylsilyl group and t-butyldimethylsilyl group.

Examples of a "tri-C6-10 aryl-substituted silyl group" represented by $R^{10}$ and the like include a triphenylsilyl group.

Examples of a "halogen atom" represented by $R^{10}$ and the like include a chlorine atom, bromine atom, fluorine atom and iodine atom.

In formula (I), $R^{10}$ is preferably a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group. Among these, $R^{10}$ is more preferably a C1-6 alkoxy group and even more preferably a C4-6 alkoxy group.

In formula (I), $R^{11}$ is preferably a cyano group, halogen atom, C1-6 haloalkyl group, C2-6 haloalkenyl group or C2-6 haloalkynyl group.

In formula (I), $R^{20}$ is preferably a cyano group, halogen atom, C1-6 haloalkyl group, C2-6 haloalkenyl group or C2-6 haloalkynyl group.

In formula (I), $R^{21}$ is preferably a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group.

In addition, $R^{10}$ or $R^{11}$ on $Cy^1$ may respectively or mutually, or together with an atom that bonds on $Cy^1$, form a ring, and $R^{20}$ or $R^{21}$ on $Cy^2$ may respectively or mutually, or with an atom that bonds on $Cy^2$, form a ring.

Examples of rings that may be formed include aromatic hydrocarbon rings such as a benzene ring; C5-7 cycloalkene rings such as a cyclopentene ring, cyclohexene ring or cycloheptene ring; aromatic 5-7-membered hetero rings such as a furan ring, thiophene ring, pyrrole ring, imidazole ring, pyrazole ring, thiazole ring, oxazole ring, isoxazole ring, pyridine ring, pyrazine ring, pyrimidine ring, pyridazine ring, azepine ring or diazepine ring; and unsaturated 5-7-membered hetero rings such as a dihydro-2H-pyran ring, dihydro-2H-thiopyran ring or tetrahydropyridine ring.

These rings may also have substituents on the ring.

Examples of substituents include halogen atoms such as a fluorine atom, chlorine atom, bromine atom or iodine atom; C1-6 alkyl groups such as a methyl group, ethyl group, n-propyl group, i-propyl group, n-butyl group, s-butyl group, i-butyl group, t-butyl group, n-pentyl group or n-hexyl group; C3-6 cycloalkyl groups such as a cyclopropyl group, cyclobutyl group, cyclopentyl group or cyclohexyl group; C1-6 alkoxy groups such as a methoxy group, ethoxy group, n-propoxy group, i-propoxy group, n-butoxy group, s-butoxy group, i-butoxy group or t-butoxy group; hydroxyl group; and C1-6 haloalkyl groups such as a chloromethyl group, chloroethyl group, trifluoromethyl group, 1,2-dichloro-n-propyl group, 1-fluoro-n-butyl group or perfluoro-n-pentyl group.

In the cyclic amine compound according to the present invention, $Cy^1$ is preferably a phenyl group, $Cy^2$ is preferably a pyridin-2-yl group, $R^{1a}$ and $R^{2a}$ preferably together form a C1-2 alkylene group, vinylene group or group represented by the formula —$OCH_2$—, —$CH_2O$—, —$SCH_2$—, —$CH_2S$—, —$C(=O)CH_2$—, —$CH_2C(=O)$—, —$CH_2NR^6$— or —$NR^6CH_2$— (wherein, $R^6$ represents a hydrogen atom, unsubstituted or substituted C1-6 alkyl group, unsubstituted or substituted C1-7 acyl group, or unsubstituted or substituted C1-6 alkoxycarbonyl group), and $R^{1b}$, $R^{2b}$, $R^{3a}$, $R^{3b}$, $R^{4a}$, $R^{4b}$ and $R^{5a}$ are preferably hydrogen atoms. Namely, the cyclic amine compound according to the present invention is preferably a cyclic amine compound represented by formula (II).

[Chemical Formula 6]

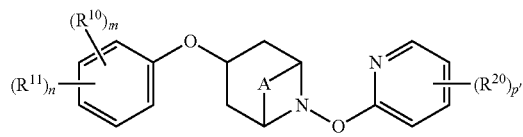

Furthermore, $R^{10}$, m, $R^{11}$, n and $R^{20}$ in formula (II) are the same as previously defined in formula (I). In formula (II), p' represents the number of $R^{20}$ and is an integer of any of 0 to 4, and when p' is 2 or more, $R^{20}$ may be mutually the same or different. In formula (II), A represents a C1-2 alkylene group, vinylene group, or group represented by the formula —$OCH_2$—, —$CH_2O$—, —$SCH_2$—, —$CH_2S$—, —C(=O)$CH_2$—, —$CH_2C$(=O)—, —$CH_2NR^6$ or —$NR^6CH_2$— (wherein, $R^6$ represents a hydrogen atom, unsubstituted or substituted C1-6 alkyl group, unsubstituted or substituted C1-7 acyl group, or unsubstituted or substituted C1-6 alkoxycarbonyl group).

[Salts of Cyclic Amine Compound]

There are no particular limitations on salts of the cyclic amine compound according to the present invention provided they are agriculturally and horticulturally acceptable salts. Examples thereof include salts of an inorganic acid such as hydrochloric acid or sulfuric acid; salts of an organic acid such as acetic acid or lactic acid; salts of an alkaline metal such as lithium, sodium or potassium; salts of an alkaline earth metal such as calcium or magnesium; salts of a transition metal such as iron or copper; and salts of organic bases such as ammonia, triethylamine, tributylamine, pyridine or hydrazine. A salt of the cyclic amine compound according to the present invention can be obtained by a known method from a cyclic amine compound represented by formula (I) or formula (II).

[Production Method]

There are no particular limitations on the production method used to produce the cyclic amine compound according to the present invention or a salt thereof. A production method that uses as an intermediate the hydroxyamine compound according to the present invention to be subsequently described, or a salt thereof, is preferable.

Therefore, the following provides an explanation of a production method used to produce the cyclic amine compound according to the present invention, or a salt thereof, by using as an example a production method that goes through a compound represented by the following formula (3) as an intermediate.

[Chemical Formula 7]

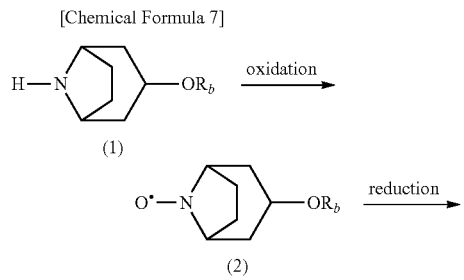

First, a secondary amine compound represented by formula (1) (to be referred to as "compound (1)") is prepared. An aminoxyl compound represented by formula (2) (to be referred to as "compound (2)") can then be synthesized by oxidizing the compound (1) with a suitable oxidizing agent. Specific examples of the oxidation reaction method include a method in which an oxidizing agent such as hydrogen peroxide, sodium hypochlorite or an organic oxidizing agent are allowed to act in a suitable solvent such as an anhydrous or hydrous alcohol such as methanol, ethanol, propanol or isopropanol, an ether such as dioxane or tetrahydrofuran (THF) or acetonitrile, and a method in which a tungstate-hydrogen peroxide urea complex is allowed to act. In addition, another example of a method that can be used consists of blowing a gas containing oxygen or active oxygen such as ozone into a reaction mixture.

Next, the aminoxyl group is converted to a hydroxyamino group by reducing compound (2) under suitable conditions. A hydroxyamine compound represented by formula (3) (to be referred to as "compound (3)") is formed by this reduction reaction.

Following the reduction reaction, a heteroaryl halide is reacted with compound (3) in the presence of a base. As a result, a heteroaryloxyamine compound represented by formula (4) can be obtained. This reaction is described in, for example, U.S. Pat. No. 5,286,865.

Furthermore, in the aforementioned formulas (1) to (4), $R_b$ represents an unsubstituted or substituted phenyl group, $R_a$ represents an unsubstituted or substituted heteroaryl group, and X represents a halogen atom.

In addition, compound (3) can also be obtained by, for example, the production method indicated below.

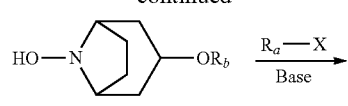

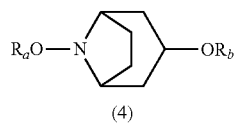

[Chemical Formula 8]

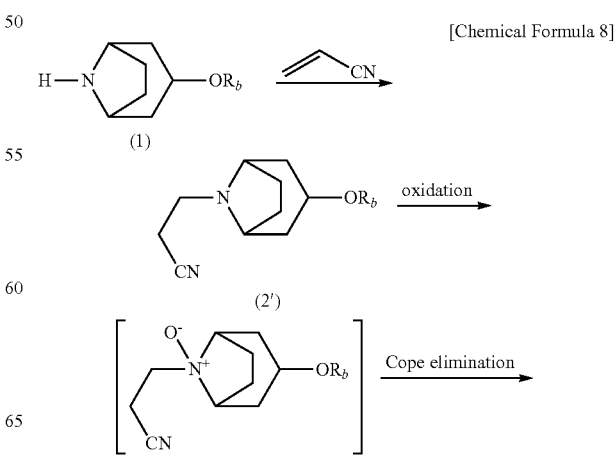

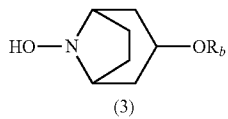

(3)

An alkylamino compound represented by formula (2') (to be referred to as "compound (2')") is obtained by N-alkylating the aforementioned compound (1) with acrylonitrile. Continuing, compound (3) can be obtained by oxidizing with a suitable oxidizing agent to obtain an N-oxide form within the reaction system and then subjecting this to a Cope elimination reaction. This reaction is described in, for example, Tetrahedron Letters, 48 (2007), pp. 1683-1686.

[Hydroxyamine Compound]

The hydroxyamine compound according to the present invention is a compound represented by formula (III). In addition, a salt of the hydroxyamine compound according to the present invention is a salt of a compound represented by formula (III). A compound represented by formula (III) or a salt thereof is preferable as a production intermediate of a compound represented by formula (I) or formula (II) or a salt thereof.

In formula (III), $Cy^1$, $R^{10}$, $R^{11}$, m, n, $R^{1a}$, $R^{1b}$, $R^{2a}$, $R^{2b}$, $R^{3a}$, $R^{3b}$, $R^{4a}$, $R^{4b}$ and $R^{5a}$ are the same as previously defined in formula (I).

In formula (III), $Cy^1$ is preferably a phenyl group, pyrazolyl group, thiadiazolyl group, pyridyl group, pyrimidinyl group or pyridazinyl group.

$R^{10}$ in formula (III) is preferably a C1-6 alkyl group, C1-6 alkoxy C1-6 alkyl group, C1-6 alkoxy C1-6 alkoxy C1-76 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group. Among these R10 is preferably a C1-6 alkoxy group and more preferably a C4-6 alkoxy group.

$R^{11}$ in formula (III) is preferably a cyano group, halogen atom, C1-6 haloalkyl group, C2-6 haloalkenyl group or C2-6 haloalkynyl group.

There are no particular limitations on the salt of the hydroxyamine compound according to the present invention provided it does not inhibit reaction with heteroaryl halide in the presence of base. Examples of salts include alkaline metal salts such as lithium salts, sodium salts or potassium salts. A salt of the hydroxyamine compound according to the present invention can be obtained by a known method from a hydroxyamine compound represented by formula (III).

Since the cyclic amine compound of the present invention, or salt thereof, demonstrates insecticidal action on adult insects, immature insects, larvae, insect eggs and the like, it can be used to control harmful organisms such as harmful insects present on agricultural crops, mites, ticks, sanitarily harmful insects, stored grain harmful insects, clothing harmful insects and household harmful insects. The cyclic amine compound of the present invention or salt thereof is useful as an active ingredient of an acaricide since it is particularly effective in controlling acari.

Examples of acari targeted for control are indicated below:

acari belonging to the Tetranychidae family, including *Brevipalpus lewisi, Brevipalpus obovatus, Brevipalpus phoenicis, Bryobia praetiosa, Bryobia rubrioculus, Dolichotetranychus floridanus, Eotetranychus boreus, Eotetranychus geniculatus, Eotetranychus pruni, Eotetranychus sexmanaculatus, Eotetranychus smithi, Eotetranychus uncatus, Oligonychus hondoensis, Oligonychus ilicis, Oligonychus karamatus, Oligonychus shinkajii, Panonychus citri, Panonychus mori, Panonychus ulmi, Tenuipalpus zhizhilashviliae, Tetranychus cinnabarinus, Tetranychus kanzawai, Tetranychus urticae, Tetranychus viennensis* or *Tuckerella pavoniformis;* acari belonging to the Eriophyidae family, such as *Acaphylla theavagrans, Aceria paradianthi, Aceria tulipae, Aculops lycopersici, Aculops pelekassi, Aculus fockeui, Aculus schlechtendali, Calacarus carinatus, Calepitrimerus vitis, Colomerus vitis, Epitrimerus pyri, Eriophes kuko* or *Eriophyes chibaensis;* acari belonging to the Astigmata family, such as *Acarus siro, Aleuroglyphus ovatus, Carpoglyphus lactis, Lardoglyphus konoi, Rhizoglyphus echinopus, Rhizoglyphus robini, Tyrophagus putrescentiae* or *Tyrophagus similis;* acari belonging to the Tarsonemidae family, such as *Phytonemus pallidus, Polyphagotarsonemus latus, Tarsonemus bilobatus* or *Tarsonemus waitei;* acari belonging to the Eupodidae family, such as *Penthaleus erythrocephalus* or *Penthaleus major*; and resistant acari having resistance to conventionally known acaricides. In addition, the cyclic amine compound of the present invention or salt thereof causes little chemical damage, demonstrates low levels of toxicity in fish and warm-blooded animals, and is a compound having a particularly high degree of safety.

[Acaricide]

The acaricide of the present invention contains as an active ingredient thereof at least one type selected from the group consisting of a cyclic amine compound represented by formula (I) or formula (II) or a salt thereof. In the acaricide of the present invention, one type of the cyclic amine compound represented by formula (I) or formula (II) or a salt thereof can be contained alone, or two or more types can be contained in combination.

In addition, although the acaricide of the present invention may contain only the cyclic amine compound represented by formula (I) or formula (II) of the present invention, or a salt thereof, it may also contain a carrier such as a solid carrier, liquid carrier or gaseous carrier. In addition, the acaricide of the present invention may have the cyclic amine compound represented by formula (I) or formula (II), or a salt thereof, impregnated in a base material such as a porous ceramic plate or non-woven fabric. Moreover, a surfactant or other adjunct may be added as necessary.

The acaricide according to the present invention can be formulated into a form able to be typically adopted by agricultural chemicals, namely in the form of a water-dispersible powder, granules, powder, emulsion, water soluble powder, suspension, granular water-dispersible powder, flowable preparation, aerosol, fog, heat transpiration agent, fumigant, poison bait or microcapsules.

Examples of additives and carriers used when formulating a solid preparation include vegetable powders such as soybean powder or flour, mineral fine powders such as diatomaceous earth, apatite, plaster, talc, bentonite, pyrophyllite or clay; and organic and inorganic compounds such as sodium benzoate, urea or sodium sulfate.

Examples of solvents used when formulating liquid preparations include petroleum fractions such as kerosene, xylene or solvent naphtha; cyclohexane, cyclohexanone, dimethylformamide, dimethylsulfoxide, alcohols, acetone, methyl isobutyl ketone, mineral oils, vegetable oils and water.

Examples of gaseous carriers used when formulating propellants include butane gas, LPG, dimethyl ether and carbon dioxide gas.

Examples of base materials of poison bait include bait components such as grain powder, vegetable oil, sugar or crystalline cellulose, antioxidants such as dimethylhydroxytoluene or nordihydroguaiaretic acid, preservatives such as dehydroacetic acid, accidental swallowing preventives for small children and pets such as cayenne pepper powder, insect-attracting fragrances such as cheese fragrance or onion fragrance.

A surfactant can be added in order to obtain a uniform and stable form during formulation. Examples of surfactants include nonionic surfactants such as polyoxyethylene alkyl ethers, polyoxyethylene higher fatty acid esters, polyoxyethylene sorbitan higher fatty acid esters or polyoxyethylene tristyryl phenyl ethers, sulfate esters of polyoxyethylene alkyl phenyl ethers, alkylnaphthalene sulfonates, polycarboxylates, lignin sulfonates, formaldehyde condensates of alkyl-naphthalene sulfonates and isobutylene-maleic anhydride copolymers.

In the case of using the acaricide of the present invention in agricultural applications, the content of the cyclic amine compound of the present invention or salt thereof in a preparation is preferably 0.01% by weight to 90% by weight and more preferably 0.05% by weight to 85% by weight.

An acaricide for agricultural use that is supplied in the form of a water-dispersible powder, emulsion, suspension, flowable preparation, water-soluble powder or granular water-dispersible powder can be prepared in the form of a solution, suspension or emulsion by diluting to a prescribed concentration with water and then sprayed onto plants or soil. In addition, an acaricide for agricultural use that is supplied in the form of a powder or granules can be sprayed directly onto plants or soil.

In addition, an acaricide for epidemic prevention that is supplied in the form of an emulsion, water-dispersible powder or flowable preparation and the like can be applied by diluting to a prescribed concentration with water. In addition, an acaricide for epidemic prevention that is supplied in the form of an oil solution, aerosol, fog, poison bait or acaricidal sheet can be used directly.

In the case of using the acaricide of the present invention to control animal parasitic acari of livestock such as cows or pigs and pets such as dogs or cats, the cyclic amine compound of the present invention can be used at a ratio of 0.01 mg to 1000 mg per 1 kg of host animal.

An acaricide for controlling animal parasitic acari can be applied using a known veterinary method. Examples of such methods include methods in which the acaricide is administered to an animal by a tablet, capsule, immersion liquid, food additive, suppository or injection (intramuscular, subcutaneous, intravenous or intraabdominal injection) when administered for the purpose of systemic control, methods in which an oily or aqueous liquid preparation is administered by spraying, pouring on or spotting on when administered for the purpose of non-systemic control, and methods in which the acaricide is mixed with a resin and the kneaded product is molded into a suitable shape such as that of a collar or ear tag which is then attached to the animal.

The acaricide of the present invention can be mixed or used in combination with fungicides, other insecticides or acaricides, nematocides, soil pesticides, plant regulators, synergists, fertilizers, soil improvers or animal feeds and the like.

The following lists typical examples of fungicides, other insecticides or acaricides, nematocides, soil pesticides and plant regulators able to be used by mixing with the compound of the present invention.

Fungicides:
1) benzimidazole-based: benomyl, carbendazim, fuberidazole, thiabendazole or methyl thiophanate;
2) dicarboxylmide-based fungicides: chlozolinate, iprodione, procymidone or vinclozolin;
3) DMI fungicides: imdazalil, oxpoconazole, pefurazoate, prochloraz, triflumizole, triforine, pyrifenox, fenarimol, nuarimol, azaconazole, bitertanol, bromconazole, cyproconazole, difenoconazole, diniconazole, epoxyconazole, fenbuconazole, fluquinconazole, flusilazole, flutriafol, hexaconazole, imibenconazole, ipuconazole, metconazole, myclobutanil, penconazole, propiconazole, prothioconazole, simeconazole, tebuconazole, tetraconazole, triadimefon, triadimenol, triticonazole, etaconazole or furconazole-cis;
4) phenylamide-based: benalaxyl, furalaxyl, metalaxyl, metalaxyl-M, oxadixyl or ofurace,
5) amine-based: aldimorph, dodemorph, fenpropimorph, tridemorph, fenpropidine, piperalin or spiroxamine;
6) phosphothiolate-based: EDDP, iprobenfos or pyrazophos;
7) dithiolane-based: isoprothiolane;
8) carboxamide-based: benodanil, boscalid, carboxin, fenfuran, flutolanil, furametpyr, mepronil, oxycarboxin, penthiopyrad or thifluzamide;
9) hydroxy(2-amino)pyrimidine-based: bupirimate, dimethirimol or ethirimol;
10) AP fungicides (anilinopyrimidines-based): cyprodinil, mepanipyrim or pyrimethanil;
11) N-phenylcarbamate-based: diethofencarb;
12) QoI fungicides (Qo inhibitor-based): azoxystrobin, picoxystrobin, pyraclostrobin, kresoxim-methyl, trifloxystrobin, dimoxystrobin, metominostrobin, orysastrobin, famoxadone, fluoxastrobin, fenamidone or metominofen;
13) PP fungicides (phenylpyrrole-based): fenpiconil or fludioxonil;
14) quinoline-based: quinoxyfen;
15) AH fungicides (aromatic hydrocarbon-based): biphenyl, chloroneb, dichloran, quintozene, tecnazene or tolclofos-methyl;
16) MBI-R-based: fthalide, pyroquilon or tricyclazole;
17) MBI-D-based: carpropamid, diclocymet or fenoxanil;
18) SBI agents: fenhexamid, pyributicarb or terbinafine;
19) phenylureas: pencycuron;
20) Qil fungicides (Qi inhibitors): cyazofamid;
21) benzamide-based: zoxamide;
22) enopyranurone-based: blasticidin or mildiomycin;
23) hexopyranosyl-based: kasugamycin;
24) glucopyranosyl-based: streptomycin or validamycin;
25) cyanoacetoamide-based: cymoxanil;
26) carbamate-based: idocarb, propamocarb, prothiocarb or polycarbamate;
27) uncoupling agents: binapacryl, dinocap, ferimzone or fluazinam;
28) organic tin compounds: triphenyltin acetate, triphenyltin chloride or triphenyltin hydroxide;
29) phosphate esters: phosphonic acid, tolclofos-methyl or fosetyl;
30) phthalamide-based: tecloftalam;
31) benzotriazine-based: triazoxide;
32) benzene sulfonamide-based: flusulfamide;
33) pyridazinones: diclomezine;

34) CAA fungicides (carbonic acid amide-based): dimethomorph, flumorph, benthiavalicarb, iprovalicarb or mandipropamide;

35) tetracyclines: oxytetracycline;

36) thiocarbamate-based: methasulfocarb; and, 37) other compounds: etridiazole, polyoxins, oxolinic acid, hydroxyisoxazole, octinoline, silthiofam, diflumetorim, acibenzolar-s-methyl, probenazole, tiadinil, ethaboxam, cyflufenamid, proquinazid, metrafenone, fluopicolide, cupric hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine acetate, iminoctadine dodecylbenzene sulfonate, anilazine, dithianon, chloropicrin, dazomet, metam sodium salt, chinomethionat, cyprofuram, silthiofam, agrobacterium or fluoroimide.

Examples of insecticides, acaricides, nematocides and soil pesticides include:

1) organic (thio)phosphate-based: such as acephate, azamethiphos, azinphos-methyl, chlorpyriphos, chlorpyriphos-methyl, chlorfenvinphos, diazinon, dichlorvos, dicrotophos, dimethoate, disulfoton, ethion, EPN, fenamiphos, fenitrothion, fenthion, isoxathion, malathion, methamidophos, methidathion, methyl parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprofos, tetrachlorvinphos, terbufos, triazophos, trichlorfon, fosthiazate, phosphocarb, cadusafos, disulfoton, demeton-s-methyl, BRP, CYAP, ethoprophos, quinalphos, dimethylvinphos, vamidothion or pyraclofos;

2) carbamate-based: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridafenthion, furathiocarb or XMC;

3) pyrethroid-based: allethrin, bifenthrin, cyfluthrin, cyhalothrin, cyphenothrin, cypermethrin, alphacypermethrin, betacypermethrin, zetacypermethrin, deltamethrin, esfenvalerate, etofenprox, fenpropathrin, fenvalerate, imiprothrin, lambdacyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, acrinathrin, cycloprothrin, halfenprox or flucythrinate;

4) growth regulators:

a) chitin synthesis inhibitors: chlorfluazuron, diflubenzuron, flucycloxuron, flufenoxuron, hexaflumuron, lufenuron, novaluron, teflubenzuron, triflumuron, bistrifluoron, nobifumuron, buprofezin, diofenolan, hexythiazox, etoxazole or clofentezine;

b) ecdysone antagonists: halofenozide, methoxyfenozide, tebufenozide, azadirachtin or chromafenozide;

c) juvenile hormone-like substances: pyriproxyfen, methoprene or fenoxycarb;

d) lipid biosynthesis inhibitors: spirodiclofen, spiromesifen or spirotetramat;

5) nicotine receptor agonist/antagonist compounds: acetamiprid, clothianidine, dinotefuran, imidacloprid, nitenpyram, thiacloprid or thiamethoxam;

6) GABA antagonist compounds: acetochlor, endosulfan, ethiprole, fipronil, vaniliprole, pyrafluprole or pyriprole;

7) macrocyclic lactone insecticides: abamectin, emamectin, milbemectin, lepimectin, spinosad or ivermectin;

8) METI I compounds: fenazaquin, pyridaben, tebufenpyrad, tolfenpyrad or flufenerim;

9) METI II and III compounds: acequinocyl, fluacyprim or hydramethylnon;

10) uncoupling agent compounds: chlorfenapyr;

11) oxidative phosphorylation inhibitor compounds: cyhexitin, diafenthiuron, fenbutatin oxide or propargite;

12) molting disruption compounds: cyromazine;

13) mixed function oxidase inhibitor compounds: piperonyl butoxide;

14) sodium channel blocker compounds: indoxacarb or metaflumizone;

15) microbial pesticides: BT agents, insect pathogen viral agents, insect pathogen fungal agents or nematode pathogen fungal agents; and 16) other compounds: benclothiaz, bifenazate, cartap, flonicamid, pyradalyl, pymetrozine, sulfur, thiocyclam, flubendiamide, cyenopyrafen, flupyrazofos, cyflumetofen, amidoflumet, bensultap, dicofol, tetradifon, fenpyroximate, amitraz, chlordimeform, pymetrozine, pyrimidifen, 1,3-dichloropropene, clofentenzine, fluacrypyrim, rotenone, DCIP, phenisobromolate, benzomate, methaldehyde, chlorantraniliprole, spinetoram or pyrifluquinzaon.

Examples of plant growth regulators include:

abscisic acid, indole butyric acid, uniconazole, ethychlozate, ethephon, cloxyfonac, chlormequat, chlorella extract, calcium peroxide, cyanamide, dichlorprop, gibberellin, daminozide, decyl alcohol, trinexapac-ethyl, mepiquat-chloride, paclobutrazol, paraffin wax, piperonyl butoxide, pyraflufen ethyl, flurprimidol, prohydrojasmon, prohexadione-calcium, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene and aviglycine hydrochloride.

EXAMPLES

The following provides a more detailed explanation of the present invention by indicating examples thereof. However, the scope of the present invention is not limited by the following examples.

Example 1

Production of 3-endo-[2-cyclopropylmethoxy-4-(trifluoro-methyl)phenoxy]-8-hydroxy-8-azabicyclo [3.2.1]octane (Compound (2a))

[Chemical Formula 9]

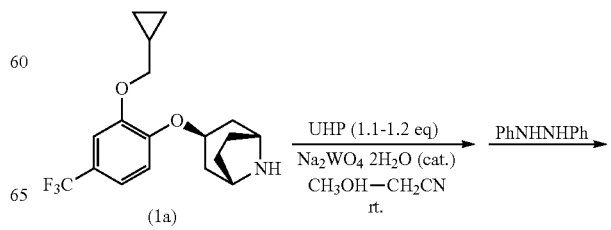

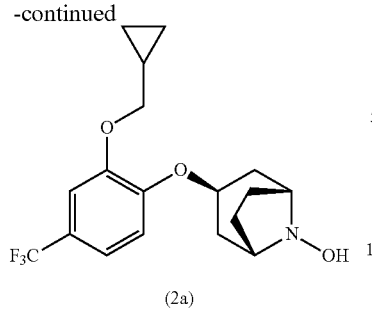

(2a)

The raw material, 3-endo-[2-cyclopropyl-methoxy-4-(trifluoromethyl)phenoxy]-8-azabicyclo[3.2.1]octane (Compound (1a)) was synthesized by the method described in International Publication No. WO 2005/095380.

Sodium tungstate (0.5 g) was added to a methanol solution (40 ml) of Compound (1a) (5 g) at room temperature followed by stirring for 30 minutes. After the mixture was cooled to 0° C., urea-hydrogen peroxide (UHP, 1.55 g) was added followed by stirring for 45 minutes at 0° C. and further stirring for 2 hours after warming to room temperature. During that time, methylene chloride (50 ml) was added. The mixture was then allowed to return to room temperature followed by the addition of 1,2-diphenylhydrazine (3 g) and stirring for 1 hour at room temperature. Water was then added to the mixture followed by extraction with methylene chloride, drying the organic layer with anhydrous potassium carbonate and concentrating. The residue was purified by silica gel column chromatography to obtain Compound (2a) (0.788 g).

Example 2

Production of 3-endo-[2-cyclopropylmethoxy-4-(trifluoro-methyl)phenoxy]-8-hydroxy-8-azabicyclo[3.2.1]octane (Compound (2a))

[Chemical Formula 10]

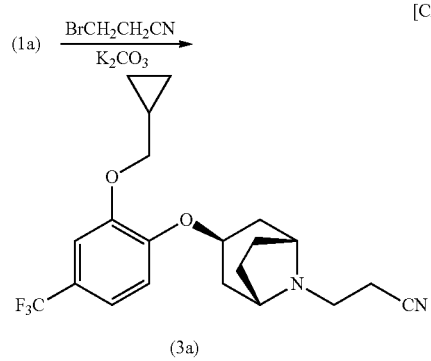

3-bromopropionitrile (1 g), anhydrous potassium carbonate (1.15 g) and potassium iodide (0.2 g) were added to an N,N-dimethylformamide solution (20 ml) of Compound (1a) (2 g) followed by stirring for 3 hours at 90° C. After cooling the mixture to room temperature, the mixture was poured into water and extracted with ethyl acetate. The organic layer was washed with water, dried with anhydrous magnesium sulfate and filtered followed by concentrating under reduced pressure. The residue was purified by silica gel column chromatography (chloroform:methanol=8:1) to obtain Compound (3a) (1.5 g).

Meta-chlorobenzoic acid (0.97 g) and anhydrous potassium carbonate (0.76 g) were added to a methylene chloride solution (30 ml) of Compound (3a) (1.45 g) while cooling with ice. After stirring the mixture overnight at room temperature, the mixture was filtered through anhydrous magnesium sulfate followed by concentrating the solvent-under reduced pressure. The residue was purified by silica gel column chromatography (hexane:ethyl acetate=1:1 followed by chloroform:methanol=10:1) to obtain Compound (2a) (0.9 g) in the form of a colorless solid.

$^1$H-NMR (CDCl$_3$, δppm): 7.13 (d, 1H), 7.04 (s, 1H), 6.78 (d, 1H), 4.44 (br, 1H), 3.85 (d, 2H), 3.56 (brs, 2H), 2.26-2.22 (m, 2H), 2.14-2.12 (m, 6H), 1.34-1.26 (m, 1H), 0.68-0.59 (m, 2H), 0.37 (q, 2H)

Example 3

Production of 3-endo-[2-cyclopropylmethoxy-4-(trifluoro-methyl)phenoxy]-8-[5-(trifluoromethyl)-2-pyridyloxy]-8-azabicyclo[3.2.1]octane (Compound 8)

[Chemical Formula 11]

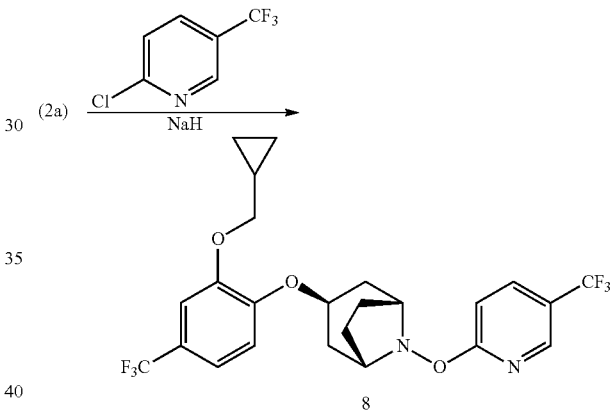

Sodium hydride (purity: 55%, 0.11 g) was added to an N,N-dimethylformamide solution (5 ml) of Compound (2a) (0.81 g) while cooling with ice followed by stirring for 10 minutes. 2-chloro-5-trifluoromethylpyridine (0.62 g) were added to the mixture at 10° C. or lower followed by slowly warming to room temperature and stirring for 90 minutes. This was then poured into water and extracted with ethyl acetate. The organic phase was washed with water, dried with anhydrous magnesium sulfate and filtered followed by concentrating under reduced pressure. The residue was purified by silica gel column chromatography (hexane:ethyl acetate=6:1) to obtain the target compound (0.75 g) in the form of a colorless solid.

Melting point (mp): 116° C.-123° C.

$^1$H-NMR (CDCl$_3$, δppm): 8.48 (s, 1H), 7.86 (dd, 1H), 7.37 (d, 1H), 7.15 (d, 1H), 7.05 (s, 1H), 6.82 (d, 1H), 4.55 (brt, 1H), 3.87 (d, 2H), 3.77 (brs, 2H), 2.43-2.22 (m, 8H), 1.34-1.24 (m, 1H), 0.69-0.62 (m, 2H), 0.40-0.35 (m, 2H)

Cyclic amine compounds according to the present invention able to be obtained according to methods similar to the aforementioned production methods are shown in Tables (1) to (12).

Furthermore, $(R^{10})_m$, $(R^{11})_n$, $(R^{21})_r$ and $(R^{20})_p$ in Tables (1) and (2) indicate respective substituents of the cyclic amine compound represented by formula (IIa).

$(R^{10})_m$, $(R^{11})_n$, $R^{1a}$, $R^{3a}$, $(R^{21})_r$ and $(R^{20})_p$ in Table (3) indicate respective substituents of the cyclic amine compound represented by formula (Ia).

$(R^{10})_m$, $(R^{11})_n$, $R^{1a}$, $R^{3a}$, $(R^{21})_r$ and $(R^{20})_p$ in Table (4) indicate respective substituents of the cyclic amine compound represented by formula (Ib).

$(R^{10})_m$, $(R^{11})_n$, $R^{1a}$, $R^{3a}$, $(R^{21})_r$ and $(R^{20})_p$ in Table (5) indicate respective substituents of the cyclic amine compound represented by formula (Ic).

$(R^{10})_m$, $(R^{11})_n$, $R^{1a}$, $R^{3a}$, $(R^{21})_r$ and $(R^{20})_p$ in Table (6) indicate respective substituents of the cyclic amine compound represented by formula (Id).

$(R^{10})_m$, $(R^{11})_n$, $R^{1a}$, $R^{3a}$, $(R^{21})_r$ and $(R^{20})_p$ in Table (7) indicate respective substituents of the cyclic amine compound represented by formula (Ie).

$(R^{10})_m$, $(R^{11})_n$, $(R^{21})_r$ and $Cy^2$-$(R^{20})_p$ in Table (8) indicate respective substituents of the cyclic amine compound represented by formula (If).

$(R^{10})_m$, $(R^{11})_n$, $(R^{21})_r$ and $Cy^2$-$(R^{20})_p$ in Table (9) indicate respective substituents of the cyclic amine compound represented by formula (Ig).

$(R^{10})_m$, $(R^{11})_n$, $(R^{21})_r$, $Cy^1$, $Cy^2$ and $(R^{20})_p$ in Table (10) indicate respective substituents of the cyclic amine compound represented by formula (Ih).

$(R^{10})_m$, $(R^{11})_n$, $(R^{21})_r$, $Cy^1$, $Cy^2$ and $(R^{20})_p$ in Table (11) indicate respective substituents of the cyclic amine compound represented by formula (Ii).

$(R^{10})_m$, $(R^{11})_n$, $(R^{21})_r$, $Cy^1$, $Cy^2$ and $(R^{20})_p$ in Table (12) indicate respective substituents of the cyclic amine compound represented by formula (Ij).

Furthermore, in Tables (1) to (12), numerical values shown in front of substituents indicate the substitution site. In addition, Et represents an ethyl group, $^n$Pr an n-propyl group, $^i$Pr an i-propyl group, $^c$Pr a cyclopropyl group, $^n$Bu an n-butyl group, $^i$Bu an i-butyl group, $^s$Bu an s-butyl group, $^t$Bu a t-butyl group, $^n$Pen an n-pentyl group, $^i$Pen an i-pentyl group, $^c$Pen a cyclopentyl group, $^n$Hex an n-hexyl group, $^c$Hex a cyclohexyl group, Ac an acetyl group, Ph a phenyl group and Bn a benzyl group.

TABLE 1

(IIa)

| Compound No. | $(R^{10})_m$ | $(R^{11})_n$ | $(R^{20})_p$ | $(R^{21})_r$ |
|---|---|---|---|---|
| 1 | 2-(OEt) | 4-CF$_3$ | 5-CF$_3$ | — |
| 2 | 2-(O$^n$Bu) | 4-CF$_3$ | 5-CF$_3$ | — |
| 3 | 2-(OCH$_2$$^i$Pr) | 4-CF$_3$ | 5-CF$_3$ | — |
| 4 | 2-(O$^s$Bu) | 4-CF$_3$ | 5-CF$_3$ | — |
| 5 | 2-(O$^t$Bu) | 4-CF$_3$ | 5-CF$_3$ | — |
| 6 | 2-(O$^n$Pen) | 4-CF$_3$ | 5-CF$_3$ | — |
| 7 | 2-(O$^n$Hex) | 4-CF$_3$ | 5-CF$_3$ | — |
| 8 | 2-(OCH$_2$$^c$Pr) | 4-CF$_3$ | 5-CF$_3$ | — |
| 9 | 2-(OCH$_2$$^c$Bu) | 4-CF$_3$ | 5-CF$_3$ | — |
| 10 | 2-(OCH$_2$$^c$Pen) | 4-CF$_3$ | 5-CF$_3$ | — |
| 11 | 2-(OCH$_2$$^c$Hex) | 4-CF$_3$ | 5-CF$_3$ | — |
| 12 | 2-(OCH$_2$CH$_2$$^c$Pr) | 4-CF$_3$ | 5-CF$_3$ | — |
| 13 | 2-(OCH$_2$CH$_2$$^c$Bu) | 4-CF$_3$ | 5-CF$_3$ | — |
| 14 | 2-(CH$_2$OCH$_3$) | 4-CF$_3$ | 5-CF$_3$ | — |
| 15 | 2-(CH$_2$OC$_2$H$_5$) | 4-CF$_3$ | 5-CF$_3$ | — |
| 16 | 2-(CH(OCH$_3$)CH$_3$) | 4-CF$_3$ | 5-CF$_3$ | — |
| 17 | 2-(C$_2$H$_4$OCH$_3$) | 4-CF$_3$ | 5-CF$_3$ | — |
| 18 | 2-(CH$_2$OCH$_2$CH(CH$_3$)CH$_3$) | 4-CF$_3$ | 5-CF$_3$ | — |
| 19 | 2-(OCH$_2$OCH$_3$) | 4-CF$_3$ | 5-CF$_3$ | — |
| 20 | 2-(OCH(OCH$_3$)CH$_3$) | 4-CF$_3$ | 5-CF$_3$ | — |
| 21 | 2-(OC$_2$H$_4$OCH$_3$) | 4-CF3 | 5-CF$_3$ | — |
| 22 | 2-(OCH$_2$CH(OCH$_3$)CH$_3$) | 4-CF3 | 5-CF$_3$ | — |
| 23 | 2-(OCH$_2$OC$_2$H$_5$) | 4-CF$_3$ | 5-CF$_3$ | — |
| 24 | 2-(OCH(OC$_2$H$_5$)CH$_3$) | 4-CF$_3$ | 5-CF$_3$ | — |
| 25 | 2-(OC$_2$H$_4$OC$_2$H$_5$) | 4-CF$_3$ | 5-CF$_3$ | — |
| 26 | 2-(CH$_2$OCH$_2$OCH$_3$) | 4-CF$_3$ | 5-CF$_3$ | — |
| 27 | 2-(CH$_2$OCH(OCH$_3$)CH$_3$) | 4-CF$_3$ | 5-CF$_3$ | — |
| 28 | 2-(CH$_2$OC$_2$H$_4$OCH$_3$) | 4-CF$_3$ | 5-CF$_3$ | — |
| 29 | 2-(C$_2$H$_4$OCH(OCH$_3$)CH$_3$) | 4-CF$_3$ | 5-CF$_3$ | — |
| 30 | 2-(CO$_2$CH=CH$_2$) | 4-CF$_3$ | 5-CF$_3$ | — |
| 31 | 2-(OCH$_2$CH(CH$_3$)CH=CH$_2$) | 4-CF$_3$ | 5-CF$_3$ | — |
| 32 | 2-(CO$_2$CH=C(CH$_3$)CH$_3$) | 4-CF$_3$ | 5-CF$_3$ | — |
| 33 | 2-(CO$_2$C≡CH) | 4-CF$_3$ | 5-CF$_3$ | — |
| 34 | 2-(CO$_2$CH$_2$C≡CH) | 4-CF$_3$ | 5-CF$_3$ | — |
| 35 | 2-(CO$_2$C(CH$_3$)C≡CH) | 4-CF$_3$ | 5-CF$_3$ | — |
| 36 | 2-(O—N=CH$_2$) | 4-CF$_3$ | 5-CF$_3$ | — |
| 37 | 2-(O—N=CHCH$_3$) | 4-CF$_3$ | 5-CF$_3$ | — |
| 38 | 2-(O—N=C(CH$_3$)$_2$) | 4-CF$_3$ | 5-CF$_3$ | — |
| 39 | 2-(O—N=CHEt) | 4-CF$_3$ | 5-CF$_3$ | — |
| 40 | 2-(O—N=CH(CH$_3$)Et) | 4-CF$_3$ | 5-CF$_3$ | — |
| 41 | 2-(OEt) | 4-CF$_3$ | 5-CN | — |
| 42 | 2-(O$^n$Bu) | 4-CF$_3$ | 5-CN | — |
| 43 | 2-(OCH$_2$$^i$Pr) | 4-CF$_3$ | 5-CN | — |
| 44 | 2-(O$^s$Bu) | 4-CF$_3$ | 5-CN | — |
| 45 | 2-(O$^t$Bu) | 4-CF$_3$ | 5-CN | — |
| 46 | 2-(O$^n$Pen) | 4-CF$_3$ | 5-CN | — |
| 47 | 2-(O$^n$Hex) | 4-CF$_3$ | 5-CN | — |
| 48 | 2-(OCH$_2$$^c$Pr) | 4-CF$_3$ | 5-CN | — |
| 49 | 2-(OCH$_2$$^c$Bu) | 4-CF$_3$ | 5-CN | — |
| 50 | 2-(OCH$_2$$^c$Pen) | 4-CF$_3$ | 5-CN | — |
| 51 | 2-(OCH$_2$$^c$Hex) | 4-CF$_3$ | 5-CN | — |
| 52 | 2-(OCH$_2$CH$_2$$^c$Pr) | 4-CF$_3$ | 5-CN | — |
| 53 | 2-(OCH$_2$CH$_2$$^c$Bu) | 4-CF$_3$ | 5-CN | — |
| 54 | 2-(CH$_2$OCH$_3$) | 4-CF$_3$ | 5-CN | — |
| 55 | 2-(CH$_2$OC$_2$H$_5$) | 4-CF$_3$ | 5-CN | — |
| 56 | 2-(CH(OCH$_3$)CH$_3$) | 4-CF$_3$ | 5-CN | — |
| 57 | 2-(C$_2$H$_4$OCH$_3$) | 4-CF$_3$ | 5-CN | — |
| 58 | 2-(CH$_2$OCH$_2$CH(CH$_3$)CH$_3$) | 4-CF$_3$ | 5-CN | — |
| 59 | 2-(OCH$_2$OCH$_3$) | 4-CF$_3$ | 5-CN | — |
| 60 | 2-(OCH(OCH$_3$)CH$_3$) | 4-CF$_3$ | 5-CN | — |
| 61 | 2-(OC$_2$H$_4$OCH$_3$) | 4-CF$_3$ | 5-CN | — |
| 62 | 2-(OCH$_2$CH(OCH$_3$)CH$_3$) | 4-CF$_3$ | 5-CN | — |
| 63 | 2-(OCH$_2$OC$_2$H$_5$) | 4-CF$_3$ | 5-CN | — |
| 64 | 2-(OCH(OC$_2$H$_5$)CH$_3$) | 4-CF$_3$ | 5-CN | — |
| 65 | 2-(OC$_2$H$_4$OC$_2$H$_5$) | 4-CF$_3$ | 5-CN | — |
| 66 | 2-(CH$_2$OCH$_2$OCH$_3$) | 4-CF$_3$ | 5-CN | — |
| 67 | 2-(CH$_2$OCH(OCH$_3$)CH$_3$) | 4-CF$_3$ | 5-CN | — |
| 68 | 2-(CH$_2$OC$_2$H$_4$OCH$_3$) | 4-CF$_3$ | 5-CN | — |
| 69 | 2-(C$_2$H$_4$OCH(OCH$_3$)CH$_3$) | 4-CF$_3$ | 5-CN | — |
| 70 | 2-(CO$_2$CH=CH$_2$) | 4-CF$_3$ | 5-CN | — |
| 71 | 2-(CO$_2$CH(CH$_3$)CH=CH$_2$) | 4-CF$_3$ | 5-CN | — |
| 72 | 2-(CO$_2$CH=C(CH$_3$)CH$_3$) | 4-CF$_3$ | 5-CN | — |
| 73 | 2-(CO$_2$C≡CH) | 4-CF$_3$ | 5-CN | — |
| 74 | 2-(CO$_2$CH$_2$C≡CH) | 4-CF$_3$ | 5-CN | — |
| 75 | 2-(CO$_2$C(CH$_3$)C≡CH) | 4-CF$_3$ | 5-CN | — |
| 76 | 2-(O—N=CH$_2$) | 4-CF$_3$ | 5-CN | — |
| 77 | 2-(O—N=CHCH$_3$) | 4-CF$_3$ | 5-CN | — |
| 78 | 2-(O—N=C(CH$_3$)$_2$) | 4-CF$_3$ | 5-CN | — |
| 79 | 2-(O—N=CHEt) | 4-CF$_3$ | 5-CN | — |
| 80 | 2-(O—N=CH(CH$_3$)Et) | 4-CF$_3$ | 5-CN | — |
| 81 | — | — | — | — |
| 82 | 2-(NO$_2$) | 4-CF$_3$ | 5-CF$_3$ | — |
| 83 | 2-(NHCO$_2$$^i$Pr) | 4-CF$_3$ | 5-CF$_3$ | — |
| 84 | — | 2-Br, 4-CF$_3$ | 5-CF$_3$ | — |
| 85 | — | 2-F, 4-CF$_3$ | 5-CF$_3$ | — |
| 86 | — | 2-CN, 4-CF$_3$ | 5-CF$_3$ | — |

TABLE 1-continued

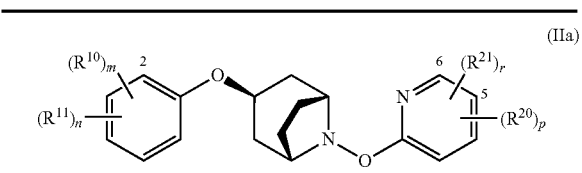

(IIa)

| Compound No. | $(R^{10})_m$ | $(R^{11})_n$ | $(R^{20})_p$ | $(R^{21})_r$ |
|---|---|---|---|---|
| 87 | — | 2-($CH_2Br$), 4-$CF_3$ | 5-$CF_3$ | — |
| 88 | 2-($OCH_2{}^cPr$) | 4-$CF_3$ | 5-$CF_3$, 6-Cl | — |
| 89 | — | 2-I, 4-$CF_3$ | 5-$CF_3$ | — |
| 90 | 2-(CH=$CH_2$) | 4-$CF_3$ | 5-$CF_3$ | — |
| 91 | 2-${}^cPr$ | 4-$CF_3$ | 5-$CF_3$ | — |
| 92 | 2-(oxazol-2-yl) | 4-$CF_3$ | 5-$CF_3$ | — |
| 93 | 2-(OPh) | 4-$CF_3$ | 5-$CF_3$ | — |
| 94 | 2-Ac | 4-$CF_3$ | 5-$CF_3$ | — |
| 95 | 2-(C≡$SiMe_3$) | 4-$CF_3$ | 5-$CF_3$ | — |
| 96 | 2-(C≡CH) | 4-$CF_3$ | 5-$CF_3$ | — |
| 97 | 2-(O[5-$CF_3$-pyridin-2-yl]) | 4-$CF_3$ | 5-$CF_3$ | — |
| 98 | 2-(NHAc) | 4-$CF_3$ | 5-$CF_3$ | — |
| 99 | 2-(NHCONH${}^iPr$) | 4-$CF_3$ | — | — |
| 100 | 2-(OCH($CH_3$)$CH_2$)-3 | 4-$CF_3$ | 5-$CF_3$ | — |
| 101 | 2-($OC_2H_4OCH_3$) | 4-$CF_3$ | 5-$CHF_2$ | — |
| 102 | 2-($OCH_2CH(OCH_3)CH_3$) | 4-$CF_3$ | 5-$CHF_2$ | — |
| 103 | 2-($OCH_2OC_2H_5$) | 4-$CF_3$ | 5-$CHF_2$ | — |
| 104 | 2-($OCH(OC_2H_5)CH_3$) | 4-$CF_3$ | 5-$CHF_2$ | — |
| 105 | 2-($OC_2H_4OC_2H_5$) | 4-$CF_3$ | 5-$CHF_2$ | — |
| 106 | 2-($CH_2OCH_2OCH_3$) | 4-$CF_3$ | 5-$CHF_2$ | — |
| 107 | 2-($CH_2OCH(OCH_3)CH_3$) | 4-$CF_3$ | 5-$CHF_2$ | — |
| 108 | 2-($CH_2OC_2H_4OCH_3$) | 4-$CF_3$ | 5-$CHF_2$ | — |
| 109 | 2-($C_2H_4OCH(OCH_3)CH_3$) | 4-$CF_3$ | 5-$CHF_2$ | — |
| 110 | 2-($CO_2CH=CH_2$) | 4-$CF_3$ | 5-$CHF_2$ | — |
| 111 | 2-($CO_2CH(CH_3)CH=CH_2$) | 4-$CF_3$ | 5-$CHF_2$ | — |
| 112 | 2-($CO_2CH=C(CH_3)CH_3$) | 4-$CF_3$ | 5-$CHF_2$ | — |
| 113 | 2-($CO_2C≡CH$) | 4-$CF_3$ | 5-$CHF_2$ | — |
| 114 | 2-($CO_2CH_2C≡CH$) | 4-$CF_3$ | 5-$CHF_2$ | — |
| 115 | 2-($CO_2C(CH_3)C≡CH$) | 4-$CF_3$ | 5-$CHF_2$ | — |
| 116 | 2-(O—N=$CH_2$) | 4-$CF_3$ | 5-$CHF_2$ | — |
| 117 | 2-(O—N=$CHCH_3$) | 4-$CF_3$ | 5-$CHF_2$ | — |
| 118 | 2-(O—N=$C(CH_3)_2$) | 4-$CF_3$ | 5-$CHF_2$ | — |
| 119 | 2-(O—N=CHEt) | 4-$CF_3$ | 5-$CHF_2$ | — |
| 120 | 2-(O—N=$CH(CH_3)Et$) | 4-$CF_3$ | 5-$CHF_2$ | — |
| 121 | 2-(OEt) | 4-$CHF_2$ | 5-$CF_3$ | — |
| 122 | 2-($O^nBu$) | 4-$CHF_2$ | 5-$CF_3$ | — |
| 123 | 2-($OCH_2{}^iPr$) | 4-$CHF_2$ | 5-$CF_3$ | — |
| 124 | 2-($O^sBu$) | 4-$CHF_2$ | 5-$CF_3$ | — |
| 125 | 2-($O^tBu$) | 4-$CHF_2$ | 5-$CF_3$ | — |
| 126 | 2-($O^nPen$) | 4-$CHF_2$ | 5-$CF_3$ | — |
| 127 | 2-($O^nHex$) | 4-$CHF_2$ | 5-$CF_3$ | — |
| 128 | 2-($OCH_2{}^cPr$) | 4-$CHF_2$ | 5-$CF_3$ | — |
| 129 | 2-($OCH_2{}^cBu$) | 4-$CHF_2$ | 5-$CF_3$ | — |
| 130 | 2-($OCH_2{}^cPen$) | 4-$CHF_2$ | 5-$CF_3$ | — |
| 131 | 2-($OCH_2{}^cHex$) | 4-$CHF_2$ | 5-$CF_3$ | — |
| 132 | 2-($OCH_2CH_2{}^cPr$) | 4-$CHF_2$ | 5-$CF_3$ | — |
| 133 | 2-($OCH_2CH_2{}^cBu$) | 4-$CHF_2$ | 5-$CF_3$ | — |
| 134 | 2-($CH_2OCH_3$) | 4-$CHF_2$ | 5-$CF_3$ | — |
| 135 | 2-($CH_2OC_2H_5$) | 4-$CHF_2$ | 5-$CF_3$ | — |
| 136 | 2-($CH(OCH_3)CH_3$) | 4-$CHF_2$ | 5-$CF_3$ | — |
| 137 | 2-($C_2H_4OCH_3$) | 4-$CHF_2$ | 5-$CF_3$ | — |
| 138 | 2-($CH_2OCH_2CH(CH_3)CH_3$) | 4-$CHF_2$ | 5-$CF_3$ | — |
| 139 | 2-($OCH_2OCH_3$) | 4-$CHF_2$ | 5-$CF_3$ | — |
| 140 | 2-($OCH(OCH_3)CH_3$) | 4-$CHF_2$ | 5-$CF_3$ | — |
| 141 | 2-($OC_2H_4OCH_3$) | 4-$CHF_2$ | 5-$CF_3$ | — |
| 142 | 2-($OCH_2CH(OCH_3)CH_3$) | 4-$CHF_2$ | 5-$CF_3$ | — |
| 143 | 2-($OCH_2OC_2H_5$) | 4-$CHF_2$ | 5-$CF_3$ | — |
| 144 | 2-($OCH(OC_2H_5)CH_3$) | 4-$CHF_2$ | 5-$CF_3$ | — |
| 145 | 2-($OC_2H_4OC_2H_5$) | 4-$CHF_2$ | 5-$CF_3$ | — |
| 146 | 2-($CH_2OCH_2OCH_3$) | 4-$CHF_2$ | 5-$CF_3$ | — |
| 147 | 2-($CH_2OCH(OCH_3)CH_3$) | 4-$CHF_2$ | 5-$CF_3$ | — |
| 148 | 2-($CH_2OC_2H_4OCH_3$) | 4-$CHF_2$ | 5-$CF_3$ | — |
| 149 | 2-($C_2H_4OCH(OCH_3)CH_3$) | 4-$CHF_2$ | 5-$CF_3$ | — |
| 150 | 2-($CO_2CH=CH_2$) | 4-$CHF_2$ | 5-$CF_3$ | — |
| 151 | 2-($CO_2CH(CH_3)CH=CH_2$) | 4-$CHF_2$ | 5-$CF_3$ | — |
| 152 | 2-($CO_2CH=C(CH_3)CH_3$) | 4-$CHF_2$ | 5-$CF_3$ | — |
| 153 | 2-($CO_2C≡CH$) | 4-$CHF_2$ | 5-$CF_3$ | — |
| 154 | 2-($CO_2CH_2C≡CH$) | 4-$CHF_2$ | 5-$CF_3$ | — |
| 155 | 2-($CO_2C(CH_3)C≡CH$) | 4-$CHF_2$ | 5-$CF_3$ | — |
| 156 | 2-(O—N=$CH_2$) | 4-$CHF_2$ | 5-$CF_3$ | — |
| 157 | 2-(O—N=$CHCH_3$) | 4-$CHF_2$ | 5-$CF_3$ | — |
| 158 | 2-(O—N=$C(CH_3)_2$) | 4-$CHF_2$ | 5-$CF_3$ | — |
| 159 | 2-(O—N=CHEt) | 4-$CHF_2$ | 5-$CF_3$ | — |
| 160 | 2-(O—N=$CH(CH_3)Et$) | 4-$CHF_2$ | 5-$CF_3$ | — |
| 161 | 2-(OEt) | 4-$CHF_2$ | 5-CN | — |
| 162 | 2-($O^nBu$) | 4-$CHF_2$ | 5-CN | — |
| 163 | 2-($OCH_2{}^iPr$) | 4-$CHF_2$ | 5-CN | — |
| 164 | 2-($O^sBu$) | 4-$CHF_2$ | 5-CN | — |
| 165 | 2-($O^tBu$) | 4-$CHF_2$ | 5-CN | — |
| 166 | 2-($O^nPen$) | 4-$CHF_2$ | 5-CN | — |
| 167 | 2-($O^nHex$) | 4-$CHF_2$ | 5-CN | — |
| 168 | 2-($OCH_2{}^cPr$) | 4-$CHF_2$ | 5-CN | — |
| 169 | 2-($OCH_2{}^cBu$) | 4-$CHF_2$ | 5-CN | — |
| 170 | 2-($OCH_2{}^cPen$) | 4-$CHF_2$ | 5-CN | — |
| 171 | 2-($OCH_2{}^cHex$) | 4-$CHF_2$ | 5-CN | — |
| 172 | 2-($OCH_2CH_2{}^cPr$) | 4-$CHF_2$ | 5-CN | — |
| 173 | 2-($OCH_2CH_2{}^cBu$) | 4-$CHF_2$ | 5-CN | — |
| 174 | 2-($CH_2OCH_3$) | 4-$CHF_2$ | 5-CN | — |
| 175 | 2-($CH_2OC_2H_5$) | 4-$CHF_2$ | 5-CN | — |
| 176 | 2-($CH(OCH_3)CH_3$) | 4-$CHF_2$ | 5-CN | — |
| 177 | 2-($C_2H_4OCH_3$) | 4-$CHF_2$ | 5-CN | — |
| 178 | 2-($CH_2OCH_2CH(CH_3)CH_3$) | 4-$CHF_2$ | 5-CN | — |
| 179 | 2-($OCH_2OCH_3$) | 4-$CHF_2$ | 5-CN | — |
| 180 | 2-($OCH(OCH_3)CH_3$) | 4-$CHF_2$ | 5-CN | — |
| 181 | 2-($OC_2H_4OCH_3$) | 4-$CHF_2$ | 5-CN | — |
| 182 | 2-($OCH_2CH(OCH_3)CH_3$) | 4-$CHF_2$ | 5-CN | — |
| 183 | 2-($OCH_2OC_2H_5$) | 4-$CHF_2$ | 5-CN | — |
| 184 | 2-($OCH(OC_2H_5)CH_3$) | 4-$CHF_2$ | 5-CN | — |
| 185 | 2-($OC_2H_4OC_2H_5$) | 4-$CHF_2$ | 5-CN | — |
| 186 | 2-($CH_2OCH_2OCH_3$) | 4-$CHF_2$ | 5-CN | — |
| 187 | 2-($CH_2OCH(OCH_3)CH_3$) | 4-$CHF_2$ | 5-CN | — |
| 188 | 2-($CH_2OC_2H_4OCH_3$) | 4-$CHF_2$ | 5-CN | — |
| 189 | 2-($C_2H_4OCH(OCH_3)CH_3$) | 4-$CHF_2$ | 5-CN | — |
| 190 | 2-($CO_2CH=CH_2$) | 4-$CHF_2$ | 5-CN | — |
| 191 | 2-($CO_2CH(CH_3)CH=CH_2$) | 4-$CHF_2$ | 5-CN | — |
| 192 | 2-($CO_2CH=C(CH_3)CH_3$) | 4-$CHF_2$ | 5-CN | — |
| 193 | 2-($CO_2C≡CH$) | 4-$CHF_2$ | 5-CN | — |
| 194 | 2-($CO_2CH_2C≡CH$) | 4-$CHF_2$ | 5-CN | — |
| 195 | 2-($CO_2C(CH_3)C≡CH$) | 4-$CHF_2$ | 5-CN | — |
| 196 | 2-(O—N=$CH_2$) | 4-$CHF_2$ | 5-CN | — |
| 197 | 2-(O—N=$CHCH_3$) | 4-$CHF_2$ | 5-CN | — |
| 198 | 2-(O—N=$C(CH_3)_2$) | 4-$CHF_2$ | 5-CN | — |
| 199 | 2-(O—N=CHEt) | 4-$CHF_2$ | 5-CN | — |
| 200 | 2-(O—N=$CH(CH_3)Et$) | 4-$CHF_2$ | 5-CN | — |
| 201 | 2-(OEt) | 4-$CHF_2$ | 5-$CHF_2$ | — |
| 202 | 2-($O^nBu$) | 4-$CHF_2$ | 5-$CHF_2$ | — |
| 203 | 2-($OCH_2{}^iPr$) | 4-$CHF_2$ | 5-$CHF_2$ | — |
| 204 | 2-($O^sBu$) | 4-$CHF_2$ | 5-$CHF_2$ | — |
| 205 | 2-($O^tBu$) | 4-$CHF_2$ | 5-$CHF_2$ | — |
| 206 | 2-($O^nPen$) | 4-$CHF_2$ | 5-$CHF_2$ | — |
| 207 | 2-($O^nHex$) | 4-$CHF_2$ | 5-$CHF_2$ | — |
| 208 | 2-($OCH_2{}^cPr$) | 4-$CHF_2$ | 5-$CHF_2$ | — |
| 209 | 2-($OCH_2{}^cBu$) | 4-$CHF_2$ | 5-$CHF_2$ | — |
| 210 | 2-($OCH_2{}^cPen$) | 4-$CHF_2$ | 5-$CHF_2$ | — |
| 211 | 2-($OCH_2{}^cHex$) | 4-$CHF_2$ | 5-$CHF_2$ | — |
| 212 | 2-($OCH_2CH_2{}^cPr$) | 4-$CHF_2$ | 5-$CHF_2$ | — |
| 213 | 2-($OCH_2CH_2{}^cBu$) | 4-$CHF_2$ | 5-$CHF_2$ | — |
| 214 | 2-($CH_2OCH_3$) | 4-$CHF_2$ | 5-$CHF_2$ | — |
| 215 | 2-($CH_2OC_2H_5$) | 4-$CHF_2$ | 5-$CHF_2$ | — |
| 216 | 2-($CH(OCH_3)CH_3$) | 4-$CHF_2$ | 5-$CHF_2$ | — |
| 217 | 2-($C_2H_4OCH_3$) | 4-$CHF_2$ | 5-$CHF_2$ | — |
| 218 | 2-($CH_2OCH_2CH(CH_3)CH_3$) | 4-$CHF_2$ | 5-$CHF_2$ | — |
| 219 | 2-($OCH_2OCH_3$) | 4-$CHF_2$ | 5-$CHF_2$ | — |
| 220 | 2-($OCH(OCH_3)CH_3$) | 4-$CHF_2$ | 5-$CHF_2$ | — |

TABLE 1-continued (IIa)

| Compound No. | $(R^{10})_m$ | $(R^{11})_n$ | $(R^{20})_p$ | $(R^{21})_r$ |
|---|---|---|---|---|
| 221 | 2-(OC$_2$H$_4$OCH$_3$) | 4-CHF$_2$ | 5-CHF$_2$ | — |
| 222 | 2-(OCH$_2$CH(OCH$_3$)CH$_3$) | 4-CHF$_2$ | 5-CHF$_2$ | — |
| 223 | 2-(OCH$_2$OC$_2$H$_5$) | 4-CHF$_2$ | 5-CHF$_2$ | — |
| 224 | 2-(OCH(OC$_2$H$_5$)CH$_3$) | 4-CHF$_2$ | 5-CHF$_2$ | — |
| 225 | 2-(OC$_2$H$_4$(OC$_2$H$_5$)) | 4-CHF$_2$ | 5-CHF$_2$ | — |
| 226 | 2-(CH$_2$OCH$_2$OCH$_3$) | 4-CHF$_2$ | 5-CHF$_2$ | — |
| 227 | 2-(CH$_2$OCH(OCH$_3$)CH$_3$) | 4-CHF$_2$ | 5-CHF$_2$ | — |
| 228 | 2-(CH$_2$OC$_2$H$_4$OCH$_3$) | 4-CHF$_2$ | 5-CHF$_2$ | — |
| 229 | 2-(C$_2$H$_4$OCH(OCH$_3$)CH$_3$) | 4-CHF$_2$ | 5-CHF$_2$ | — |
| 230 | 2-(CO$_2$CH=CH$_2$) | 4-CHF$_2$ | 5-CHF$_2$ | — |
| 231 | 2-(CO$_2$CH(CH$_3$)CH=CH$_2$) | 4-CHF$_2$ | 5-CHF$_2$ | — |
| 232 | 2-(CO$_2$CH=C(CH$_3$)CH$_3$) | 4-CHF$_2$ | 5-CHF$_2$ | — |
| 233 | 2-(CO$_2$C≡CH) | 4-CHF$_2$ | 5-CHF$_2$ | — |
| 234 | 2-(CO$_2$CH$_2$C≡CH) | 4-CHF$_2$ | 5-CHF$_2$ | — |
| 235 | 2-(CO$_2$C(CH$_3$)C≡CH) | 4-CHF$_2$ | 5-CHF$_2$ | — |
| 236 | 2-(O—N=CH$_2$) | 4-CHF$_2$ | 5-CHF$_2$ | — |
| 237 | 2-(O—N=CHCH$_3$) | 4-CHF$_2$ | 5-CHF$_2$ | — |
| 238 | 2-(O—N=C(CH$_3$)$_2$) | 4-CHF$_2$ | 5-CHF$_2$ | — |
| 239 | 2-(O—N=CHEt) | 4-CHF$_2$ | 5-CHF$_2$ | — |
| 240 | 2-(O—N=CH(CH$_3$)Et) | 4-CHF$_2$ | 5-CHF$_2$ | — |
| 241 | 2-(O$^i$Pen) | 4-CF$_3$ | 5-CF$_3$ | — |
| 242 | 2-(OCH$_2$CH(CH$_3$)CH$_3$) | 4-CF$_3$ | 5-CF$_3$ | — |
| 243 | 2-(CO$_2$CH(CH$_3$)CH$_2$CH$_3$) | 4-CF$_3$ | 5-CF$_3$ | — |
| 244 | 2-(OCH$_2$CF$_3$) | 4-CF$_3$ | 5-CF$_3$ | — |
| 245 | 2-(OCH$_2$CH$_2$CF$_3$) | 4-CF$_3$ | 5-CF$_3$ | — |
| 246 | 2-(OCH$_2$CHClCH$_3$) | 4-CF$_3$ | 5-CF$_3$ | — |
| 247 | 2-(OCH$_2$CF$_2$CH$_3$) | 4-CF$_3$ | 5-CF$_3$ | — |
| 248 | 2-(OCH$_2$CHFCH$_3$) | 4-CF$_3$ | 5-CF$_3$ | — |
| 249 | 2-(CO$_2{}^i$Pr) | 4-CF$_3$ | 5-CF$_3$ | — |
| 250 | 2-(CO$_2$CH$_2{}^i$Pr) | 4-CF$_3$ | 5-CF$_3$ | — |
| 251 | 2-OH | 4-CF$_3$ | 5-CF$_3$ | — |
| 252 | 2-(O$^n$Pr) | 4-CF$_3$ | — | 5-CH$_3$ |
| 253 | 2-(O$^n$Pr) | 4-CF$_3$ | 5-Br | — |

TABLE 2

(IIa)

| Compound No. | $(R^{10})_m$ | $(R^{11})_n$ | $(R^{20})_p$ | $(R^{21})_r$ |
|---|---|---|---|---|
| A-1 | 2-(OCH$_2{}^i$Pr) | 4-CF$_3$ | 4-CF$_3$ | — |
| A-2 | 2-(OCH$_2{}^c$Pr) | 4-CF$_3$ | 4-CF$_3$ | — |
| A-3 | 2-(O$^n$Bu) | 4-CF$_3$ | 4-CF$_3$ | — |
| A-4 | 2-(O$^s$Bu) | 4-CF$_3$ | 4-CF$_3$ | — |
| A-5 | 2-(O$^n$Pen) | 4-CF$_3$ | 4-CF$_3$ | — |
| A-6 | 2-(O$^n$Hex) | 4-CF$_3$ | 4-CF$_3$ | — |
| A-7 | 3-(OCH$_2{}^i$Pr) | 4-CF$_3$ | 5-CF$_3$ | — |
| A-8 | 3-(OCH$_2{}^c$Pr) | 4-CF$_3$ | 5-CF$_3$ | — |
| A-9 | 3-(O$^n$Bu) | 4-CF$_3$ | 5-CF$_3$ | — |
| A-10 | 3-(O$^n$Hex) | 4-CF$_3$ | 5-CF$_3$ | — |
| A-11 | 3-(CH$_2$OCH$_3$) | 4-CF$_3$ | 5-CF$_3$ | — |
| A-12 | 3-(CH$_2$OCH$_2$OCH$_3$) | 4-CF$_3$ | 5-CF$_3$ | — |
| A-13 | 3-(CH(OCH$_3$)CH$_3$) | 4-CF$_3$ | 5-CF$_3$ | — |
| A-14 | 3-(CH$_2$OCH(OCH$_3$)CH$_3$) | 4-CF$_3$ | 5-CF$_3$ | — |
| A-15 | 3-(CH$_2$OCH$_2$CH(CH$_3$)CH$_3$) | 4-CF$_3$ | 5-CF$_3$ | — |
| A-16 | 3-(OCH$_2$OCH$_3$) | 4-CF$_3$ | 5-CF$_3$ | — |
| A-17 | 3-(OCH(OCH$_3$)CH$_3$) | 4-CF$_3$ | 5-CF$_3$ | — |
| A-18 | 3-(CO$_2{}^i$Pr) | 4-CF$_3$ | 5-CF$_3$ | — |
| A-19 | 3-(CO$_2$CH=CH$_2$) | 4-CF$_3$ | 5-CF$_3$ | — |
| A-20 | 3-(O—N=C(CH$_3$)$_2$) | 4-CF$_3$ | 5-CF$_3$ | — |
| A-21 | 2-(OCH$_2{}^i$Pr) | 3-CF$_3$ | 5-CF$_3$ | — |
| A-22 | 2-(OCH$_2{}^c$Pr) | 3-CF$_3$ | 5-CF$_3$ | — |
| A-23 | 2-(O$^n$Bu) | 3-CF$_3$ | 5-CF$_3$ | — |
| A-24 | 2-(O$^n$Hex) | 3-CF$_3$ | 5-CF$_3$ | — |
| A-25 | 2-(CH$_2$OCH$_3$) | 3-CF$_3$ | 5-CF$_3$ | — |
| A-26 | 2-(CH$_2$OCH$_2$OCH$_3$) | 3-CF$_3$ | 5-CF$_3$ | — |
| A-27 | 2-(CH(OCH$_3$)CH$_3$) | 3-CF$_3$ | 5-CF$_3$ | — |
| A-28 | 2-(CH$_2$OCH(OCH$_3$)CH$_3$) | 3-CF$_3$ | 5-CF$_3$ | — |
| A-29 | 2-(CH$_2$OCH$_2$CH(CH$_3$)CH$_3$) | 3-CF$_3$ | 5-CF$_3$ | — |
| A-30 | 2-(OCH$_2$OCH$_3$) | 3-CF$_3$ | 5-CF$_3$ | — |
| A-31 | 2-(OCH(OCH$_3$)CH$_3$) | 3-CF$_3$ | 5-CF$_3$ | — |
| A-32 | 2-(CO$_2{}^i$Pr) | 3-CF$_3$ | 5-CF$_3$ | — |
| A-33 | 2-(CO$_2$CH=CH$_2$) | 3-CF$_3$ | 5-CF$_3$ | — |
| A-34 | 2-(O—N=C(CH$_3$)$_2$) | 3-CF$_3$ | 5-CF$_3$ | — |
| A-35 | 3-(OCH$_2{}^i$Pr) | 5-CF$_3$ | 5-CF$_3$ | — |
| A-36 | 3-(OCH$_2{}^c$Pr) | 5-CF$_3$ | 5-CF$_3$ | — |
| A-37 | 3-(O$^n$Bu) | 5-CF$_3$ | 5-CF$_3$ | — |
| A-38 | 3-(O$^n$Hex) | 5-CF$_3$ | 5-CF$_3$ | — |
| A-39 | 3-(NHCH$_2{}^c$Pr) | 5-CF$_3$ | 5-CF$_3$ | — |
| A-40 | 3-(N(CH$_3$)CH$_2{}^c$Pr) | 5-CF$_3$ | 5-CF$_3$ | — |
| A-41 | 2-(OCH$_2{}^i$Pr) | 4-CF$_3$ | 3-CF$_3$ | — |
| A-42 | 2-(OCH$_2{}^i$Pr) | 4-CF$_3$ | 4-CF$_3$ | — |
| A-43 | 2-(OCH$_2{}^i$Pr) | 4-CF$_3$ | 6-CF$_3$ | — |
| A-44 | 2-(O$^n$Pr) | 4-CF$_3$ | 6-CF$_3$ | — |
| A-45 | 2-(OCH$_2{}^i$Pr) | 5-CF$_3$ | 5-CF$_3$ | — |

TABLE 3

(Ia)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| B-1 | 2-(OCH$_2{}^i$Pr) | 4-CF$_3$ | H | H | 5-CF$_3$ | — |
| B-2 | 2-(OCH$_2{}^c$Pr) | 4-CF$_3$ | H | H | 5-CF$_3$ | — |
| B-3 | 2-(O$^n$Bu) | 4-CF$_3$ | H | H | 5-CF$_3$ | — |
| B-4 | 2-(O$^n$Hex) | 4-CF$_3$ | H | H | 5-CF$_3$ | — |
| B-5 | 2-(CH$_2$OCH$_3$) | 4-CF$_3$ | H | H | 5-CF$_3$ | — |
| B-6 | 2-(CH$_2$OCH$_2$OCH$_3$) | 4-CF$_3$ | H | H | 5-CF$_3$ | — |
| B-7 | 2-(CH(OCH$_3$)CH$_3$) | 4-CF$_3$ | H | H | 5-CF$_3$ | — |
| B-8 | 2-(CH$_2$OCH(OCH$_3$)CH$_3$) | 4-CF$_3$ | H | H | 5-CF$_3$ | — |
| B-9 | 2-(CH$_2$OCH$_2$CH(CH$_3$)CH$_3$) | 4-CF$_3$ | H | H | 5-CF$_3$ | — |
| B-10 | 2-(OCH$_2$OCH$_3$) | 4-CF$_3$ | H | H | 5-CF$_3$ | — |
| B-11 | 2-(OCH(OCH$_3$)CH$_3$) | 4-CF$_3$ | H | H | 5-CF$_3$ | — |
| B-12 | 2-(CO$_2{}^i$Pr) | 4-CF$_3$ | H | H | 5-CF$_3$ | — |
| B-13 | 2-(CH$_2$CH(OCH$_3$)$_2$) | 4-CF$_3$ | H | H | 5-CF$_3$ | — |
| B-14 | 2-([1,3]dioxolan-2-yl) | 4-CF$_3$ | H | H | 5-CF$_3$ | — |
| B-15 | 2-(NH$^n$Pr) | 4-CF$_3$ | H | H | 5-CF$_3$ | — |
| B-16 | 2-(NHCH$_2{}^i$Pr) | 4-CF$_3$ | H | H | 5-CF$_3$ | — |
| B-17 | 2-(OCH$_2{}^i$Pr) | 4-CF$_3$ | H | CH$_3$ | 5-CF$_3$ | — |
| B-18 | 2-(OCH$_2{}^c$Pr) | 4-CF$_3$ | H | CH$_3$ | 5-CF$_3$ | — |
| B-19 | 2-(O$^n$Bu) | 4-CF$_3$ | H | CH$_3$ | 5-CF$_3$ | — |
| B-20 | 2-(CH$_2$OCH$_3$) | 4-CF$_3$ | H | CH$_3$ | 5-CF$_3$ | — |
| B-21 | 2-(CH$_2$OCH(OCH$_3$)CH$_3$) | 4-CF$_3$ | H | CH$_3$ | 5-CF$_3$ | — |
| B-22 | 2-(OCH(OCH$_3$)CH$_3$) | 4-CF$_3$ | H | CH$_3$ | 5-CF$_3$ | — |
| B-23 | 2-(CO$_2{}^i$Pr) | 4-CF$_3$ | H | CH$_3$ | 5-CF$_3$ | — |
| B-24 | 2-(CH$_2$CH(OCH$_3$)$_2$) | 4-CF$_3$ | H | CH$_3$ | 5-CF$_3$ | — |
| B-25 | 2-([1,3]dioxolan-2-yl) | 4-CF$_3$ | H | CH$_3$ | 5-CF$_3$ | — |

TABLE 3-continued (Ia)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| B-26 | 2-(NH$^n$Pr) | 4-CF$_3$ | H | CH$_3$ | 5-CF$_3$ | — |
| B-27 | 2-(NHCH$_2^i$Pr) | 4-CF$_3$ | H | CH$_3$ | 5-CF$_3$ | — |
| B-28 | 2-(OCH$_2^i$Pr) | 4-CF$_3$ | CH$_3$ | H | 5-CF$_3$ | — |
| B-29 | 2-(OCH$_2^c$Pr) | 4-CF$_3$ | CH$_3$ | H | 5-CF$_3$ | — |
| B-30 | 2-(O$^n$Bu) | 4-CF$_3$ | CH$_3$ | H | 5-CF$_3$ | — |
| B-31 | 2-(CH$_2$OCH$_2$OCH$_3$) | 4-CF$_3$ | CH$_3$ | H | 5-CF$_3$ | — |
| B-32 | 2-(CH$_2$OCH(OCH$_3$)CH$_3$) | 4-CF$_3$ | CH$_3$ | H | 5-CF$_3$ | — |
| B-33 | 2-(OCH(OCH$_3$)CH$_3$) | 4-CF$_3$ | CH$_3$ | H | 5-CF$_3$ | — |
| B-34 | 2-(CO$_2^i$Pr) | 4-CF$_3$ | CH$_3$ | H | 5-CF$_3$ | — |
| B-35 | 2-(CH$_2$CH(OCH$_3$)$_2$) | 4-CF$_3$ | CH$_3$ | H | 5-CF$_3$ | — |
| B-36 | 2-([1,3]dioxolan-2-yl) | 4-CF$_3$ | CH$_3$ | H | 5-CF$_3$ | — |
| B-37 | 2-(NH$^n$Pr) | 4-CF$_3$ | CH$_3$ | H | 5-CF$_3$ | — |
| B-38 | 2-(NHCH$_2^i$Pr) | 4-CF$_3$ | CH$_3$ | H | 5-CF$_3$ | — |
| B-39 | 2-(OCH$_2^i$Pr) | 3-CF$_3$ | H | H | 5-CF$_3$ | — |
| B-40 | 2-(OCH$_2^c$Pr) | 3-CF$_3$ | H | H | 5-CF$_3$ | — |
| B-41 | 2-(O$^n$Bu) | 3-CF$_3$ | H | H | 5-CF$_3$ | — |
| B-42 | 2-(CH$_2$OCH$_2$OCH$_3$) | 3-CF$_3$ | H | H | 5-CF$_3$ | — |
| B-43 | 2-(CH$_2$OCH(OCH$_3$)CH$_3$) | 3-CF$_3$ | H | H | 5-CF$_3$ | — |
| B-44 | 2-(OCH(OCH$_3$)CH$_3$) | 3-CF$_3$ | H | H | 5-CF$_3$ | — |
| B-45 | 2-(CO$_2^i$Pr) | 3-CF$_3$ | H | H | 5-CF$_3$ | — |
| B-46 | 2-(CH$_2$CH(OCH$_3$)$_2$) | 3-CF$_3$ | H | H | 5-CF$_3$ | — |
| B-47 | 2-([1,3]dioxolan-2-yl) | 3-CF$_3$ | H | H | 5-CF$_3$ | — |
| B-48 | 2-(NH$^n$Pr) | 3-CF$_3$ | H | H | 5-CF$_3$ | — |
| B-49 | 2-(NHCH$_2^i$Pr) | 3-CF$_3$ | H | H | 5-CF$_3$ | — |
| B-50 | 2-(OCH$_2^i$Pr) | 3-CF$_3$ | H | CH$_3$ | 5-CF$_3$ | — |
| B-51 | 2-(OCH$_2^c$Pr) | 3-CF$_3$ | H | CH$_3$ | 5-CF$_3$ | — |
| B-52 | 2-(O$^n$Bu) | 3-CF$_3$ | H | CH$_3$ | 5-CF$_3$ | — |
| B-53 | 2-(CH$_2$OCH$_2$OCH$_3$) | 3-CF$_3$ | H | CH$_3$ | 5-CF$_3$ | — |
| B-54 | 2-(CH$_2$OCH(OCH$_3$)CH$_3$) | 3-CF$_3$ | H | CH$_3$ | 5-CF$_3$ | — |
| B-55 | 2-(OCH(OCH$_3$)CH$_3$) | 3-CF$_3$ | H | CH$_3$ | 5-CF$_3$ | — |
| B-56 | 2-(CO$_2^i$Pr) | 3-CF$_3$ | H | CH$_3$ | 5-CF$_3$ | — |
| B-57 | 2-(CH$_2$CH(OCH$_3$)$_2$) | 3-CF$_3$ | H | CH$_3$ | 5-CF$_3$ | — |
| B-58 | 2-([1,3]dioxolan-2-yl) | 3-CF$_3$ | H | CH$_3$ | 5-CF$_3$ | — |
| B-59 | 2-(NH$^n$Pr) | 3-CF$_3$ | H | CH$_3$ | 5-CF$_3$ | — |
| B-60 | 2-(NHCH$_2^i$Pr) | 3-CF$_3$ | H | CH$_3$ | 5-CF$_3$ | — |
| B-61 | 3-(OCH$_2^i$Pr) | 4-CF$_3$ | H | H | 5-CF$_3$ | — |
| B-62 | 3-(OCH$_2^c$Pr) | 4-CF$_3$ | H | H | 5-CF$_3$ | — |
| B-63 | 3-(O$^n$Bu) | 4-CF$_3$ | H | H | 5-CF$_3$ | — |
| B-64 | 3-(CH$_2$OCH$_2$OCH$_3$) | 4-CF$_3$ | H | H | 5-CF$_3$ | — |
| B-65 | 3-(CH$_2$OCH(OCH$_3$)CH$_3$) | 4-CF$_3$ | H | H | 5-CF$_3$ | — |
| B-66 | 3-(OCH(OCH$_3$)CH$_3$) | 4-CF$_3$ | H | H | 5-CF$_3$ | — |
| B-67 | 3-(CO$_2^i$Pr) | 4-CF$_3$ | H | H | 5-CF$_3$ | — |
| B-68 | 3-(CH$_2$CH(OCH$_3$)$_2$) | 4-CF$_3$ | H | H | 5-CF$_3$ | — |
| B-69 | 3-([1,3]dioxolan-2-yl) | 4-CF$_3$ | H | H | 5-CF$_3$ | — |
| B-70 | 3-(NH$^n$Pr) | 4-CF$_3$ | H | H | 5-CF$_3$ | — |
| B-71 | 3-(NHCH$_2^i$Pr) | 4-CF$_3$ | H | H | 5-CF$_3$ | — |
| B-72 | 3-(OCH$_2^i$Pr) | 4-CF$_3$ | H | CH$_3$ | 5-CF$_3$ | — |
| B-73 | 3-(OCH$_2^c$Pr) | 4-CF$_3$ | H | CH$_3$ | 5-CF$_3$ | — |
| B-74 | 3-(O$^n$Bu) | 4-CF$_3$ | H | CH$_3$ | 5-CF$_3$ | — |
| B-75 | 3-(CH$_2$OCH$_2$OCH$_3$) | 4-CF$_3$ | H | CH$_3$ | 5-CF$_3$ | — |
| B-76 | 3-(CH$_2$OCH(OCH$_3$)CH$_3$) | 4-CF$_3$ | H | CH$_3$ | 5-CF$_3$ | — |
| B-77 | 3-(OCH(OCH$_3$)CH$_3$) | 4-CF$_3$ | H | CH$_3$ | 5-CF$_3$ | — |
| B-78 | 3-(CO$_2^i$Pr) | 4-CF$_3$ | H | CH$_3$ | 5-CF$_3$ | — |
| B-79 | 3-(CH$_2$CH(OCH$_3$)$_2$) | 4-CF$_3$ | H | CH$_3$ | 5-CF$_3$ | — |
| B-80 | 3-([1,3]dioxolan-2-yl) | 4-CF$_3$ | H | CH$_3$ | 5-CF$_3$ | — |
| B-81 | 3-(NH$^n$Pr) | 4-CF$_3$ | H | CH$_3$ | 5-CF$_3$ | — |
| B-82 | 3-(NHCH$_2^i$Pr) | 4-CF$_3$ | H | CH$_3$ | 5-CF$_3$ | — |

TABLE 4

(Ib)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| C-1 | 2-(OCH$_2^i$Pr) | 6-CF$_3$ | H | H | 5-CF$_3$ | — |
| C-2 | 2-(OCH$_2^c$Pr) | 6-CF$_3$ | H | H | 5-CF$_3$ | — |
| C-3 | 2-(O$^n$Bu) | 6-CF$_3$ | H | H | 5-CF$_3$ | — |
| C-4 | 2-(CH$_2$OCH$_2$OCH$_3$) | 6-CF$_3$ | H | H | 5-CF$_3$ | — |
| C-5 | 2-(CH$_2$OCH(OCH$_3$)CH$_3$) | 6-CF$_3$ | H | H | 5-CF$_3$ | — |
| C-6 | 2-(OCH(OCH$_3$)CH$_3$) | 6-CF$_3$ | H | H | 5-CF$_3$ | — |
| C-7 | 2-(CO$_2^i$Pr) | 6-CF$_3$ | H | H | 5-CF$_3$ | — |
| C-8 | 2-(CH$_2$CH(OCH$_3$)$_2$) | 6-CF$_3$ | H | H | 5-CF$_3$ | — |
| C-9 | 2-([1,3]dioxolan-2-yl) | 6-CF$_3$ | H | H | 5-CF$_3$ | — |
| C-10 | 2-(NH$^n$Pr) | 6-CF$_3$ | H | H | 5-CF$_3$ | — |
| C-11 | 2-(NHCH$_2^i$Pr) | 6-CF$_3$ | H | H | 5-CF$_3$ | — |
| C-12 | 2-(OCH$_2^i$Pr) | 6-CF$_3$ | H | CH$_3$ | 5-CF$_3$ | — |
| C-13 | 2-(OCH$_2^c$Pr) | 6-CF$_3$ | H | CH$_3$ | 5-CF$_3$ | — |
| C-14 | 2-(O$^n$Bu) | 6-CF$_3$ | H | CH$_3$ | 5-CF$_3$ | — |
| C-15 | 2-(CH$_2$OCH$_2$OCH$_3$) | 6-CF$_3$ | H | CH$_3$ | 5-CF$_3$ | — |
| C-16 | 2-(CH$_2$OCH(OCH$_3$)CH$_3$) | 6-CF$_3$ | H | CH$_3$ | 5-CF$_3$ | — |
| C-17 | 2-(OCH(OCH$_3$)CH$_3$) | 6-CF$_3$ | H | CH$_3$ | 5-CF$_3$ | — |
| C-18 | 2-(CO$_2^i$Pr) | 6-CF$_3$ | H | CH$_3$ | 5-CF$_3$ | — |
| C-19 | 2-(CH$_2$CH(OCH$_3$)$_2$) | 6-CF$_3$ | H | CH$_3$ | 5-CF$_3$ | — |
| C-20 | 2-([1,3]dioxolan-2-yl) | 6-CF$_3$ | H | CH$_3$ | 5-CF$_3$ | — |
| C-21 | 2-(NH$^n$Pr) | 6-CF$_3$ | H | CH$_3$ | 5-CF$_3$ | — |
| C-22 | 2-(NHCH$_2^i$Pr) | 6-CF$_3$ | H | CH$_3$ | 5-CF$_3$ | — |
| C-23 | 2-(O$^i$Pr) | 6-CF$_3$ | H | H | 5-CF$_3$ | — |

TABLE 5

(Ic)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| D-1 | 2-(OCH$_2^i$Pr) | 5-CF$_3$ | H | H | 5-CF$_3$ | — |
| D-2 | 2-(OCH$_2^c$Pr) | 5-CF$_3$ | H | H | 5-CF$_3$ | — |
| D-3 | 2-(O$^n$Bu) | 5-CF$_3$ | H | H | 5-CF$_3$ | — |
| D-4 | 2-(CH$_2$OCH$_2$OCH$_3$) | 5-CF$_3$ | H | H | 5-CF$_3$ | — |
| D-5 | 2-(CH$_2$OCH(OCH$_3$)CH$_3$) | 5-CF$_3$ | H | H | 5-CF$_3$ | — |
| D-6 | 2-(OCH(OCH$_3$)CH$_3$) | 5-CF$_3$ | H | H | 5-CF$_3$ | — |
| D-7 | 2-(CO$_2^i$Pr) | 5-CF$_3$ | H | H | 5-CF$_3$ | — |
| D-8 | 2-(CH$_2$CH(OCH$_3$)$_2$) | 5-CF$_3$ | H | H | 5-CF$_3$ | — |
| D-9 | 2-([1,3]dioxolan-2-yl) | 5-CF$_3$ | H | H | 5-CF$_3$ | — |
| D-10 | 2-(NH$^n$Pr) | 5-CF$_3$ | H | H | 5-CF$_3$ | — |
| D-11 | 2-(NHCH$_2^i$Pr) | 5-CF$_3$ | H | H | 5-CF$_3$ | — |
| D-12 | 2-(OCH$_2^i$Pr) | 5-CF$_3$ | H | CH$_3$ | 5-CF$_3$ | — |
| D-13 | 2-(OCH$_2^c$Pr) | 5-CF$_3$ | H | CH$_3$ | 5-CF$_3$ | — |
| D-14 | 2-(O$^n$Bu) | 5-CF$_3$ | H | CH$_3$ | 5-CF$_3$ | — |
| D-15 | 2-(CH$_2$OCH$_2$OCH$_3$) | 5-CF$_3$ | H | CH$_3$ | 5-CF$_3$ | — |
| D-16 | 2-(CH$_2$OCH(OCH$_3$)CH$_3$) | 5-CF$_3$ | H | CH$_3$ | 5-CF$_3$ | — |
| D-17 | 2-(OCH(OCH$_3$)CH$_3$) | 5-CF$_3$ | H | CH$_3$ | 5-CF$_3$ | — |
| D-18 | 2-(CO$_2^i$Pr) | 5-CF$_3$ | H | CH$_3$ | 5-CF$_3$ | — |
| D-19 | 2-(CH$_2$CH(OCH$_3$)$_2$) | 5-CF$_3$ | H | CH$_3$ | 5-CF$_3$ | — |
| D-20 | 2-([1,3]dioxolan-2-yl) | 5-CF$_3$ | H | CH$_3$ | 5-CF$_3$ | — |
| D-21 | 2-(NH$^n$Pr) | 5-CF$_3$ | H | CH$_3$ | 5-CF$_3$ | — |
| D-22 | 2-(NHCH$_2^i$Pr) | 5-CF$_3$ | H | CH$_3$ | 5-CF$_3$ | — |

TABLE 6

(Id)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| E-1 | 1-(CH$_2^i$Pr) | 3-CF$_3$ | H | H | 5-CF$_3$ | — |
| E-2 | 1-(CH$_2^c$Pr) | 3-CF$_3$ | H | H | 5-CF$_3$ | — |
| E-3 | 1-$^n$Bu | 3-CF$_3$ | H | H | 5-CF$_3$ | — |
| E-4 | 1-(CH$_2$OCH$_2$OCH$_3$) | 3-CF$_3$ | H | H | 5-CF$_3$ | — |
| E-5 | 1-(CH$_2$OCH(OCH$_3$)CH$_3$) | 3-CF$_3$ | H | H | 5-CF$_3$ | — |
| E-6 | 1-(CH(OCH$_3$)CH$_3$) | 3-CF$_3$ | H | H | 5-CF$_3$ | — |
| E-7 | 1-(CO$_2^i$Pr) | 3-CF$_3$ | H | H | 5-CF$_3$ | — |
| E-8 | 1-(CH$_2$CH(OCH$_3$)$_2$) | 3-CF$_3$ | H | H | 5-CF$_3$ | — |
| E-9 | 1-([1,3]dioxolan-2-yl) | 3-CF$_3$ | H | H | 5-CF$_3$ | — |
| E-10 | 2-(CH$_2^i$Pr) | 3-CF$_3$ | H | H | 5-CF$_3$ | — |
| E-11 | 2-(CH$_2^c$Pr) | 3-CF$_3$ | H | H | 5-CF$_3$ | — |
| E-12 | 2-$^n$Bu | 3-CF$_3$ | H | H | 5-CF$_3$ | — |
| E-13 | 2-(CH$_2$OCH$_2$OCH$_3$) | 3-CF$_3$ | H | H | 5-CF$_3$ | — |
| E-14 | 2-(CH$_2$OCH(OCH$_3$)CH$_3$) | 3-CF$_3$ | H | H | 5-CF$_3$ | — |
| E-15 | 2-(CH(OCH$_3$)CH$_3$) | 3-CF$_3$ | H | H | 5-CF$_3$ | — |
| E-16 | 2-(CO$_2^i$Pr) | 3-CF$_3$ | H | H | 5-CF$_3$ | — |
| E-17 | 2-(CH$_2$CH(OCH$_3$)$_2$) | 3-CF$_3$ | H | H | 5-CF$_3$ | — |
| E-18 | 2-([1,3]dioxolan-2-yl) | 3-CF$_3$ | H | H | 5-CF$_3$ | — |
| E-19 | 1-(CH$_2^i$Pr) | 3-CF$_3$ | H | CH$_3$ | 5-CF$_3$ | — |
| E-20 | 1-(CH$_2^c$Pr) | 3-CF$_3$ | H | CH$_3$ | 5-CF$_3$ | — |
| E-21 | 1-$^n$Bu | 3-CF$_3$ | H | CH$_3$ | 5-CF$_3$ | — |
| E-22 | 1-(CH$_2$OCH$_2$OCH$_3$) | 3-CF$_3$ | H | CH$_3$ | 5-CF$_3$ | — |
| E-23 | 1-(CH$_2$OCH(OCH$_3$)CH$_3$) | 3-CF$_3$ | H | CH$_3$ | 5-CF$_3$ | — |
| E-24 | 1-(CH(OCH$_3$)CH$_3$) | 3-CF$_3$ | H | CH$_3$ | 5-CF$_3$ | — |
| E-25 | 1-(CO$_2^i$Pr) | 3-CF$_3$ | H | CH$_3$ | 5-CF$_3$ | — |
| E-26 | 1-(CH$_2$CH(OCH$_3$)$_2$) | 3-CF$_3$ | H | CH$_3$ | 5-CF$_3$ | — |
| E-27 | 1-([1,3]dioxolan-2-yl) | 3-CF$_3$ | H | CH$_3$ | 5-CF$_3$ | — |
| E-28 | 2-(CH$_2^i$Pr) | 3-CF$_3$ | H | CH$_3$ | 5-CF$_3$ | — |
| E-29 | 2-(CH$_2^c$Pr) | 3-CF$_3$ | H | CH$_3$ | 5-CF$_3$ | — |
| E-30 | 2-$^n$Bu | 3-CF$_3$ | H | CH$_3$ | 5-CF$_3$ | — |
| E-31 | 2-(CH$_2$OCH$_2$OCH$_3$) | 3-CF$_3$ | H | CH$_3$ | 5-CF$_3$ | — |
| E-32 | 2-(CH$_2$OCH(OCH$_3$)CH$_3$) | 3-CF$_3$ | H | CH$_3$ | 5-CF$_3$ | — |
| E-33 | 2-(CH(OCH$_3$)CH$_3$) | 3-CF$_3$ | H | CH$_3$ | 5-CF$_3$ | — |
| E-34 | 2-(CO$_2^i$Pr) | 3-CF$_3$ | H | CH$_3$ | 5-CF$_3$ | — |
| E-35 | 2-(CH$_2$CH(OCH$_3$)$_2$) | 3-CF$_3$ | H | CH$_3$ | 5-CF$_3$ | — |
| E-36 | 2-([1,3]dioxolan-2-yl) | 3-CF$_3$ | H | CH$_3$ | 5-CF$_3$ | — |
| E-37 | 1,3-(CH$_3$)$_2$ | — | H | H | 5-CF$_3$ | — |
| E-38 | 1-$^n$Bu-3-CH$_3$ | — | H | H | 5-CF$_3$ | — |
| E-39 | 1-CH$_3$ | 3-CF$_3$ | H | H | 5-CF$_3$ | — |
| E-40 | 1-Et | 3-CF$_3$ | H | H | 5-CF$_3$ | — |
| E-41 | 1-$^n$Pr | 3-CF$_3$ | H | H | 5-CF$_3$ | — |
| E-42 | 1-$^n$Pen | 3-CF$_3$ | H | H | 5-CF$_3$ | — |
| E-43 | 1-$^n$Hex | 3-CF$_3$ | H | H | 5-CF$_3$ | — |
| E-44 | 1-$^i$Pr | 3-CF$_3$ | H | H | 5-CF$_3$ | — |
| E-45 | 1-$^t$Bu | 3-CF$_3$ | H | H | 5-CF$_3$ | — |
| E-46 | 1-(CH$_2$CH=CH$_2$) | 3-CF$_3$ | H | H | 5-CF$_3$ | — |
| E-47 | 1-Bn | 3-CF$_3$ | H | H | 5-CF$_3$ | — |
| E-48 | 1-(2-Cl—Bn) | 3-CF$_3$ | H | H | 5-CF$_3$ | — |
| E-49 | 1-Ph | 3-CF$_3$ | H | H | 5-CF$_3$ | — |
| E-50 | 1-(3-Cl—Ph) | 3-CF$_3$ | H | H | 5-CF$_3$ | — |
| E-51 | 1-(3,5-Cl$_2$—Ph) | 3-CF$_3$ | H | H | 5-CF$_3$ | — |
| E-52 | 1-(pyridin-2-yl) | 3-CF$_3$ | H | H | 5-CF$_3$ | — |
| E-53 | 1-$^n$Bu | 3-CF$_3$-4-Cl | H | H | 5-CF$_3$ | — |
| E-54 | 1-$^n$Bu | 3-CF$_3$-4-Br | H | H | 5-CF$_3$ | — |
| E-55 | 1-$^n$Bu-4-Ph | 3-CF$_3$ | H | H | 5-CF$_3$ | — |
| E-56 | 1-CH$_3$-4-(CHO) | 3-CF$_3$ | H | H | 5-CF$_3$ | — |
| E-57 | 1-CH$_3$-4-(CH=NOCH$_3$) | 3-CF$_3$ | H | H | 5-CF$_3$ | — |
| E-58 | 1-$^n$Bu-4-(CHO) | 3-CF$_3$ | H | H | 5-CF$_3$ | — |
| E-59 | 1-$^n$Bu-3-Ph | — | H | H | 5-CF$_3$ | — |
| E-60 | 1-$^n$Bu-3-(3-Cl—Ph) | — | H | H | 5-CF$_3$ | — |
| E-61 | 1-$^n$Bu-3-(4-Cl—Ph) | — | H | H | 5-CF$_3$ | — |
| E-62 | 1-$^n$Bu-3-(3,4-Cl$_2$—Ph) | — | H | H | 5-CF$_3$ | — |
| E-63 | 1-$^n$Bu-3-(3,5-Cl$_2$—Ph) | — | H | H | 5-CF$_3$ | — |
| E-64 | 1-$^n$Bu | 3-CF$_3$ | H | H | 5-CN | — |
| E-65 | 1-$^n$Bu | 3-CF$_3$ | H | H | — | 5-NO$_2$ |
| E-66 | 1-(3-CF$_3$—Ph) | 3-CF$_3$ | H | H | 5-CF$_3$ | — |
| E-67 | 1-(3-CH$_3$—Ph) | 3-CF$_3$ | H | H | 5-CF$_3$ | — |
| E-68 | 1-(pyridin-2-yl)-3-(3,4,5-F$_3$—Ph) | — | H | H | 5-CF$_3$ | — |
| E-69 | 1-(pyridin-2-yl)-3-(3,5-F$_2$—Ph) | — | H | H | 5-CF$_3$ | — |

TABLE 6-continued (Id)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| E-70 | 1-(3-Cl-pyridin-2-yl) | | 3-CF$_3$ | H | H | 5-CF$_3$ | — |
| E-71 | 1-(6-CH$_3$-pyridin-2-yl) | | 3-CF$_3$ | H | H | 5-CF$_3$ | — |
| E-72 | 1-(4-CF$_3$-pyridin-2-yl) | | 3-CF$_3$ | H | H | 5-CF$_3$ | — |
| E-73 | 1,4-(CH$_3$)$_2$ | | 3-CF$_3$ | H | H | 5-CF$_3$ | — |
| E-74 | 1-CH$_3$-4-(CH$_2$OH) | | 3-CF$_3$ | H | H | 5-CF$_3$ | — |
| E-75 | 1-$^n$Bu-4-CH$_3$ | | 3-CF$_3$ | H | H | 5-CF$_3$ | — |
| E-76 | 1-$^n$Bu-3-(3,5-CF$_3$)$_2$—Ph | | — | H | H | 5-CF$_3$ | — |
| E-77 | 1-$^n$Bu-3-(3,5-F$_2$—Ph) | | — | H | H | 5-CF$_3$ | — |
| E-78 | 1-$^n$Bu-3-(3,4,5-F$_3$—Ph) | | — | H | H | 5-CF$_3$ | — |
| E-79 | 1,4-(CH$_3$)$_2$-3-(CO$_2$Et) | | — | H | H | 5-CF$_3$ | — |
| E-80 | 1-CH$_3$ | | 4-Cl-3-CF$_3$ | H | H | 5-CF$_3$ | — |
| E-81 | — | | 3-CF$_3$ | H | H | 5-CF$_3$ | — |
| E-82 | 1-(C(=O)$^t$Bu) | | 3-CF$_3$ | H | H | 5-CF$_3$ | — |
| E-83 | 1-(pyridin-2-yl)-3-(3,5-Cl$_2$—Ph) | | — | H | H | 5-CF$_3$ | — |
| E-84 | 1-(CH$_2$OCH$_3$) | | 3-CF$_3$ | H | H | 5-CF$_3$ | — |
| E-85 | 1-(CH$_2$OEt) | | 3-CF$_3$ | H | H | 5-CF$_3$ | — |
| E-86 | 1-(CH$_2$CH$_2$OCH$_3$) | | 3-CF$_3$ | H | H | 5-CF$_3$ | — |
| E-87 | 1-(CH$_2$CH$_2$OEt) | | 3-CF$_3$ | H | H | 5-CF$_3$ | — |
| E-88 | 1-(CH$_2$CH(OEt)$_2$) | | 3-CF$_3$ | H | H | 5-CF$_3$ | — |
| E-89 | 1-(CH$_2$CH$_2$CH(OCH$_3$)$_2$) | | 3-CF$_3$ | H | H | 5-CF$_3$ | — |
| E-90 | 1-(CH$_2$CH$_2$CH(OEt)$_2$) | | 3-CF$_3$ | H | H | 5-CF$_3$ | — |
| E-91 | 1-(CH$_2$([1,3]dioxolan-2-yl)) | | 3-CF$_3$ | H | H | 5-CF$_3$ | — |
| E-92 | 1-(CH$_2$(tetrahydro-furan-2-yl)) | | 3-CF$_3$ | H | H | 5-CF$_3$ | — |
| E-93 | 1-(CH$_2$([1,3]dioxolan-2-yl)) | | 3-CF$_3$ | H | H | 5-CF$_3$ | — |
| E-94 | 1-(CH$_2$CH$_2$([1,3]dioxolan-2-yl)) | | 3-CF$_3$ | H | H | 5-CF$_3$ | — |
| E-95 | 1-Ac | | 3-CF$_3$ | H | H | 5-CF$_3$ | — |
| E-96 | 1-(C(=O)Et) | | 3-CF$_3$ | H | H | 5-CF$_3$ | — |
| E-97 | 1-(C(=O)$^n$Pr) | | 3-CF$_3$ | H | H | 5-CF$_3$ | — |
| E-98 | 1-(C(=O)$^n$Bu) | | 3-CF$_3$ | H | H | 5-CF$_3$ | — |
| E-99 | 1-(C(=O)Ph) | | 3-CF$_3$ | H | H | 5-CF$_3$ | — |
| E-100 | 1-(CO$_2$CH$_3$) | | 3-CF$_3$ | H | H | 5-CF$_3$ | — |
| E-101 | 1-(CO$_2$Et) | | 3-CF$_3$ | H | H | 5-CF$_3$ | — |
| E-102 | 1-(CO$_2$$^n$Pr) | | 3-CF$_3$ | H | H | 5-CF$_3$ | — |
| E-103 | 1-(CO$_2$$^n$Bu) | | 3-CF$_3$ | H | H | 5-CF$_3$ | — |
| E-104 | 1-(CH$_2$CHO) | | 3-CF$_3$ | H | H | 5-CF$_3$ | — |
| E-105 | 1-(CH$_2$CH$_2$CHO) | | 3-CF$_3$ | H | H | 5-CF$_3$ | — |
| E-106 | 1-CH$_3$-4-(CH=NOH) | | 3-CF$_3$ | H | H | 5-CF$_3$ | — |
| E-107 | 1-CH$_3$-4-(CH=NOEt) | | 3-CF$_3$ | H | H | 5-CF$_3$ | — |
| E-108 | 3-(3,5-F$_2$—Ph) | | — | H | H | 5-CF$_3$ | — |
| E-109 | 1-(CH$_2$CH(OCH$_3$)$_2$)-3-(3,5-F$_2$—Ph) | | — | H | H | 5-CF$_3$ | — |
| E-110 | 1-(CH$_2$([1,3]dioxolan-2-yl))-3-(3,5-F$_2$—Ph) | | — | H | H | 5-CF$_3$ | — |
| E-111 | 1-(pyridin-2-yl)-3-(thiophen-2-yl) | | — | H | H | 5-CF$_3$ | — |
| E-112 | 1-(CH$_2$CH$_2$CH=CH$_2$) | | 3-CF$_3$ | H | H | 5-CF$_3$ | — |
| E-113 | 1-(CH$_2$CH$_2$CH(Et)$_2$) | | 3-CF$_3$ | H | H | 5-CF$_3$ | — |
| E-114 | 1-$^i$Pen | | 3-CF$_3$ | H | H | 5-CF$_3$ | — |

TABLE 7

(Ie)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| F-1 | 2-(CH$_2$$^i$Pr) | | 3-CF$_3$ | H | H | 5-CF$_3$ | — |
| F-2 | 2-(CH$_2$$^c$Pr) | | 3-CF$_3$ | H | H | 5-CF$_3$ | — |
| F-3 | 2-$^n$Bu | | 3-CF$_3$ | H | H | 5-CF$_3$ | — |
| F-4 | 2-(CH$_2$OCH$_2$OCH$_3$) | | 3-CF$_3$ | H | H | 5-CF$_3$ | — |
| F-5 | 2-(CH$_2$OCH(OCH$_3$)CH$_3$) | | 3-CF$_3$ | H | H | 5-CF$_3$ | — |
| F-6 | 2-(CH(OCH$_3$)CH$_3$) | | 3-CF$_3$ | H | H | 5-CF$_3$ | — |
| F-7 | 2-(CO$_2$$^i$Pr) | | 3-CF$_3$ | H | H | 5-CF$_3$ | — |
| F-8 | 2-(CH$_2$CH(OCH$_3$)$_2$) | | 3-CF$_3$ | H | H | 5-CF$_3$ | — |
| F-9 | 2-([1,3]dioxolan-2-yl) | | 3-CF$_3$ | H | H | 5-CF$_3$ | — |
| F-10 | 1-(CH$_2$$^i$Pr) | | 3-CF$_3$ | H | H | 5-CF$_3$ | — |

TABLE 7-continued

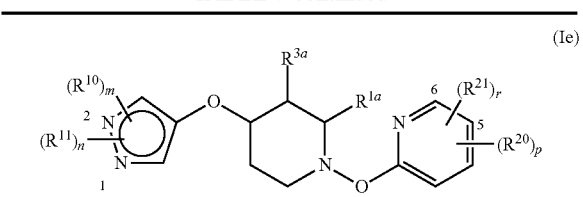

(Ie)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| F-11 | 1-($CH_2{}^cPr$) | 3-$CF_3$ | H | H | 5-$CF_3$ | — |
| F-12 | 1-${}^nBu$ | 3-$CF_3$ | H | H | 5-$CF_3$ | — |
| F-13 | 1-($CH_2OCH_2OCH_3$) | 3-$CF_3$ | H | H | 5-$CF_3$ | — |
| F-14 | 1-($CH_2OCH(OCH_3)CH_3$) | 3-$CF_3$ | H | H | 5-$CF_3$ | — |
| F-15 | 1-($OCH(OCH_3)CH_3$) | 3-$CF_3$ | H | H | 5-$CF_3$ | — |
| F-16 | 1-($CO_2{}^iPr$) | 3-$CF_3$ | H | H | 5-$CF_3$ | — |
| F-17 | 1-($CH_2CH(OCH_3)_2$) | 3-$CF_3$ | H | H | 5-$CF_3$ | — |
| F-18 | 1-([1,3]dioxolan-2-yl) | 3-$CF_3$ | H | H | 5-$CF_3$ | — |
| F-19 | 2-($CH_2{}^iPr$) | 3-$CF_3$ | H | $CH_3$ | 5-$CF_3$ | — |
| F-20 | 2-($CH_2{}^cPr$) | 3-$CF_3$ | H | $CH_3$ | 5-$CF_3$ | — |
| F-21 | 2-${}^nBu$ | 3-$CF_3$ | H | $CH_3$ | 5-$CF_3$ | — |
| F-22 | 2-($CH_2OCH_2OCH_3$) | 3-$CF_3$ | H | $CH_3$ | 5-$CF_3$ | — |
| F-23 | 2-($CH_2OCH(OCH_3)CH_3$) | 3-$CF_3$ | H | $CH_3$ | 5-$CF_3$ | — |
| F-24 | 2-($CH(OCH_3)CH_3$) | 3-$CF_3$ | H | $CH_3$ | 5-$CF_3$ | — |

TABLE 7-continued

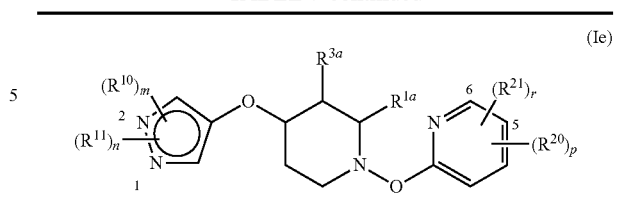

(Ie)

| Compound No. | $(R^{10})_m$ | $(R^{11})_n$ | $R^{1a}$ | $R^{3a}$ | $(R^{20})_p$ | $(R^{21})_r$ |
|---|---|---|---|---|---|---|
| F-25 | 2-($CO_2{}^iPr$) | 3-$CF_3$ | H | $CH_3$ | 5-$CF_3$ | — |
| F-26 | 2-($CH_2CH(OCH_3)_2$) | 3-$CF_3$ | H | $CH_3$ | 5-$CF_3$ | — |
| F-27 | 2-([1,3]dioxolan-2-yl) | 3-$CF_3$ | H | $CH_3$ | 5-$CF_3$ | — |
| F-28 | 1-($CH_2{}^iPr$) | 3-$CF_3$ | H | $CH_3$ | 5-$CF_3$ | — |
| F-29 | 1-($CH_2{}^cPr$) | 3-$CF_3$ | H | $CH_3$ | 5-$CF_3$ | — |
| F-30 | 1-${}^nBu$ | 3-$CF_3$ | H | $CH_3$ | 5-$CF_3$ | — |
| F-31 | 1-($CH_2OCH_2OCH_3$) | 3-$CF_3$ | H | $CH_3$ | 5-$CF_3$ | — |
| F-32 | 1-($CH_2OCH(OCH_3)CH_3$) | 3-$CF_3$ | H | $CH_3$ | 5-$CF_3$ | — |
| F-33 | 1-($OCH(OCH_3)CH_3$) | 3-$CF_3$ | H | $CH_3$ | 5-$CF_3$ | — |
| F-34 | 1-($CO_2{}^iPr$) | 3-$CF_3$ | H | $CH_3$ | 5-$CF_3$ | — |
| F-35 | 1-($CH_2CH(OCH_3)_2$) | 3-$CF_3$ | H | $CH_3$ | 5-$CF_3$ | — |
| F-36 | 1-([1,3]dioxolan-2-yl) | 3-$CF_3$ | H | $CH_3$ | 5-$CF_3$ | — |

TABLE 8

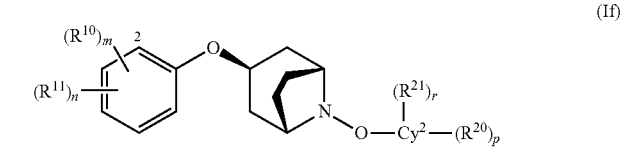

(If)

| Compound No. | $(R^{10})_m$ | $(R^{11})_n$ | $Cy^2$—$(R^{20})_p$ | $(R^{21})_r$ |
|---|---|---|---|---|
| G-1 | 2-($OCH_2{}^iPr$) | 4-$CF_3$ | 6-$CF_3$-pyridazin-3-yl | — |
| G-2 | 2-($OCH_2{}^cPr$) | 4-$CF_3$ | 6-$CF_3$-pyridazin-3-yl | — |
| G-3 | 2-($CH_2OCH(OCH_3)CH_3$) | 4-$CF_3$ | 6-$CF_3$-pyridazin-3-yl | — |
| G-4 | 2-($CO_2{}^iPr$) | 4-$CF_3$ | 6-$CF_3$-pyridazin-3-yl | — |
| G-5 | 2-($OCH_2{}^iPr$) | 4-$CF_3$ | 6-CN-pyridazin-3-yl | — |
| G-6 | 2-($OCH_2{}^cPr$) | 4-$CF_3$ | 6-CN-pyridazin-3-yl | — |
| G-7 | 2-($CH_2OCH(OCH_3)CH_3$) | 4-$CF_3$ | 6-CN-pyridazin-3-yl | — |
| G-8 | 2-($CO_2{}^iPr$) | 4-$CF_3$ | 6-CN-pyridazin-3-yl | — |
| G-9 | 2-($OCH_2{}^iPr$) | 4-$CF_3$ | 6-Cl-pyridazin-3-yl | — |
| G-10 | 2-($OCH_2{}^cPr$) | 4-$CF_3$ | 6-Cl-pyridazin-3-yl | — |
| G-11 | 2-($CH_2OCH(OCH_3)CH_3$) | 4-$CF_3$ | 6-Cl-pyridazin-3-yl | — |
| G-12 | 2-($CO_2{}^iPr$) | 4-$CF_3$ | 6-Cl-pyridazin-3-yl | — |
| G-13 | 2-($OCH_2{}^iPr$) | 4-$CF_3$ | 5-$CF_3$-pyridin-2-yl | 1-oxy |
| G-14 | 2-($OCH_2{}^cPr$) | 4-$CF_3$ | 5-$CF_3$-pyridin-2-yl | 1-oxy |
| G-15 | 2-($CH_2OCH(OCH_3)CH_3$) | 4-$CF_3$ | 5-$CF_3$-pyridin-2-yl | 1-oxy |
| G-16 | 2-($CO_2{}^iPr$) | 4-$CF_3$ | 5-$CF_3$-pyridin-2-yl | 1-oxy |
| G-17 | 2-($OCH_2{}^iPr$) | 4-$CF_3$ | 5-$CF_3$-pyrimidin-2-yl | — |
| G-18 | 2-($OCH_2{}^cPr$) | 4-$CF_3$ | 5-$CF_3$-pyrimidin-2-yl | — |
| G-19 | 2-($CH_2OCH(OCH_3)CH_3$) | 4-$CF_3$ | 5-$CF_3$-pyrimidin-2-yl | — |
| G-20 | 2-($CO_2{}^iPr$) | 4-$CF_3$ | 5-$CF_3$-pyrimidin-2-yl | — |
| G-21 | 2-($OCH_2{}^iPr$) | 4-$CF_3$ | 6-$CF_3$-pyrimidin-2-yl | 4-($OCH_3$) |
| G-22 | 2-($OCH_2{}^cPr$) | 4-$CF_3$ | 6-$CF_3$-pyrimidin-2-yl | 4-($OCH_3$) |
| G-23 | 2-($CH_2OCH(OCH_3)CH_3$) | 4-$CF_3$ | 6-$CF_3$-pyrimidin-2-yl | 4-($OCH_3$) |
| G-24 | 2-($CO_2{}^iPr$) | 4-$CF_3$ | 6-$CF_3$-pyrimidin-2-yl | 4-($OCH_3$) |
| G-25 | 2-($OCH_2{}^iPr$) | 4-$CF_3$ | 6-$CF_3$-pyrimidin-4-yl | — |
| G-26 | 2-($OCH_2{}^cPr$) | 4-$CF_3$ | 6-$CF_3$-pyrimidin-4-yl | — |
| G-27 | 2-($CH_2OCH(OCH_3)CH_3$) | 4-$CF_3$ | 6-$CF_3$-pyrimidin-4-yl | — |
| G-28 | 2-($CO_2{}^iPr$) | 4-$CF_3$ | 6-$CF_3$-pyrimidin-4-yl | — |
| G-29 | 2-($OCH_2{}^iPr$) | 4-$CF_3$ | 5-$CF_3$-thiazol-2-yl | — |
| G-30 | 2-($OCH_2{}^cPr$) | 4-$CF_3$ | 5-$CF_3$-thiazol-2-yl | — |
| G-31 | 2-($CH_2OCH(OCH_3)CH_3$) | 4-$CF_3$ | 5-$CF_3$-thiazol-2-yl | — |
| G-32 | 2-($CO_2{}^iPr$) | 4-$CF_3$ | 5-$CF_3$-thiazol-2-yl | — |
| G-33 | 2-($OCH_2{}^iPr$) | 4-$CF_3$ | 5-$CF_3$-[1,3,4]thiadiazol-2-yl | — |
| G-34 | 2-($OCH_2{}^cPr$) | 4-$CF_3$ | 5-$CF_3$-[1,3,4]thiadiazol-2-yl | — |
| G-35 | 2-($CH_2OCH(OCH_3)CH_3$) | 4-$CF_3$ | 5-$CF_3$-[1,3,4]thiadiazol-2-yl | — |
| G-36 | 2-($CO_2{}^iPr$) | 4-$CF_3$ | 5-$CF_3$-[1,3,4]thiadiazol-2-yl | — |
| G-37 | 2-($OCH_2{}^iPr$) | 4-$CF_3$ | 4-$CF_3$Ph | — |
| G-38 | 2-($OCH_2{}^cPr$) | 4-$CF_3$ | 4-$CF_3$Ph | — |
| G-39 | 2-($CH_2OCH(OCH_3)CH_3$) | 4-$CF_3$ | 4-$CF_3$Ph | — |

TABLE 8-continued (If)

| Compound No. | $(R^{10})_m$ | $(R^{11})_n$ | $Cy^2$—$(R^{20})_p$ | $(R^{21})_r$ |
|---|---|---|---|---|
| G-40 | 2-($CO_2{}^iPr$) | 4-$CF_3$ | 4-$CF_3$Ph | — |
| G-41 | 2-($OCH_2{}^iPr$) | 4-$CF_3$ | 3-F-4-$CF_3$—Ph | — |
| G-42 | 2-($OCH_2{}^cPr$) | 4-$CF_3$ | 3-F-4-$CF_3$—Ph | — |
| G-43 | 2-($CH_2OCH(OCH_3)CH_3$) | 4-$CF_3$ | 3-F-4-$CF_3$—Ph | — |
| G-44 | 2-($CO_2{}^iPr$) | 4-$CF_3$ | 3-F-4-$CF_3$—Ph | — |
| G-45 | 2-($OCH_2{}^iPr$) | 4-$CF_3$ | 3-F-5-$CF_3$—Ph | — |
| G-46 | 2-($OCH_2{}^cPr$) | 4-$CF_3$ | 3-F-5-$CF_3$—Ph | — |
| G-47 | 2-($CH_2OCH(OCH_3)CH_3$) | 4-$CF_3$ | 3-F-5-$CF_3$—Ph | — |
| G-48 | 2-($CO_2{}^iPr$) | 4-$CF_3$ | 3-F-5-$CF_3$—Ph | — |
| G-49 | 2-($O^nPr$) | 4-$CF_3$ | 3-F-4-$CF_3$—Ph | — |
| G-50 | 2-($OCH_2{}^cPr$) | 4-$CF_3$ | 6-$CF_3$-pyridin-3-yl | — |
| G-51 | 2-($OCH_2{}^iPr$) | 4-$CF_3$ | 6-$CF_3$-pyridin-3-yl | — |
| G-52 | 2-($CH_2OCH(OCH_3)CH_3$) | 4-$CF_3$ | 6-$CF_3$-pyridin-3-yl | — |
| G-53 | 2-($CO_2{}^iPr$) | 4-$CF_3$ | 6-$CF_3$-pyridin-3-yl | — |
| G-54 | 2-($OCH_2{}^cPr$) | 4-$CF_3$ | 5-CN-thiazol-2-yl | — |
| G-55 | 2-($OCH_2{}^cPr$) | 4-$CF_3$ | 3-$CF_3$-[1,2,4]-triazol-2-yl | 1-$^nBu$ |
| G-56 | 2-($OCH_2{}^cPr$) | 4-$CF_3$ | 4-$CF_3$-5-CN-pyrimidin-6-yl | — |
| G-57 | 2-($OCH_2{}^cPr$) | 4-$CF_3$ | 4-$CF_3$-pyrimidin-2-yl | 6-($OCH_3$) |

TABLE 9

(Ig)

| Compound No. | $(R^{10})_m$ | $(R^{11})_n$ | $Cy^2$—$(R^{20})_p$ | $(R^{21})_r$ |
|---|---|---|---|---|
| J-1 | 2-($OCH_2{}^iPr$) | 4-$CF_3$ | 5-$CF_3$-pyridin-2-yl | — |
| J-2 | 2-($OCH_2{}^cPr$) | 4-$CF_3$ | 5-$CF_3$-pyridin-2-yl | — |
| J-3 | 2-($CH_2OCH(OCH_3)CH_3$) | 4-$CF_3$ | 5-$CF_3$-pyridin-2-yl | — |
| J-4 | 2-($CO_2{}^iPr$) | 4-$CF_3$ | 5-$CF_3$-pyridin-2-yl | — |
| J-5 | 2-($OCH_2{}^iPr$) | 4-$CF_3$ | 6-$CF_3$-pyridazin-3-yl | — |
| J-6 | 2-($OCH_2{}^cPr$) | 4-$CF_3$ | 6-$CF_3$-pyridazin-3-yl | — |
| J-7 | 2-($CH_2OCH(OCH_3)CH_3$) | 4-$CF_3$ | 6-$CF_3$-pyridazin-3-yl | — |
| J-8 | 2-($CO_2{}^iPr$) | 4-$CF_3$ | 6-$CF_3$-pyridazin-3-yl | — |
| J-9 | 2-($OCH_2{}^iPr$) | 4-$CF_3$ | 5-$CF_3$-pyrimidin-2-yl | — |
| J-10 | 2-($OCH_2{}^cPr$) | 4-$CF_3$ | 5-$CF_3$-pyrimidin-2-yl | — |
| J-11 | 2-($CH_2OCH(OCH_3)CH_3$) | 4-$CF_3$ | 5-$CF_3$-pyrimidin-2-yl | — |
| J-12 | 2-($CO_2{}^iPr$) | 4-$CF_3$ | 5-$CF_3$-pyrimidin-2-yl | — |
| J-13 | 2-($OCH_2{}^iPr$) | 4-$CF_3$ | 5-$CF_3$-thiazol-2-yl | — |
| J-14 | 2-($OCH_2{}^cPr$) | 4-$CF_3$ | 5-$CF_3$-thiazol-2-yl | — |
| J-15 | 2-($CH_2OCH(OCH_3)CH_3$) | 4-$CF_3$ | 5-$CF_3$-thiazol-2-yl | — |
| J-16 | 2-($CO_2{}^iPr$) | 4-$CF_3$ | 5-$CF_3$-thiazol-2-yl | — |
| J-17 | 2-($OCH_2{}^iPr$) | 4-$CF_3$ | 5-$CF_3$-[1,3,4]thiadiazol-2-yl | — |
| J-18 | 2-($OCH_2{}^cPr$) | 4-$CF_3$ | 5-$CF_3$-[1,3,4]thiadiazol-2-yl | — |
| J-19 | 2-($CH_2OCH(OCH_3)CH_3$) | 4-$CF_3$ | 5-$CF_3$-[1,3,4]thiadiazol-2-yl | — |
| J-20 | 2-($CO_2{}^iPr$) | 4-$CF_3$ | 5-$CF_3$-[1,3,4]thiadiazol-2-yl | — |
| J-61 | 2-($OCH_2{}^cPr$) | 4-$CF_3$ | 4-$CF_3$-pyridin-2-yl | — |
| J-62 | 2-($OCH_2{}^cPr$) | 4-$CF_3$ | 6-CN-pyridazin-3-yl | — |
| J-63 | 2-($OCH_2{}^cPr$) | 4-$CF_3$ | 6-$CF_3$-pyridin-3-yl | — |
| J-64 | 2-($NHCH_2{}^iPr$) | 4-$CF_3$ | 5-$CF_3$-pyridin-2-yl | — |

TABLE 10

(Ih)

| Compound No. | $Cy^1$ | $(R^{10})_m$ | $(R^{11})_n$ | $Cy^2$ | $(R^{21})_r$ | $(R^{20})_p$ |
|---|---|---|---|---|---|---|
| K-1 | pyridin-2-yl | — | 5-$CF_3$ | Ph | 2-($OCH_2{}^iPr$) | 4-$CF_3$ |
| K-2 | pyridin-2-yl | — | 5-$CF_3$ | Ph | 2-($OCH_2{}^cPr$) | 4-$CF_3$ |
| K-3 | pyridin-2-yl | — | 5-$CF_3$ | Ph | 2-($CH_2OCH(OCH_3)CH_3$) | 4-$CF_3$ |
| K-4 | pyridin-2-yl | — | 5-$CF_3$ | Ph | 2-($CO_2{}^iPr$) | 4-$CF_3$ |
| K-13 | pyridin-2-yl | — | 5-$CF_3$ | Ph | 2-($CO_2Et$) | 4-$CF_3$ |
| K-14 | pyridazin-3-yl | — | 6-$CF_3$ | Ph | 2-($OCH_2{}^iPr$) | 4-$CF_3$ |

TABLE 10-continued

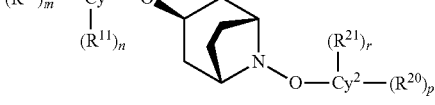

(Ih)

| Compound No. | Cy¹ | $(R^{10})_m$ | $(R^{11})_n$ | Cy² | $(R^{21})_r$ | $(R^{20})_p$ |
|---|---|---|---|---|---|---|
| K-15 | pyridazin-3-yl | — | 6-CF₃ | Ph | 2-(OCH₂ᶜPr) | 4-CF₃ |
| K-16 | pyridazin-3-yl | — | 6-CF₃ | Ph | 2-(CH₂OCH(OCH₃)CH₃) | 4-CF₃ |
| K-17 | pyridazin-3-yl | — | 6-CF₃ | Ph | 2-(CO₂ⁱPr) | 4-CF₃ |
| K-26 | pyridin-2-yl | — | 5-CN | Ph | 2-(OCH₂ⁱPr) | 4-CF₃ |
| K-27 | pyridin-2-yl | — | 5-CN | Ph | 2-(OCH₂ᶜPr) | 4-CF₃ |
| K-28 | pyridin-2-yl | — | 5-CN | Ph | 2-(CH₂OCH(OCH₃)CH₃) | 4-CF₃ |
| K-29 | pyridin-2-yl | — | 5-CN | Ph | 2-(CO₂ⁱPr) | 4-CF₃ |
| K-30 | pyrazol-5-yl | 1-CH₃ | 3-CF₃ | pyridin-2-yl | — | 5-CF₃ |
| K-31 | pyrazol-5-yl | 1-(CH₂ⁱPr) | 3-CF₃ | pyridin-2-yl | — | 5-CF₃ |
| K-32 | pyrazol-5-yl | 1-(CH₂ᶜPr) | 3-CF₃ | pyridin-2-yl | — | 5-CF₃ |
| K-33 | pyrazol-5-yl | 1-ⁿBu | 3-CF₃ | pyridin-2-yl | — | 5-CF₃ |
| K-34 | pyrazol-5-yl | 1-(CH₂OCH₂OCH₃) | 3-CF₃ | pyridin-2-yl | — | 5-CF₃ |
| K-35 | pyrazol-5-yl | 1-(CH₂OCH(OCH₃)CH₃) | 3-CF₃ | pyridin-2-yl | — | 5-CF₃ |
| K-36 | pyrazol-5-yl | 1-(CH(OCH₃)₂) | 3-CF₃ | pyridin-2-yl | — | 5-CF₃ |
| K-37 | pyrazol-5-yl | 1-(CO₂ⁱPr) | 3-CF₃ | pyridin-2-yl | — | 5-CF₃ |
| K-38 | pyrazol-5-yl | 1-(CH₂CH(OCH₃)₂) | 3-CF₃ | pyridin-2-yl | — | 5-CF₃ |
| K-39 | pyrazol-5-yl | 1-([1,3]dioxolan-2-yl) | 3-CF₃ | pyridin-2-yl | — | 5-CF₃ |
| K-40 | pyrazol-5-yl | 1-ⁿBu-3-CH₃ | — | pyridin-2-yl | — | 5-CF₃ |
| K-41 | pyrazol-5-yl | 1-Et | 3-CF₃ | pyridin-2-yl | — | 5-CF₃ |
| K-42 | pyrazol-5-yl | 1-ⁿPr | 3-CF₃ | pyridin-2-yl | — | 5-CF₃ |
| K-43 | pyrazol-5-yl | 1-ⁿPen | 3-CF₃ | pyridin-2-yl | — | 5-CF₃ |
| K-44 | pyrazol-5-yl | 1-ⁿHex | 3-CF₃ | pyridin-2-yl | — | 5-CF₃ |
| K-45 | pyrazol-5-yl | 1-ⁱPr | 3-CF₃ | pyridin-2-yl | — | 5-CF₃ |
| K-46 | pyrazol-5-yl | 1-(CH₂CH=CH₂) | 3-CF₃ | pyridin-2-yl | — | 5-CF₃ |
| K-47 | pyrazol-5-yl | 1-Bn | 3-CF₃ | pyridin-2-yl | — | 5-CF₃ |
| K-48 | pyrazol-5-yl | 1-(2-Cl—Bn) | 3-CF₃ | pyridin-2-yl | — | 5-CF₃ |
| K-49 | pyrazol-5-yl | 1-(3-Cl—Ph) | 3-CF₃ | pyridin-2-yl | — | 5-CF₃ |
| K-50 | pyrazol-5-yl | 1-(3,5-Cl₂—Ph) | 3-CF₃ | pyridin-2-yl | — | 5-CF₃ |
| K-51 | pyrazol-5-yl | 1-(pyridin-2-yl) | 3-CF₃ | pyridin-2-yl | — | 5-CF₃ |
| K-52 | pyrazol-5-yl | 1-ⁿBu-3-(3-Cl—Ph) | — | pyridin-2-yl | — | 5-CF₃ |
| K-53 | pyrazol-5-yl | 1-ⁿBu-3-(4-Cl—Ph) | — | pyridin-2-yl | — | 5-CF₃ |
| K-54 | pyrazol-5-yl | 1-ⁿBu-3-(3,4-Cl₂—Ph) | — | pyridin-2-yl | — | 5-CF₃ |
| K-55 | pyrazol-5-yl | 1-ⁿBu-3-(3,5-Cl₂—Ph) | — | pyridin-2-yl | — | 5-CF₃ |
| K-56 | pyrazol-5-yl | 1-(3-CF₃—Ph) | 3-CF₃ | pyridin-2-yl | — | 5-CF₃ |
| K-57 | pyrazol-5-yl | 1-(3-CH₃—Ph) | 3-CF₃ | pyridin-2-yl | — | 5-CF₃ |
| K-58 | pyrazol-5-yl | 1-(pyridin-2-yl)-3-(3,4,5-F₃—Ph) | — | pyridin-2-yl | — | 5-CF₃ |
| K-59 | pyrazol-5-yl | 1-(pyridin-2-yl)-3-(3,5-F₂—Ph) | — | pyridin-2-yl | — | 5-CF₃ |
| K-60 | pyrazol-5-yl | 1-(6-CH₃-pyridin-2-yl) | 3-CF₃ | pyridin-2-yl | — | 5-CF₃ |
| K-61 | pyrazol-5-yl | 1-(4-CF₃-thiazol-2-yl) | 3-CF₃ | pyridin-2-yl | — | 5-CF₃ |
| K-62 | pyrazol-5-yl | 1-ⁿBu-4-CH₃ | 3-CF₃ | pyridin-2-yl | — | 5-CF₃ |
| K-63 | pyrazol-5-yl | 1-ⁿBu-3-(3,5-(CF₃)₂—Ph) | — | pyridin-2-yl | — | 5-CF₃ |
| K-64 | pyrazol-5-yl | 1-ⁿBu-3-(3,5-F₂—Ph) | — | pyridin-2-yl | — | 5-CF₃ |
| K-65 | pyrazol-5-yl | 1-ⁿBu-3-(3,4,5-F₂—Ph) | — | pyridin-2-yl | — | 5-CF₃ |
| K-66 | pyrazol-5-yl | 1-(C(=O)ⁱBu) | 3-CF₃ | pyridin-2-yl | — | 5-CF₃ |
| K-67 | pyrazol-5-yl | 1-(pyridin-2-yl)-3-(3,5-Cl₂—Ph) | — | pyridin-2-yl | — | 5-CF₃ |
| K-68 | pyrazol-5-yl | 1-(CH₂OCH₃) | 3-CF₃ | pyridin-2-yl | — | 5-CF₃ |
| K-69 | pyrazol-5-yl | 1-(CH₂OEt) | 3-CF₃ | pyridin-2-yl | — | 5-CF₃ |
| K-70 | pyrazol-5-yl | 1-(CH₂CH₂OCH₃) | 3-CF₃ | pyridin-2-yl | — | 5-CF₃ |
| K-71 | pyrazol-5-yl | 1-(CH₂CH₂OEt) | 3-CF₃ | pyridin-2-yl | — | 5-CF₃ |
| K-72 | pyrazol-5-yl | 1-(CH₂CH(OEt)₂) | 3-CF₃ | pyridin-2-yl | — | 5-CF₃ |
| K-73 | pyrazol-5-yl | 1-(CH₂CH₂CH(OCH₃)₂) | 3-CF₃ | pyridin-2-yl | — | 5-CF₃ |
| K-74 | pyrazol-5-yl | 1-(CH₂CH₂CH(OEt)₂) | 3-CF₃ | pyridin-2-yl | — | 5-CF₃ |
| K-75 | pyrazol-5-yl | 1-(CH₂([1,3]dioxolan-2-yl)) | 3-CF₃ | pyridin-2-yl | — | 5-CF₃ |
| K-76 | pyrazol-5-yl | 1-(CH₂(tetrahydro-furan-2-yl)) | 3-CF₃ | pyridin-2-yl | — | 5-CF₃ |
| K-77 | pyrazol-5-yl | 1-(CH₂CH₂([1,3]dioxolan-2-yl)) | 3-CF₃ | pyridin-2-yl | — | 5-CF₃ |
| K-78 | pyrazol-5-yl | 1-(CH₂CH₂([1,3]dioxolan-2-yl)) | 3-CF₃ | pyridin-2-yl | — | 5-CF₃ |
| K-79 | pyrazol-5-yl | 1-Ac | 3-CF₃ | pyridin-2-yl | — | 5-CF₃ |
| K-80 | pyrazol-5-yl | 1-(C(=O)Et) | 3-CF₃ | pyridin-2-yl | — | 5-CF₃ |
| K-81 | pyrazol-5-yl | 1-(C(=O)ⁿPr) | 3-CF₃ | pyridin-2-yl | — | 5-CF₃ |
| K-82 | pyrazol-5-yl | 1-(CH₂CH(OCH₃)₂)-3-(3,5-F₂—Ph) | — | pyridin-2-yl | — | 5-CF₃ |
| K-83 | pyrazol-5-yl | 1-(CH₂([1,3]dioxolan-2-yl))-3-(3,5-F₂—Ph) | — | pyridin-2-yl | — | 5-CF₃ |
| K-84 | pyrazol-5-yl | 1-(pyridin-2-yl)-3-(thiophen-2-yl) | — | pyridin-2-yl | — | 5-CF₃ |
| K-85 | pyrazol-5-yl | 1-(CH₂CH₂CH=CH₂) | 3-CF₃ | pyridin-2-yl | — | 5-CF₃ |
| K-86 | pyrazol-5-yl | 1-(CH₂CH₂CH(Et)₂) | 3-CF₃ | pyridin-2-yl | — | 5-CF₃ |
| K-87 | pyrazol-5-yl | 1-ⁱPen | 3-CF₃ | pyridin-2-yl | — | 5-CF₃ |

TABLE 11

(Ii)

$(R^{10})_m$—Cy$^1$—O—[bridged bicyclic]—N—O—Cy$^2$—$(R^{20})_p$ with $(R^{11})_n$ and $(R^{21})_r$

| Compound No. | Cy$^1$ | $(R^{10})_m$ | $(R^{11})_n$ | Cy$^2$ | $(R^{21})_r$ | $(R^{20})_p$ |
|---|---|---|---|---|---|---|
| L-1 | pyridin-2-yl | — | 5-CF$_3$ | Ph | 2-(OCH$_2{}^i$Pr) | 4-CF$_3$ |
| L-2 | pyridin-2-yl | — | 5-CF$_3$ | Ph | 2-(OCH$_2{}^c$Pr) | 4-CF$_3$ |
| L-3 | pyridin-2-yl | — | 5-CF$_3$ | Ph | 2-(CH$_2$OCH(OCH$_3$)CH$_3$) | 4-CF$_3$ |
| L-4 | pyridin-2-yl | — | 5-CF$_3$ | Ph | 2-(CO$_2{}^i$Pr) | 4-CF$_3$ |
| L-13 | pyridin-2-yl | — | 5-CF$_3$ | pyridin-2-yl | — | 5-CF$_3$ |
| L-14 | pyridazin-3-yl | — | 6-CF$_3$ | Ph | 2-(OCH$_2{}^i$Pr) | 4-CF$_3$ |
| L-15 | pyridazin-3-yl | — | 6-CF$_3$ | Ph | 2-(OCH$_2{}^c$Pr) | 4-CF$_3$ |
| L-16 | pyridazin-3-yl | — | 6-CF$_3$ | Ph | 2-(CH$_2$OCH(OCH$_3$)CH$_3$) | 4-CF$_3$ |
| L-17 | pyridazin-3-yl | — | 6-CF$_3$ | Ph | 2-(CO$_2{}^i$Pr) | 4-CF$_3$ |
| L-18 | pyridin-2-yl | — | 5-CF$_3$ | Ph | 2-(O$^n$Bu) | 4-CF$_3$ |
| L-19 | pyridin-2-yl | — | 5-CF$_3$ | Ph | 2-(OCH$_2{}^i$Pr) | 4-CF$_3$ |
| L-20 | pyridin-2-yl | — | 5-CF$_3$ | Ph | 2-(OCH$_2{}^c$Pr) | 4-CF$_3$ |
| L-21 | pyridin-2-yl | — | 5-CF$_3$ | Ph | 2-(OCH$_2$CH(OCH$_3$)CH$_3$) | 4-CF$_3$ |
| L-22 | pyridin-2-yl | — | 5-CF$_3$ | Ph | 2-(CH$_2$OCH(OCH$_3$)CH$_3$) | 4-CF$_3$ |
| L-23 | pyridin-2-yl | — | 5-CF$_3$ | Ph | 2-(CO$_2$CH(CH$_3$)CH=CH$_2$) | 4-CF$_3$ |
| L-24 | pyridin-2-yl | — | 5-CF$_3$ | Ph | 2-(O—N=C(CH$_3$)$_2$) | 4-CF$_3$ |
| L-25 | pyridin-2-yl | — | 5-CF$_3$ | Ph | 2-(NHCO$_2{}^i$Pr) | 4-CF$_3$ |
| L-26 | pyridin-2-yl | — | 5-CF$_3$ | Ph | 2-(CH=CH$_2$) | 4-CF$_3$ |
| L-27 | pyridin-2-yl | — | 5-CF$_3$ | Ph | 2-$^c$Pr | 4-CF$_3$ |
| L-28 | pyridin-2-yl | — | 5-CF$_3$ | Ph | 2-(oxazol-2-yl) | 4-CF$_3$ |
| L-29 | pyridin-2-yl | — | 5-CF$_3$ | Ph | 2-(OPh) | 4-CF$_3$ |
| L-30 | pyridin-2-yl | — | 5-CF$_3$ | Ph | 2-Ac | 4-CF$_3$ |
| L-31 | pyridin-2-yl | — | 5-CF$_3$ | Ph | 2-(C≡CSiMe$_3$) | 4-CF$_3$ |
| L-32 | pyridin-2-yl | — | 5-CF$_3$ | Ph | 2-(C≡CH) | 4-CF$_3$ |
| L-33 | pyridin-2-yl | — | 5-CF$_3$ | Ph | 2-(O[5-CF$_3$- pyridin-2-yl]) | 4-CF$_3$ |
| L-34 | pyridin-2-yl | — | 5-CF$_3$ | Ph | 2-(NHAc) | 4-CF$_3$ |
| L-35 | pyridin-2-yl | — | 5-CF$_3$ | Ph | 2-(O$^i$Pen) | 4-CF$_3$ |
| L-36 | pyridin-2-yl | — | 5-CF$_3$ | Ph | 2-(OCH$_2$CH(CH$_3$)CH$_2$CH$_3$) | 4-CF$_3$ |
| L-37 | pyridin-2-yl | — | 5-CF$_3$ | Ph | 2-(CO$_2$CH(CH$_3$)CH$_2$CH$_3$) | 4-CF$_3$ |
| L-38 | pyridin-2-yl | — | 5-CF$_3$ | Ph | 2-(OCH$_2$CH$_2$CF$_3$) | 4-CF$_3$ |
| L-39 | pyridin-2-yl | — | 5-CF$_3$ | Ph | 2-(OCH$_2$CHClCH$_3$) | 4-CF$_3$ |
| L-40 | pyridin-2-yl | — | 5-CF$_3$ | Ph | 2-(OCH$_2$CHFCH$_3$) | 4-CF$_3$ |
| L-41 | pyridin-2-yl | — | 5-CF$_3$ | Ph | 2-(CO$_2{}^i$Pr) | 4-CF$_3$ |
| L-42 | pyridin-2-yl | — | 5-CF$_3$ | Ph | 2-(CO$_2$CH$_2{}^i$Pr) | 4-CF$_3$ |
| L-43 | pyridin-2-yl | — | 5-CF$_3$ | pyrazol-5-yl | 1-(CH$_2{}^i$Pr) | 3-CF$_3$ |
| L-44 | pyridin-2-yl | — | 5-CF$_3$ | pyrazol-5-yl | 1-(CH$_2{}^c$Pr) | 3-CF$_3$ |
| L-45 | pyridin-2-yl | — | 5-CF$_3$ | pyrazol-5-yl | 1-$^n$Bu | 3-CF$_3$ |
| L-46 | pyridin-2-yl | — | 5-CF$_3$ | pyrazol-5-yl | 1-(CH$_2$OCH$_2$OCH$_3$) | 3-CF$_3$ |
| L-47 | pyridin-2-yl | — | 5-CF$_3$ | pyrazol-5-yl | 1-(CH$_2$OCH(OCH$_3$)CH$_3$) | 3-CF$_3$ |
| L-48 | pyridin-2-yl | — | 5-CF$_3$ | pyrazol-5-yl | 1-(CH(OCH$_3$)CH$_3$) | 3-CF$_3$ |
| L-49 | pyridin-2-yl | — | 5-CF$_3$ | pyrazol-5-yl | 1-(CO$_2{}^i$Pr) | 3-CF$_3$ |
| L-50 | pyridin-2-yl | — | 5-CF$_3$ | pyrazol-5-yl | 1-(CH$_2$CH(OCH$_3$)$_2$) | 3-CF$_3$ |
| L-51 | pyridin-2-yl | — | 5-CF$_3$ | pyrazol-5-yl | 1-([1,3]dioxolan-2-yl) | 3-CF$_3$ |
| L-52 | pyridin-2-yl | — | 5-CF$_3$ | pyrazol-5-yl | 1-$^n$Bu-3-CH$_3$ | — |
| L-53 | pyridin-2-yl | — | 5-CF$_3$ | pyrazol-5-yl | 1-$^n$Pr | 3-CF$_3$ |
| L-54 | pyridin-2-yl | — | 5-CF$_3$ | pyrazol-5-yl | 1-$^n$Pen | 3-CF$_3$ |
| L-55 | pyridin-2-yl | — | 5-CF$_3$ | pyrazol-5-yl | 1-$^n$Hex | 3-CF$_3$ |
| L-56 | pyridin-2-yl | — | 5-CF$_3$ | pyrazol-5-yl | 1-$^i$Pr | 3-CF$_3$ |
| L-57 | pyridin-2-yl | — | 5-CF$_3$ | pyrazol-5-yl | 1-(CH$_2$CH=CH$_2$) | 3-CF$_3$ |
| L-58 | pyridin-2-yl | — | 5-CF$_3$ | pyrazol-5-yl | 1-Bn | 3-CF$_3$ |
| L-59 | pyridin-2-yl | — | 5-CF$_3$ | pyrazol-5-yl | 1-(3,5-Cl$_2$—Ph) | 3-CF$_3$ |
| L-60 | pyridin-2-yl | — | 5-CF$_3$ | pyrazol-5-yl | 1-(pyridin-2-yl) | 3-CF$_3$ |
| L-61 | pyridin-2-yl | — | 5-CF$_3$ | pyrazol-5-yl | 1-$^n$Bu-3-(4-Cl—Ph) | — |
| L-62 | pyridin-2-yl | — | 5-CF$_3$ | pyrazol-5-yl | 1-$^n$Bu-3-(3,5-Cl$_2$—Ph) | — |
| L-63 | pyridin-2-yl | — | 5-CF$_3$ | pyrazol-5-yl | 1-(3-CF$_3$—Ph) | 3-CF$_3$ |
| L-64 | pyridin-2-yl | — | 5-CF$_3$ | pyrazol-5-yl | 1-(4-CF$_3$-thiazol-2-yl) | 3-CF$_3$ |
| L-65 | pyridin-2-yl | — | 5-CF$_3$ | pyrazol-5-yl | 1-$^n$Bu-3-(3,5-(CF$_3$)$_2$—Ph) | — |
| L-66 | pyridin-2-yl | — | 5-CF$_3$ | pyrazol-5-yl | 1-$^n$Bu-3-(3,5-F$_2$—Ph) | — |
| L-67 | pyridin-2-yl | — | 5-CF$_3$ | pyrazol-5-yl | 1-$^n$Bu-3-(3,4,5-F$_3$—Ph) | — |
| L-68 | pyridin-2-yl | — | 5-CF$_3$ | pyrazol-5-yl | 1-(CH$_2$OCH$_3$) | 3-CF$_3$ |
| L-69 | pyridin-2-yl | — | 5-CF$_3$ | pyrazol-5-yl | 1-(CH$_2$CH$_2$OCH$_3$) | 3-CF$_3$ |
| L-70 | pyridin-2-yl | — | 5-CF$_3$ | pyrazol-5-yl | 1-(CH$_2$CH(OEt)$_2$) | 3-CF$_3$ |
| L-71 | pyridin-2-yl | — | 5-CF$_3$ | pyrazol-5-yl | 1-(CH$_2$CH$_2$CH(OCH$_3$)$_2$) | 3-CF$_3$ |
| L-72 | pyridin-2-yl | — | 5-CF$_3$ | pyrazol-5-yl | 1-(CH$_2$CH$_2$CH(OEt)$_2$) | 3-CF$_3$ |
| L-73 | pyridin-2-yl | — | 5-CF$_3$ | pyrazol-5-yl | 1-(CH$_2$([1,3]dioxolan-2-yl)) | 3-CF$_3$ |
| L-74 | pyridin-2-yl | — | 5-CF$_3$ | pyrazol-5-yl | 1-(CH$_2$(tetrahydro-furan-2-yl)) | 3-CF$_3$ |
| L-75 | pyridin-2-yl | — | 5-CF$_3$ | pyrazol-5-yl | 1-(CH$_2$CH$_2$([1,3]dioxolan-2-yl)) | 3-CF$_3$ |

TABLE 11-continued (Ii)

| Compound No. | Cy¹ | (R¹⁰)$_m$ | (R¹¹)$_n$ | Cy² | (R²¹)$_r$ | (R²⁰)$_p$ |
|---|---|---|---|---|---|---|
| L-76 | pyridin-2-yl | — | 5-CF₃ | pyrazol-5-yl | 1-(CH₂CH₂([1,3]dioxan-2-yl)) | 3-CF₃ |
| L-77 | pyridin-2-yl | — | 5-CF₃ | pyrazol-5-yl | 1-Ac | 3-CF₃ |
| L-78 | pyridin-2-yl | — | 5-CF₃ | pyrazol-5-yl | 1-(CH₂CH₂CH=CH₂) | 3-CF₃ |
| L-79 | pyridin-2-yl | — | 5-CF₃ | pyrazol-5-yl | 1-(CH₂CH₂CH(Et)₂) | 3-CF₃ |
| L-80 | pyridin-2-yl | — | 5-CF₃ | pyrazol-5-yl | 1-$^i$Pen | 3-CF₃ |

TABLE 12

(Ij)

| Compound No. | Cy¹ | (R¹⁰)$_m$ | (R¹¹)$_n$ | Cy² | (R²¹)$_r$ | (R²⁰)$_p$ |
|---|---|---|---|---|---|---|
| M-1 | Ph | 2-(OCH₂$^i$Pr) | 4-CF₃ | pyridin-2-yl | — | 5-CF₃ |
| M-2 | Ph | 2-(OCH₂$^c$Pr) | 4-CF₃ | pyridin-2-yl | — | 5-CF₃ |
| M-3 | Ph | 2-(CH₂OCH(OCH₃)CH₃) | 4-CF₃ | pyridin-2-yl | — | 5-CF₃ |
| M-4 | Ph | 2-(CO₂$^i$Pr) | 4-CF₃ | pyridin-2-yl | — | 5-CF₃ |
| M-13 | Ph | 2-(OCH₂$^i$Pr) | 4-CF₃ | pyridazin-3-yl | — | 6-CF₃ |
| M-14 | Ph | 2-(OCH₂$^c$Pr) | 4-CF₃ | pyridazin-3-yl | — | 6-CF₃ |
| M-15 | Ph | 2-(CH₂OCH(OCH₃)CH₃) | 4-CF₃ | pyridazin-3-yl | — | 6-CF₃ |
| M-16 | Ph | 2-(CO₂$^i$Pr) | 4-CF₃ | pyridazin-3-yl | — | 6-CF₃ |
| M-17 | pyrazol-5-yl | 1-CH₃ | 3-CF₃ | pyridin-2-yl | — | 5-CF₃ |
| M-18 | Ph | 2-(O$^n$Bu) | 4-CF₃ | pyridin-2-yl | — | 5-CF₃ |
| M-19 | Ph | 2-(OCH₂$^i$Pr) | 4-CF₃ | pyridin-2-yl | — | 5-CF₃ |
| M-20 | Ph | 2-(OCH₂$^c$Pr) | 4-CF₃ | pyridin-2-yl | — | 5-CF₃ |
| M-21 | Ph | 2-(OCH₂CH(OCH₃)CH₃) | 4-CF₃ | pyridin-2-yl | — | 5-CF₃ |
| M-22 | Ph | 2-(CH₂OCH(OCH₃)CH₃) | 4-CF₃ | pyridin-2-yl | — | 5-CF₃ |
| M-23 | Ph | 2-(CO₂CH(CH₃)CH=CH₂) | 4-CF₃ | pyridin-2-yl | — | 5-CF₃ |
| M-24 | Ph | 2-(O—N=C(CH₃)₂) | 4-CF₃ | pyridin-2-yl | — | 5-CF₃ |
| M-25 | Ph | 2-(NHCO₂$^i$Pr) | 4-CF₃ | pyridin-2-yl | — | 5-CF₃ |
| M-26 | Ph | 2-(CH=CH₂) | 4-CF₃ | pyridin-2-yl | — | 5-CF₃ |
| M-27 | Ph | 2-$^c$Pr | 4-CF₃ | pyridin-2-yl | — | 5-CF₃ |
| M-28 | Ph | 2-(oxazol-2-yl) | 4-CF₃ | pyridin-2-yl | — | 5-CF₃ |
| M-29 | Ph | 2-(OPh) | 4-CF₃ | pyridin-2-yl | — | 5-CF₃ |
| M-30 | Ph | 2-Ac | 4-CF₃ | pyridin-2-yl | — | 5-CF₃ |
| M-31 | Ph | 2-(C≡CSiMe₃) | 4-CF₃ | pyridin-2-yl | — | 5-CF₃ |
| M-32 | Ph | 2-(C≡CH) | 4-CF₃ | pyridin-2-yl | — | 5-CF₃ |
| M-33 | Ph | 2-(O[5-CF₃-pyridin-2-yl]) | 4-CF₃ | pyridin-2-yl | — | 5-CF₃ |
| M-34 | Ph | 2-(NHAc) | 4-CF₃ | pyridin-2-yl | — | 5-CF₃ |
| M-35 | Ph | 2-(O$^i$Pen) | 4-CF₃ | pyridin-2-yl | — | 5-CF₃ |
| M-36 | Ph | 2-(OCH₂CH(CH₃)CH₂CH₃) | 4-CF₃ | pyridin-2-yl | — | 5-CF₃ |
| M-37 | Ph | 2-(CO₂CH(CH₃)CH₂CH₃) | 4-CF₃ | pyridin-2-yl | — | 5-CF₃ |
| M-38 | Ph | 2-(OCH₂CH₂CF₃) | 4-CF₃ | pyridin-2-yl | — | 5-CF₃ |
| M-39 | Ph | 2-(OCH₂CHClCH₃) | 4-CF₃ | pyridin-2-yl | — | 5-CF₃ |
| M-40 | Ph | 2-(OCH₂CHFCH₃) | 4-CF₃ | pyridin-2-yl | — | 5-CF₃ |
| M-41 | Ph | 2-(CO₂$^i$Pr) | 4-CF₃ | pyridin-2-yl | — | 5-CF₃ |
| M-42 | Ph | 2-(CO₂CH₂$^i$Pr) | 4-CF₃ | pyridin-2-yl | — | 5-CF₃ |
| M-43 | pyrazol-5-yl | 1-$^n$Bu-3-CH₃ | — | pyridin-2-yl | — | 5-CF₃ |
| M-44 | pyrazol-5-yl | 1-$^n$Pr | 3-CF₃ | pyridin-2-yl | — | 5-CF₃ |
| M-45 | pyrazol-5-yl | 1-$^n$Pen | 3-CF₃ | pyridin-2-yl | — | 5-CF₃ |
| M-46 | pyrazol-5-yl | 1-$^n$Hex | 3-CF₃ | pyridin-2-yl | — | 5-CF₃ |
| M-47 | pyrazol-5-yl | 1-$^i$Pr | 3-CF₃ | pyridin-2-yl | — | 5-CF₃ |
| M-48 | pyrazol-5-yl | 1-(CH₂CH=CH₂) | 3-CF₃ | pyridin-2-yl | — | 5-CF₃ |
| M-49 | pyrazol-5-yl | 1-Bn | 3-CF₃ | pyridin-2-yl | — | 5-CF₃ |
| M-50 | pyrazol-5-yl | 1-(3,5-Cl₂—Ph) | 3-CF₃ | pyridin-2-yl | — | 5-CF₃ |
| M-51 | pyrazol-5-yl | 1-(pyridin-2-yl) | 3-CF₃ | pyridin-2-yl | — | 5-CF₃ |
| M-52 | pyrazol-5-yl | 1-$^n$Bu-3-(4-Cl—Ph) | — | pyridin-2-yl | — | 5-CF₃ |
| M-53 | pyrazol-5-yl | 1-$^n$Bu-3-(3,5-Cl₂—Ph) | — | pyridin-2-yl | — | 5-CF₃ |
| M-54 | pyrazol-5-yl | 1-(3-CF₃—Ph) | 3-CF₃ | pyridin-2-yl | — | 5-CF₃ |
| M-55 | pyrazol-5-yl | 1-(4-CF₃-thiazol-2-yl) | 3-CF₃ | pyridin-2-yl | — | 5-CF₃ |
| M-56 | pyrazol-5-yl | 1-$^n$Bu-3-(3,5-(CF₃)₂—Ph) | — | pyridin-2-yl | — | 5-CF₃ |
| M-57 | pyrazol-5-yl | 1-$^n$Bu-3-(3,5-F₂—Ph) | — | pyridin-2-yl | — | 5-CF₃ |
| M-58 | pyrazol-5-yl | 1-$^n$Bu-3-(3,4,5-F₃—Ph) | — | pyridin-2-yl | — | 5-CF₃ |

TABLE 12-continued (Ij)

$(R^{10})_m—Cy^1—O\cdots$ [bicyclic structure with N] $—O—Cy^2—(R^{20})_p$, with $(R^{11})_n$ and $(R^{21})_r$

| Compound No. | Cy¹ | (R¹⁰)ₘ | (R¹¹)ₙ | Cy² | (R²¹)ᵣ | (R²⁰)ₚ |
|---|---|---|---|---|---|---|
| M-59 | pyrazol-5-yl | 1-(CH₂OCH₃) | 3-CF₃ | pyridin-2-yl | — | 5-CF₃ |
| M-60 | pyrazol-5-yl | 1-(CH₂CH₂OCH₃) | 3-CF₃ | pyridin-2-yl | — | 5-CF₃ |
| M-61 | pyrazol-5-yl | 1-(CH₂CH(OEt)₂) | 3-CF₃ | pyridin-2-yl | — | 5-CF₃ |
| M-62 | pyrazol-5-yl | 1-(CH₂CH₂CH(OCH₃)₂) | 3-CF₃ | pyridin-2-yl | — | 5-CF₃ |
| M-63 | pyrazol-5-yl | 1-(CH₂CH₂CH(OEt)₂) | 3-CF₃ | pyridin-2-yl | — | 5-CF₃ |
| M-64 | pyrazol-5-yl | 1-(CH₂([1,3]dioxolan-2-yl)) | 3-CF₃ | pyridin-2-yl | — | 5-CF₃ |
| M-65 | pyrazol-5-yl | 1-(CH₂(tetrahydro-furan-2-yl)) | 3-CF₃ | pyridin-2-yl | — | 5-CF₃ |
| M-66 | pyrazol-5-yl | 1-(CH₂CH₂([1,3]dioxolan-2-yl)) | 3-CF₃ | pyridin-2-yl | — | 5-CF₃ |
| M-67 | pyrazol-5-yl | 1-(CH₂CH₂([1,3]dioxan-2-yl)) | 3-CF₃ | pyridin-2-yl | — | 5-CF₃ |
| M-68 | pyrazol-5-yl | 1-Ac | 3-CF₃ | pyridin-2-yl | — | 5-CF₃ |
| M-69 | pyrazol-5-yl | 1-(CH₂CH₂CH=CH₂) | 3-CF₃ | pyridin-2-yl | — | 5-CF₃ |
| M-70 | pyrazol-5-yl | 1-(CH₂CH₂CH(Et)₂) | 3-CF₃ | pyridin-2-yl | — | 5-CF₃ |
| M-71 | pyrazol-5-yl | 1-ⁱPen | 3-CF₃ | pyridin-2-yl | — | 5-CF₃ |

Physical constants of a portion of the compounds listed in Tables (1) to (12) are shown in Table (13).

TABLE 13

| Compound No. | Physical Constant [ ] Melting Point ° C. | ¹H-NMR(CDCl₃, δ ppm) |
|---|---|---|
| 1 | [124-125] | |
| 2 | [132-133] | |
| 3 | [130-131] | |
| 8 | [116-123] | |
| 22 | [105-108] | |
| 27 | [95-98] | |
| 31 | [119-121] | |
| 38 | [139-140] | |
| 48 | [130-135] | |
| 82 | amorphous | 8.49(d, 1H), 8.12(s, 1H), 7.84(dd, 2H), 7.32(d, 1H), 7.06(d, 1H), 4.67(t, 1H), 3.81(brs, 2H), 2.51-2.46(m, 2H), 2.34-2.05(m, 6H) |
| 83 | [130-134] | |
| 84 | [130-136] | |
| 85 | [127-132] | |
| 86 | [130-132] | |
| 87 | [100-102] | |
| 88 | [134-137] | |
| 89 | [131-134] | |
| 90 | amorphous | 8.49(s, 1H), 7.87(dd, 1H), 7.75(d, 1H), 7.47(d, 1H), 7.36(d, 1H), 7.06(dd, 1H), 6.78(d, 1H), 5.77(d, 1H), 5.38(d, 1H), 4.57(t, 1H), 3.79(brs, 2H), 2.45-2.17(m, 8H) |
| 91 | [119-121] | |
| 92 | [135-140] | |
| 93 | [118-122] | |
| 94 | [143-146] | |
| 95 | amorphous | 8.48(s, 1H), 7.85(dd, 1H), 7.71(d, 1H), 7.48(dd, 1H), 7.34(d, 1H), 6.80(d, 1H), 4.60(t, 1H), 3.76(brs, 2H), 2.49-2.18(m, 8H), 0.25(s, 9H) |
| 96 | amorphous | 8.49(s, 1H), 7.87(dd, 1H), 7.74(s, 1H), 7.53(d, 1H), 7.36(d, 1H), 6.82(d, 1H), 4.59(brt, 1H), 3.78(brs, 2H), 3.34(s, 1H), 2.43-2.21(m, 8H) |
| 97 | [156-160] | |
| 98 | viscous oil | 8.68(s, 1H), 8.49(s, 1H), 7.88(dd, 1H), 7.75(brs, 1H), 7.35(d, 1H), 7.28(d, 1H), 6.81(d, 1H), 4.64(t, 1H), 3.85(brs, 2H), 2.51-2.02(m, 11H) |
| 99 | [90-93] | |
| 241 | [121-122] | |
| 242 | [92-93] | |
| 243 | [129-132] | |
| 244 | [138-140] | |
| 245 | [151-153] | |
| 246 | [121-123] | |
| 247 | [122-124] | |
| 248 | [119-121] | |
| 249 | [125-127] | |
| 251 | [165-170] | |
| 252 | [119-120] | |
| 253 | [138-140] | |
| A-2 | [148-151] | |
| A-14 | [82-84] | |
| A-18 | viscous oil | 8.48(s, 1H), 7.87(dd, 1H), 7.65(d, 1H), 7.35(d, 1H), 7.17(d, 1H), 6.96(d, 1H), 5.30-5.19(m, 1H), 4.56(t, 1H), 3.78(brs, 2H), 2.42-2.17(m, 8H), 1.37(d, 6H) |
| A-36 | [65-70] | |
| A-44 | [129-131] | |
| A-45 | [122.3-122.4] | |
| B-8 | viscous oil | 8.51(brd, 1H), 7.87(brd, 1H), 7.73(brs, 1H), 7.50(brd, 1H), 7.22(brm, 1H), 6.92(brm, 1H), 4.84-4.57(m, 4H), 3.38(brs, 3H), 3.49-3.08(brm, 4H), 2.34-1.97(brm, 4H), 1.42(brs, 3H) |
| B-25 | viscous oil | 8.50(s, 1H), 7.88(dd, 1H), 7.82(brs, 1H), 7.56(d, 1H), 6.97(brm, 1H), 6.15(brs, 1H), 4.27-4.05(brm, 5H), 3.47-1.90(brm, 6H), 1.13(brt, 3H) |
| C-23 | viscous oil | 8.50(d, 1H), 7.87(d, 1H), 7.24(brs, 1H), 6.68(brd, 1H), 5.43(brs, 1H), 5.35-5.27(m, 1H), 3.47-3.08(brm, 4H), 2.33-1.97(brm, 4H), 1.42(d, 6H) |
| E-3 | viscous oil | 8.51(s, 1H), 7.88(dd, 1H), 7.24(d, 1H), 5.77(brs, 1H), 4.43(brm, 1H), 4.09-4.02(brm, 2H), 3.48(brm, 1H), 3.27-3.24(brm, 2H), 3.06(brm, 1H), |

TABLE 13-continued

| Compound No. | Physical Constant [ ] Melting Point ° C. | $^1$H-NMR(CDCl$_3$, δ ppm) |
|---|---|---|
| E-12 | viscous oil | 2.36-2.01(brm, 4H), 1.82-1.79(brm, 2H), 1.36-1.30(brm, 2H), 0.96(brt, 3H) 8.50(s, 1H), 7.86(brs, 1H), 7.24(brm, 1H), 5.99(brs, 1H), 4.72-4.62(brm, 1H), 4.02(t, 2H), 3.46(brm, 1H), 3.26(brm, 2H), 3.03(brm, 1H), 2.34-1.92(brm, 4H), 1.87-1.77(m, 2H), 1.38-1.31(m, 2H), 0.93(t, 3H) |
| G-2 | [130-132] | |
| G-34 | viscous oil | 7.15(d, 1H), 7.06(s, 1H), 6.82(d, 1H), 4.52(brs, 1H), 4.01(brs, 2H), 3.86(d, 2H), 2.58-1.91(m, 8H), 1.32-1.26(m, 1H), 0.70-0.61(m, 2H), 0.40-0.35(m, 2H) |
| G-38 | viscous oil | 7.19-7.16(m, 3H), 7.09-7.06(d, 2H), 7.00(d, 1H), 6.85(d, 1H), 4.75(brs, 1H), 3.87(d, 2H), 3.68(brs, 2H), 2.52-2.45(m, 2H), 2.33-2.26(m, 4H), 2.17-2.07(m, 2H), 1.35-1.26(m, 1H), 0.67-0.59(m, 2H), 0.40-0.35(m, 2H) |
| G-49 | oily solid | 7.44(t, 1H), 7.15(d, 1H), 7.07(s, 1H), 7.058d, 1H), 6.87-6.79(m, 2H), 4.52(brt, 1H), 3.67(brs, 2H), 2.34-2.14(m, 8H), 1.94-1.82(m, 2H), 1.09(t, 3H) |
| G-50 | [84-87] | |
| G-54 | [120-124] | |
| G-55 | viscous oil | 7.15(d, 1H), 7.05(s, 1H), 6.81(d, 1H), 4.49(brt, 1H), 4.03(brs, 2H), 3.95(t, 2H), 3.87(d, 2H), 2.51-2.15(m, 8H), 1.84-1.74(m, 2H), 1.39-1.24(m, 3H), 0.97(t, 3H), 0.69-0.62(m, 2H), 0.40-0.35(m, 2H) |
| G-56 | amorphous | 9.08(s, 1H), 7.16(d, 1H), 7.06(s, 1H), 6.83(d, 1H), 4.56(t, 1H), 3.97(brs, 2H), 3.87(d, 2H), 2.57-2.27(m, 8H), 1.33-1.24(m, 1H), 0.70-0.61(m, 2H), 0.41-0.36(m, 2H) |
| G-57 | viscous oil | 7.15(d, 1H), 7.05(s, 1H), 6.81(d, 1H), 6.70(s, 1H), 4.57(t, 1H), 4.08(s, 3H), 4.02(brs, 2H), 3.87(d, 2H), 2.45-2.22(m, 8H), 1.35-1.24(m, 1H), 0.68-0.62(m, 2H), 0.40-0.35(m, 2H) |
| J-1 | amorphous | 8.49(s, 1H), 7.90(dd, 1H), 7.37(d, 1H), 7.16(d, H), 7.09(s, 1H), 6.98(d, 1H), 4.60(s, 1H), 3.77(d, 2H), 3.34(dd, 2H), 3.02(d, 2H), 2.55(brs, 2H), 2.19-1.91(m, 5H), 1.07(d, 6H) |
| J-2 | [50-54] | |
| J-4 | soild | 8.50(s, 1H), 7.99(d, 1H), 7.92(dd, 1H), 7.68(dd, 1H), 7.38(d, 1H), 7.10(d, 1H), 5.29-5.21(m, 1H), 4.62(s, 1H), 3.38(dd, 2H), 3.08(d, 2H), 2.60(brs, 2H), 2.11-1.94(m, 4H), 1.37(d, 6H) |
| J-6 | [107-110] | |
| J-61 | [75-77] | |
| J-62 | [126-129] | |
| J-63 | viscous oil | 8.53(d, 1H), 7.59(d, 1H), 7.50(dd, 1H), 7.18(d, 1H), 7.10(s, 1H), 6.99(d, 1H), 4.59(s, 1H), 3.89(d, 2H), 3.33(d, 2H), 2.92(d, 2H), 2.55(brs, 2H), 2.11-2.04(m, 2H), 1.95-1.91(m, 2H), 1.33-1.24(m, 1H), 0.70-0.62(m, 2H), 0.40-0.35(m, 2H) |
| J-64 | [99-101] | |
| K-4 | oil | 8.43(s, 1H), 8.20(dd, 1H), 8.02(d, 1H), 7.77(d, 1H), 7.65(d, 1H), 6.79(d, 1H), 5.33-5.20(m, 2H), 3.73(brs, 2H), 2.39-2.14(m, 8H), 1.36(t, 6H) |
| K-13 | [98-100] | |
| K-30 | | (measurement temperature: 21.5° C.) 8.49(s, 1H), 7.86(dd, 1H), 7.28(d, 1H), 5.69(s, 1H), 4.37-4.34(m, 1H), 3.80(brs, 2H), 3.73(s, 3H), 2.43-2.12(m, 8H) |
| L-4 | [65-67] | |
| L-13 | [140-141] | |
| M-1 | oil | 8.51(s, 1H), 7.91-7.85(d, d 1H), 7.40(d, 0.3H), 7.33(d, 0.7H), 7.14(d, 1H), 7.10(s, 1H), 7.03-6.99(d, d, 1H), 5.10-5.02(m, 1H), 3.80(d, 2H), 3.65(brs, 1.4H), 3.55(brs, 0.6H), 2.61-2.05(m, 6H), 1.99-1.41(m, 5H), 1.08(d, 6H) |
| M-17 | | (measurement temperature: 22.3° C.) 8.50(s, 1H), 7.88(dd, 1H), 7.41 (d, 1H), 5.78(s, 1H), 4.41-4.34(m, 1H), 3.87(brs, 2H), 3.67(s, 2H), 2.43-2.06(m, 6H), 1.87-1.74(m, 2H) |
| 100 | [104-106] | |

Next, examples of hydroxyamine compound preferable for use as production intermediates of the cyclic amine compound according to the present invention are shown in Tables (14) to (19). Furthermore, these hydroxyamine compounds are substances formed at intermediate steps of methods similar to the production methods indicated in the examples.

$(R^{10})_m$ and $(R^{11})_n$ in Tables (14) and (15) indicate respective substituents of the hydroxyamine compound represented by formula (IIIa).

$(R^{10})_m$, $(R^{11})_n$, $R^{1a}$ and $R^{3a}$ in Table (16) indicate respective substituents of the hydroxyamine compound represented by formula (IIIb).

$(R^{10})_m$, $(R^{11})_n$, $R^{1a}$ and $R^{3a}$ in Table (17) indicate respective substituents of the hydroxyamine compound represented by formula (IIIc).

$(R^{10})_m$ and $(R^{11})_n$ in Table (18) indicate respective substituents of the hydroxyamine compound represented by formula (IIId).

$(R^{10})_m$ and $(R^{11})_n$ in Table (19) indicate respective substituents of the hydroxyamine compound represented by formula (IIIe).

TABLE 14

(IIIa)

| Compound No. | $(R^{10})_m$ | $(R^{11})_n$ |
|---|---|---|
| a-1 | 2-OH | 4-CF$_3$ |
| a-2 | 2-(OEt) | 4-CF$_3$ |
| a-3 | 2-(O$^n$Pr) | 4-CF$_3$ |
| a-4 | 2-(O$^n$Bu) | 4-CF$_3$ |
| a-5 | 2-(OCH$_2$$^i$Pr) | 4-CF$_3$ |
| a-6 | 2-(O$^s$Bu) | 4-CF$_3$ |
| a-7 | 2-(O$^t$Bu) | 4-CF$_3$ |
| a-8 | 2-(O$^n$Pen) | 4-CF$_3$ |
| a-9 | 2-(O$^n$Hex) | 4-CF$_3$ |
| a-10 | 2-(OCH$_2$$^c$Pr) | 4-CF$_3$ |
| a-11 | 2-(OCH$_2$$^c$Bu) | 4-CF$_3$ |
| a-12 | 2-(OCH$_2$$^c$Pen) | 4-CF$_3$ |
| a-13 | 2-(OCH$_2$$^c$Hex) | 4-CF$_3$ |
| a-14 | 2-(OCH$_2$CH$_2$$^c$Pr) | 4-CF$_3$ |
| a-15 | 2-(OCH$_2$CH$_2$$^c$Bu) | 4-CF$_3$ |
| a-16 | 2-(CH$_2$OCH$_3$) | 4-CF$_3$ |
| a-17 | 2-(CH$_2$OC$_2$H$_5$) | 4-CF$_3$ |
| a-18 | 2-(CH(OCH$_3$)CH$_3$) | 4-CF$_3$ |
| a-19 | 2-(C$_2$H$_4$OCH$_3$) | 4-CF$_3$ |
| a-20 | 2-(CH$_2$OCH$_2$CH(CH$_3$)CH$_3$) | 4-CF$_3$ |
| a-21 | 2-(OCH$_2$OCH$_3$) | 4-CF$_3$ |
| a-22 | 2-(OCH(OCH$_3$)CH$_3$) | 4-CF$_3$ |
| a-23 | 2-(OC$_2$H$_4$OCH$_3$) | 4-CF$_3$ |

TABLE 14-continued (IIIa)

| Compound No. | $(R^{10})_m$ | $(R^{11})_n$ |
|---|---|---|
| a-24 | 2-(OCH$_2$CH(OCH$_3$)CH$_3$) | 4-CF$_3$ |
| a-25 | 2-(OCH$_2$OC$_2$H$_5$) | 4-CF$_3$ |
| a-26 | 2-(OCH(OC$_2$H$_5$)CH$_3$) | 4-CF$_3$ |
| a-27 | 2-(OC$_2$H$_4$OC$_2$H$_5$) | 4-CF$_3$ |
| a-28 | 2-(CH$_2$OCH$_2$OCH$_3$) | 4-CF$_3$ |
| a-29 | 2-(CH$_2$OCH(OCH$_3$)CH$_3$) | 4-CF$_3$ |
| a-30 | 2-(CH$_2$OC$_2$H$_4$OCH$_3$) | 4-CF$_3$ |
| a-31 | 2-(C$_2$H$_4$OCH(OCH$_3$)CH$_3$) | 4-CF$_3$ |
| a-32 | 2-(CO$_2{}^i$Pr) | 4-CF$_3$ |
| a-33 | 2-(CO$_2$CH=CH$_2$) | 4-CF$_3$ |
| a-34 | 2-(CO$_2$CH(CH$_3$)CH=CH$_2$) | 4-CF$_3$ |
| a-35 | 2-(CO$_2$CH=C(CH$_3$)CH$_3$) | 4-CF$_3$ |
| a-36 | 2-(CO$_2$C≡CH) | 4-CF$_3$ |
| a-37 | 2-(CO$_2$CH$_2$C≡CH) | 4-CF$_3$ |
| a-38 | 2-(CO$_2$C(CH$_3$)C≡CH) | 4-CF$_3$ |
| a-39 | 2-(O—N=CH$_2$) | 4-CF$_3$ |
| a-40 | 2-(O—N=CHCH$_3$) | 4-CF$_3$ |
| a-41 | 2-(O—N=C(CH$_3$)$_2$) | 4-CF$_3$ |
| a-42 | 2-(O—N=CHEt) | 4-CF$_3$ |
| a-43 | 2-(O—N=CH(CH$_3$)Et) | 4-CF$_3$ |
| a-44 | 2-(O$^i$Pen) | 4-CF$_3$ |
| a-45 | 2-(OCH$_2$CH(CH$_3$)CHCH$_3$) | 4-CF$_3$ |
| a-46 | 2-(CO$_2$CH(CH$_3$)CH$_2$CH$_3$) | 4-CF$_3$ |
| a-47 | 2-(OCH$_2$CF$_3$) | 4-CF$_3$ |
| a-48 | 2-(OCH$_2$CHF$_2$CF$_3$) | 4-CF$_3$ |
| a-49 | 2-(OCH$_2$CHClCH$_3$) | 4-CF$_3$ |
| a-50 | 2-(OCH$_2$CF$_2$CH$_3$) | 4-CF$_3$ |
| a-51 | 2-(OCH$_2$CHFCH$_3$) | 4-CF$_3$ |

TABLE 15

(IIIa)

| Compound No. | $(R^{10})_m$ | $(R^{11})_n$ |
|---|---|---|
| b-1 | 3-(OCH$_2{}^i$Pr) | 4-CF$_3$ |
| b-2 | 3-(OCH$_2{}^c$Pr) | 4-CF$_3$ |
| b-3 | 3-(O$^n$Bu) | 4-CF$_3$ |
| b-4 | 3-(O$^n$Hex) | 4-CF$_3$ |
| b-5 | 3-(CH$_2$OCH$_3$) | 4-CF$_3$ |
| b-6 | 3-(CH$_2$OCH$_2$OCH$_3$) | 4-CF$_3$ |
| b-7 | 3-(CH(OCH$_3$)CH$_3$) | 4-CF$_3$ |
| b-8 | 3-(CH$_2$OCH(OCH$_3$)CH$_3$) | 4-CF$_3$ |
| b-9 | 3-(CH$_2$OCH$_2$CH(CH$_3$)CH$_3$) | 4-CF$_3$ |
| b-10 | 3-(OCH$_2$OCH$_3$) | 4-CF$_3$ |
| b-11 | 3-(OCH(OCH$_3$)CH$_3$) | 4-CF$_3$ |
| b-12 | 3-(CO$_2{}^i$Pr) | 4-CF$_3$ |
| b-13 | 3-(CO$_2$CH=CH$_2$) | 4-CF$_3$ |
| b-14 | 3-(O—N=C(CH$_3$)$_2$) | 4-CF$_3$ |
| b-15 | 2-(OCH$_2{}^i$Pr) | 3-CF$_3$ |
| b-16 | 2-(OCH$_2{}^c$Pr) | 3-CF$_3$ |
| b-17 | 2-(O$^n$Bu) | 3-CF$_3$ |
| b-18 | 2-(O$^n$Hex) | 3-CF$_3$ |
| b-19 | 2-(CH$_2$OCH$_3$) | 3-CF$_3$ |
| b-20 | 2-(CH$_2$OCH$_2$OCH$_3$) | 3-CF$_3$ |
| b-21 | 2-(OCH(OCH$_3$)CH$_3$) | 3-CF$_3$ |
| b-22 | 2-(CH$_2$OCH(OCH$_3$)CH$_3$) | 3-CF$_3$ |
| b-23 | 2-(CH$_2$OCH$_2$CH(CH$_3$)CH$_3$) | 3-CF$_3$ |
| b-24 | 2-(OCH$_2$OCH$_3$) | 3-CF$_3$ |
| b-25 | 2-(OCH(OCH$_3$)CH$_3$) | 3-CF$_3$ |
| b-26 | 2-(CO$_2{}^i$Pr) | 3-CF$_3$ |

TABLE 15-continued (IIIa)

| Compound No. | $(R^{10})_m$ | $(R^{11})_n$ |
|---|---|---|
| b-27 | 2-(CO$_2$CH=CH$_2$) | 3-CF$_3$ |
| b-28 | 2-(O—N=C(CH$_3$)$_2$) | 3-CF$_3$ |
| b-29 | 3-(OCH$_2{}^i$Pr) | 5-CF$_3$ |
| b-30 | 3-(OCH$_2{}^c$Pr) | 5-CF$_3$ |
| b-31 | 3-(O$^n$Bu) | 5-CF$_3$ |
| b-32 | 3-(O$^n$Hex) | 5-CF$_3$ |
| b-33 | 3-(NHCH$_2{}^c$Pr) | 5-CF$_3$ |
| b-34 | 3-(N(CH$_3$)CH$_2{}^c$Pr) | 5-CF$_3$ |

TABLE 16

(IIIb)

| Compound No. | $(R^{10})_m$ | $(R^{11})_n$ | $R^{1a}$ | $R^{3a}$ |
|---|---|---|---|---|
| c-1 | 2-(OCH$_2{}^i$Pr) | 4-CF$_3$ | H | H |
| c-2 | 2-(OCH$_2{}^c$Pr) | 4-CF$_3$ | H | H |
| c-3 | 2-(O$^n$Bu) | 4-CF$_3$ | H | H |
| c-4 | 2-(O$^n$Hex) | 4-CF$_3$ | H | H |
| c-5 | 2-(CH$_2$OCH$_3$) | 4-CF$_3$ | H | H |
| c-6 | 2-(CH$_2$OCH$_2$OCH$_3$) | 4-CF$_3$ | H | H |
| c-7 | 2-(CH(OCH$_3$)CH$_3$) | 4-CF$_3$ | H | H |
| c-8 | 2-(CH$_2$OCH(OCH$_3$)CH$_3$) | 4-CF$_3$ | H | H |
| c-9 | 2-(CH$_2$OCH$_2$CH(CH$_3$)CH$_3$) | 4-CF$_3$ | H | H |
| c-10 | 2-(OCH$_2$OCH$_3$) | 4-CF$_3$ | H | H |
| c-11 | 2-(OCH(OCH$_3$)CH$_3$) | 4-CF$_3$ | H | H |
| c-12 | 2-(CO$_2{}^i$Pr) | 4-CF$_3$ | H | H |
| c-13 | 2-(CH$_2$CH(OCH$_3$)$_2$) | 4-CF$_3$ | H | H |
| c-14 | 2-([1,3]dioxolan-2-yl) | 4-CF$_3$ | H | H |
| c-15 | 2-(NH$^n$Pr) | 4-CF$_3$ | H | H |
| c-16 | 2-(NHCH$^i$Pr) | 4-CF$_3$ | H | H |
| c-17 | 2-(OCH$_2{}^i$Pr) | 4-CF$_3$ | H | CH$_3$ |
| c-18 | 2-(OCH$_2{}^c$Pr) | 4-CF$_3$ | H | CH$_3$ |
| c-19 | 2-(O$^n$Bu) | 4-CF$_3$ | H | CH$_3$ |
| c-20 | 2-(CH$_2$OCH$_2$OCH$_3$) | 4-CF$_3$ | H | CH$_3$ |
| c-21 | 2-(CH$_2$OCH(OCH$_3$)CH$_3$) | 4-CF$_3$ | H | CH$_3$ |
| c-22 | 2-(OCH(OCH$_3$)CH$_3$) | 4-CF$_3$ | H | CH$_3$ |
| c-23 | 2-(CO$_2{}^i$Pr) | 4-CF$_3$ | H | CH$_3$ |
| c-24 | 2-(CH$_2$CH(OCH$_3$)$_2$) | 4-CF$_3$ | H | CH$_3$ |
| c-25 | 2-([1,3]dioxolan-2-yl) | 4-CF$_3$ | H | CH$_3$ |
| c-26 | 2-(NH$^n$Pr) | 4-CF$_3$ | H | CH$_3$ |
| c-27 | 2-(NHCH$_2{}^i$Pr) | 4-CF$_3$ | H | CH$_3$ |
| c-28 | 2-(OCH$_2{}^i$Pr) | 4-CF$_3$ | CH$_3$ | H |
| c-29 | 2-(OCH$_2{}^c$Pr) | 4-CF$_3$ | CH$_3$ | H |
| c-30 | 2-(O$^n$Bu) | 4-CF$_3$ | CH$_3$ | H |
| c-31 | 2-(CH$_2$OCH$_2$OCH$_3$) | 4-CF$_3$ | CH$_3$ | H |
| c-32 | 2-(CH$_2$OCH(OCH$_3$)CH$_3$) | 4-CF$_3$ | CH$_3$ | H |
| c-33 | 2-(OCH(OCH$_3$)CH$_3$) | 4-CF$_3$ | CH$_3$ | H |
| c-34 | 2-(CO$_2{}^i$Pr) | 4-CF$_3$ | CH$_3$ | H |
| c-35 | 2-(CH$_2$CH(OCH$_3$)$_2$) | 4-CF$_3$ | CH$_3$ | H |
| c-36 | 2-([1,3]dioxolan-2-yl) | 4-CF$_3$ | CH$_3$ | H |
| c-37 | 2-(NH$^n$Pr) | 4-CF$_3$ | CH$_3$ | H |
| c-38 | 2-(NHCH$_2{}^i$Pr) | 4-CF$_3$ | CH$_3$ | H |
| c-39 | 2-(OCH$_2{}^i$Pr) | 3-CF$_3$ | H | H |
| c-40 | 2-(OCH$_2{}^c$Pr) | 3-CF$_3$ | H | H |
| c-41 | 2-(O$^n$Bu) | 3-CF$_3$ | H | H |
| c-42 | 2-(CH$_2$OCH$_2$OCH$_3$) | 3-CF$_3$ | H | H |
| c-43 | 2-(CH$_2$OCH(OCH$_3$)CH$_3$) | 3-CF$_3$ | H | H |
| c-44 | 2-(OCH(OCH$_3$)CH$_3$) | 3-CF$_3$ | H | H |
| c-45 | 2-(CO$_2{}^i$Pr) | 3-CF$_3$ | H | H |

TABLE 16-continued (IIIb)

| Compound No. | $(R^{10})_m$ | $(R^{11})_n$ | $R^{1a}$ | $R^{3a}$ |
|---|---|---|---|---|
| c-46 | 2-(CH$_2$CH(OCH$_3$)$_2$) | 3-CF$_3$ | H | H |
| c-47 | 2-([1,3]dioxolan-2-yl) | 3-CF$_3$ | H | H |
| c-48 | 2-(NH$^n$Pr) | 3-CF$_3$ | H | H |
| c-49 | 2-(NHCH$_2^i$Pr) | 3-CF$_3$ | H | H |
| c-50 | 2-(OCH$_2^i$Pr) | 3-CF$_3$ | H | CH$_3$ |
| c-51 | 2-(OCH$_2^c$Pr) | 3-CF$_3$ | H | CH$_3$ |
| c-52 | 2-(O$^n$Bu) | 3-CF$_3$ | H | CH$_3$ |
| c-53 | 2-(CH$_2$OCH$_2$OCH$_3$) | 3-CF$_3$ | H | CH$_3$ |
| c-54 | 2-(CH$_2$OCH(OCH$_3$)CH$_3$) | 3-CF$_3$ | H | CH$_3$ |
| c-55 | 2-(OCH(OCH$_3$)CH$_3$) | 3-CF$_3$ | H | CH$_3$ |
| c-56 | 2-(CO$_2^i$Pr) | 3-CF$_3$ | H | CH$_3$ |
| c-57 | 2-(CH$_2$CH(OCH$_3$)$_2$) | 3-CF$_3$ | H | CH$_3$ |
| c-58 | 2-([1,3]dioxolan-2-yl) | 3-CF$_3$ | H | CH$_3$ |
| c-59 | 2-(NH$^n$Pr) | 3-CF$_3$ | H | CH$_3$ |
| c-60 | 2-(NHCH$_2^i$Pr) | 3-CF$_3$ | H | CH$_3$ |
| c-61 | 3-(OCH$_2^i$Pr) | 4-CF$_3$ | H | H |
| c-62 | 3-(OCH$_2^c$Pr) | 4-CF$_3$ | H | H |
| c-63 | 3-(O$^n$Bu) | 4-CF$_3$ | H | H |
| c-64 | 3-(CH$_2$OCH$_2$OCH$_3$) | 4-CF$_3$ | H | H |
| c-65 | 3-(CH$_2$OCH(OCH$_3$)CH$_3$) | 4-CF$_3$ | H | H |
| c-66 | 3-(OCH(OCH$_3$)CH$_3$) | 4-CF$_3$ | H | H |
| c-67 | 3-(CO$_2^i$Pr) | 4-CF$_3$ | H | H |
| c-68 | 3-(CH$_2$CH(OCH$_3$)$_2$) | 4-CF$_3$ | H | H |
| c-69 | 32-([1,3]dioxolan-2-yl) | 4-CF$_3$ | H | H |
| c-70 | 3-(NH$^n$Pr) | 4-CF$_3$ | H | H |
| c-71 | 3-(NHCH$_2^i$Pr) | 4-CF$_3$ | H | H |
| c-72 | 3-(OCH$_2^i$Pr) | 4-CF$_3$ | H | CH$_3$ |
| c-73 | 3-(OCH$_2^c$Pr) | 4-CF$_3$ | H | CH$_3$ |
| c-74 | 3-(O$^n$Bu) | 4-CF$_3$ | H | CH$_3$ |
| c-75 | 3-(CH$_2$OCH$_2$OCH$_3$) | 4-CF$_3$ | H | CH$_3$ |
| c-76 | 3-(CH$_2$OCH(OCH$_3$)CH$_3$) | 4-CF$_3$ | H | CH$_3$ |
| c-77 | 3-(OCH(OCH$_3$)CH$_3$) | 4-CF$_3$ | H | CH$_3$ |
| c-78 | 3-(CO$_2^i$Pr) | 4-CF$_3$ | H | CH$_3$ |
| c-79 | 3-(CH$_2$CH(OCH$_3$)$_2$) | 4-CF$_3$ | H | CH$_3$ |
| c-80 | 3-([1,3]dioxolan-2-yl) | 4-CF$_3$ | H | CH$_3$ |
| c-81 | 3-(NH$^n$Pr) | 4-CF$_3$ | H | CH$_3$ |
| c-82 | 3-(NHCH$_2^i$Pr) | 4-CF$_3$ | H | CH$_3$ |

TABLE 17

(IIIc)

| Compound No. | $(R^{10})_m$ | $(R^{11})_n$ | $R^{1a}$ | $R^{3a}$ |
|---|---|---|---|---|
| d-1 | 1-(CH$_2^i$Pr) | 3-CF$_3$ | H | H |
| d-2 | 1-(CH$_2^c$Pr) | 3-CF$_3$ | H | H |
| d-3 | 1-$^n$Bu | 3-CF$_3$ | H | H |
| d-4 | 1-(CH$_2$OCH$_2$OCH$_3$) | 3-CF$_3$ | H | H |
| d-5 | 1-(CH$_2$OCH(OCH$_3$)CH$_3$) | 3-CF$_3$ | H | H |
| d-6 | 1-(CH(OCH$_3$)CH$_3$) | 3-CF$_3$ | H | H |
| d-7 | 1-(CO$_2^i$Pr) | 3-CF$_3$ | H | H |
| d-8 | 1-(CH$_2$CH(OCH$_3$)$_2$) | 3-CF$_3$ | H | H |
| d-9 | 1-([1,3]dioxolan-2-yl) | 3-CF$_3$ | H | H |
| d-10 | 2-(CH$_2^i$Pr) | 3-CF$_3$ | H | H |
| d-11 | 2-(CH$_2^c$Pr) | 3-CF$_3$ | H | H |
| d-12 | 2-$^n$Bu | 3-CF$_3$ | H | H |
| d-13 | 2-(CH$_2$OCH$_2$OCH$_3$) | 3-CF$_3$ | H | H |
| d-14 | 2-(CH$_2$OCH(OCH$_3$)CH$_3$) | 3-CF$_3$ | H | H |
| d-15 | 2-(CH(OCH$_3$)CH$_3$) | 3-CF$_3$ | H | H |
| d-16 | 2-(CO$_2^i$Pr) | 3-CF$_3$ | H | H |
| d-17 | 2-(CH$_2$CH(OCH$_3$)$_2$) | 3-CF$_3$ | H | H |
| d-18 | 2-([1,3]dioxolan-2-yl) | 3-CF$_3$ | H | H |
| d-19 | 1-(CH$_2^i$Pr) | 3-CF$_3$ | H | CH$_3$ |
| d-20 | 1-(CH$_2^c$Pr) | 3-CF$_3$ | H | CH$_3$ |
| d-21 | 1-$^n$Bu | 3-CF$_3$ | H | CH$_3$ |
| d-22 | 1-(CH$_2$OCH$_2$OCH$_3$) | 3-CF$_3$ | H | CH$_3$ |
| d-23 | 1-(CH$_2$OCH(OCH$_3$)CH$_3$) | 3-CF$_3$ | H | CH$_3$ |
| d-24 | 1-(CH(OCH$_3$)CH$_3$) | 3-CF$_3$ | H | CH$_3$ |
| d-25 | 1-(CO$_2^i$Pr) | 3-CF$_3$ | H | CH$_3$ |
| d-26 | 1-(CH$_2$CH(OCH$_3$)$_2$) | 3-CF$_3$ | H | CH$_3$ |
| d-27 | 1-([1,3]dioxolan-2-yl) | 3-CF$_3$ | H | CH$_3$ |
| d-28 | 2-(CH$_2^i$Pr) | 3-CF$_3$ | H | CH$_3$ |
| d-29 | 2-(CH$_2^c$Pr) | 3-CF$_3$ | H | CH$_3$ |
| d-30 | 2-$^n$Bu | 3-CF$_3$ | H | CH$_3$ |
| d-31 | 2-(CH$_2$OCH$_2$OCH$_3$) | 3-CF$_3$ | H | CH$_3$ |
| d-32 | 2-(CH$_2$OCH(OCH$_3$)CH$_3$) | 3-CF$_3$ | H | CH$_3$ |
| d-33 | 2-(CH(OCH$_3$)CH$_3$) | 3-CF$_3$ | H | CH$_3$ |
| d-34 | 2-(CO$_2^i$Pr) | 3-CF$_3$ | H | CH$_3$ |
| d-35 | 2-(CH$_2$CH(OCH$_3$)$_2$) | 3-CF$_3$ | H | CH$_3$ |
| d-36 | 2-([1,3]dioxolan-2-yl) | 3-CF$_3$ | H | CH$_3$ |
| d-37 | 1-CH$_3$ | 3-CF$_3$ | H | H |
| d-38 | 1-$^n$Bu-3-CH$_3$ | — | H | H |
| d-39 | 1-Et | 3-CF$_3$ | H | H |
| d-40 | 1-$^n$Pr | 3-CF$_3$ | H | H |
| d-41 | 1-$^n$Pen | 3-CF$_3$ | H | H |
| d-42 | 1-$^n$Hex | 3-CF$_3$ | H | H |
| d-43 | 1-$^i$Pr | 3-CF$_3$ | H | H |
| d-44 | 1-(CH$_2$CH=CH$_2$) | 3-CF$_3$ | H | H |
| d-45 | 1-Bn | 3-CF$_3$ | H | H |
| d-46 | 1-(2-Cl-Bn) | 3-CF$_3$ | H | H |
| d-47 | 1-(3-Cl—Ph) | 3-CF$_3$ | H | H |
| d-48 | 1-(3,5-Cl$_2$—Ph) | 3-CF$_3$ | H | H |
| d-49 | 1-(pyridin-2-yl) | 3-CF$_3$ | H | H |
| d-50 | 1-$^n$Bu-3-(3-Cl—Ph) | — | H | H |
| d-51 | 1-$^n$Bu-3-(4-Cl—Ph) | — | H | H |
| d-52 | 1-$^n$Bu-3-(3,4-Cl$_2$—Ph) | — | H | H |
| d-53 | 1-$^n$Bu-3-(3,5-Cl$_2$—Ph) | — | H | H |
| d-54 | 1-(3-CF$_3$—Ph) | 3-CF$_3$ | H | H |
| d-55 | 1-(3-CH$_3$—Ph) | 3-CF$_3$ | H | H |
| d-56 | 1-(pyridin-2-yl)-3-(3,4,5-F$_3$—Ph) | — | H | H |
| d-57 | 1-(pyridin-2-yl)-3-(3,5-F$_2$—Ph) | — | H | H |
| d-58 | 1-(6-CH$_3$-pyridin-2-yl) | 3-CF$_3$ | H | H |
| d-59 | 1-(4-CF$_3$-thiazol-2-yl) | 3-CF$_3$ | H | H |
| d-60 | 1-$^n$Bu-4-CH$_3$ | 3-CF$_3$ | H | H |
| d-61 | 1-$^n$Bu-3-(3,5-(CF$_3$)$_2$—Ph) | — | H | H |
| d-62 | 1-$^n$Bu-3-(3,5-F$_2$—Ph) | — | H | H |
| d-63 | 1-$^n$Bu-3-(3,4,5-F$_3$—Ph) | — | H | H |
| d-64 | 1-(C(=O)$^t$Bu) | 3-CF$_3$ | H | H |
| d-65 | 1-(pyridin-2-yl)-3-(3,5-Cl$_2$—Ph) | — | H | H |
| d-66 | 1-(CH$_2$OCH$_3$) | 3-CF$_3$ | H | H |
| d-67 | 1-(CH$_2$OEt) | 3-CF$_3$ | H | H |
| d-68 | 1-(CH$_2$CH$_2$OCH$_3$) | 3-CF$_3$ | H | H |
| d-69 | 1-(CH$_2$CH$_2$OEt) | 3-CF$_3$ | H | H |
| d-70 | 1-(CH$_2$CH(OEt)$_2$) | 3-CF$_3$ | H | H |
| d-71 | 1-(CH$_2$CH$_2$OCH(OCH$_3$)$_2$) | 3-CF$_3$ | H | H |
| d-72 | 1-(CH$_2$CH$_2$CH(OEt)$_2$) | 3-CF$_3$ | H | H |
| d-73 | 1-(CH$_2$([1,3]dioxolan-2-yl)) | 3-CF$_3$ | H | H |
| d-74 | 1-(CH$_2$(tetrahydro-furan-2-yl)) | 3-CF$_3$ | H | H |
| d-75 | 1-(CH$_2$CH$_2$([1,3]dioxolan-2-yl)) | 3-CF$_3$ | H | H |
| d-76 | 1-(CH$_2$CH$_2$([1,3]dioxan-2-yl)) | 3-CF$_3$ | H | H |
| d-77 | 1-Ac | 3-CF$_3$ | H | H |
| d-78 | 1-(C(=O)Et) | 3-CF$_3$ | H | H |
| d-79 | 1-(C(=O)$^n$Pr) | 3-CF$_3$ | H | H |
| d-80 | 1-(CH$_2$CH(OCH$_3$)$_2$)-3-(3,5-F$_2$—Ph) | — | H | H |
| d-81 | 1-(CH$_2$([1,3]dioxolan-2-yl))-3-(3,5-F$_2$—Ph) | — | H | H |
| d-82 | 1-(pyridin-2-yl)-3-(thiophen-2-yl) | — | H | H |
| d-83 | 1-(CH$_2$CH$_2$CH=CH$_2$) | 3-CF$_3$ | H | H |

TABLE 17-continued (IIIc)

| Compound No. | $(R^{10})_m$ | $(R^{11})_n$ | $R^{1a}$ | $R^{3a}$ |
|---|---|---|---|---|
| d-84 | 1-(CH$_2$CH$_2$CH(Et)$_2$) | 3-CF$_3$ | H | H |
| d-85 | 1-$^i$Pen | 3-CF$_3$ | H | H |

TABLE 18

(IIId)

| Compound No. | Cy$^1$ | $(R^{10})_m$ | $(R^{11})_n$ |
|---|---|---|---|
| e-10 | pyridin-2-yl | — | 5-CF$_3$ |
| e-11 | pyrazol-5-yl | 1-CH$_3$ | 3-CF$_3$ |
| e-12 | pyrazol-5-yl | 1-(CH$_2$$^i$Pr) | 3-CF$_3$ |
| e-13 | pyrazol-5-yl | 1-(CH$_2$$^c$Pr) | 3-CF$_3$ |
| e-14 | pyrazol-5-yl | 1-$^n$Bu | 3-CF$_3$ |
| e-15 | pyrazol-5-yl | 1-(CH$_2$OCH$_2$OCH$_3$) | 3-CF$_3$ |
| e-16 | pyrazol-5-yl | 1-(CH$_2$OCH(OCH$_3$)CH$_3$) | 3-CF$_3$ |
| e-17 | pyrazol-5-yl | 1-(CH(OCH$_3$)CH$_3$) | 3-CF$_3$ |
| e-18 | pyrazol-5-yl | 1-(CO$_2$$^i$Pr) | 3-CF$_3$ |
| e-19 | pyrazol-5-yl | 1-(CH$_2$CH(OCH$_3$)$_2$) | 3-CF$_3$ |
| e-20 | pyrazol-5-yl | 1-([1,3]dioxolan-2-yl) | 3-CF$_3$ |
| e-21 | pyrazol-5-yl | 1-$^n$Bu-3-CH$_3$ | — |
| e-22 | pyrazol-5-yl | 1-Et | 3-CF$_3$ |
| e-23 | pyrazol-5-yl | 1-$^n$Pr | 3-CF$_3$ |
| e-24 | pyrazol-5-yl | 1-$^n$Pen | 3-CF$_3$ |
| e-25 | pyrazol-5-yl | 1-$^n$Hex | 3-CF$_3$ |
| e-26 | pyrazol-5-yl | 1-$^i$Pr | 3-CF$_3$ |
| e-27 | pyrazol-5-yl | 1-(CH$_2$CH=CH$_2$) | 3-CF$_3$ |
| e-28 | pyrazol-5-yl | 1-Bn | 3-CF$_3$ |
| e-29 | pyrazol-5-yl | 1-(2-Cl—Bn) | 3-CF$_3$ |
| e-30 | pyrazol-5-yl | 1-(3-Cl—Ph) | 3-CF$_3$ |
| e-31 | pyrazol-5-yl | 1-(3,5-Cl$_2$—Ph) | 3-CF$_3$ |
| e-32 | pyrazol-5-yl | 1-(pyridin-2-yl) | 3-CF$_3$ |
| e-33 | pyrazol-5-yl | 1-$^n$Bu-3-(3-Cl—Ph) | — |
| e-34 | pyrazol-5-yl | 1-$^n$Bu-3-(4-Cl—Ph) | — |
| e-35 | pyrazol-5-yl | 1-$^n$Bu-3-(3,4-Cl$_2$—Ph) | — |
| e-36 | pyrazol-5-yl | 1-$^n$Bu-3-(3,5-Cl$_2$—Ph) | — |
| e-37 | pyrazol-5-yl | 1-(3-CF$_3$—Ph) | 3-CF$_3$ |
| e-38 | pyrazol-5-yl | 1-(3-CH$_3$—Ph) | 3-CF$_3$ |
| e-39 | pyrazol-5-yl | 1-(Py-2-yl)-3-(3,4,5-F$_3$—Ph) | — |
| e-40 | pyrazol-5-yl | 1-(Py-2-yl)-3-(3,5-F$_2$—Ph) | — |
| e-41 | pyrazol-5-yl | 1-(6-CH$_3$-pyridin-2-yl) | 3-CF$_3$ |
| e-42 | pyrazol-5-yl | 1-(4-CF$_3$-thiazol-2-yl) | 3-CF$_3$ |
| e-43 | pyrazol-5-yl | 1-$^n$Bu-4-CH$_3$ | 3-CF$_3$ |
| e-44 | pyrazol-5-yl | 1-$^n$Bu-3-(3,5-(CF$_3$)$_2$—Ph) | — |
| e-45 | pyrazol-5-yl | 1-$^n$Bu-3-(3,5-F$_2$—Ph) | — |
| e-46 | pyrazol-5-yl | 1-$^n$Bu-3-(3,4,5-F$_3$—Ph) | — |
| e-47 | pyrazol-5-yl | 1-(C(=O)$^t$Bu) | 3-CF$_3$ |
| e-48 | pyrazol-5-yl | 1-(pyridin-2-yl)-3-(3,5-Cl$_2$—Ph) | — |
| e-49 | pyrazol-5-yl | 1-(CH$_2$OCH$_3$) | 3-CF$_3$ |
| e-50 | pyrazol-5-yl | 1-(CH$_2$OEt) | 3-CF$_3$ |
| e-51 | pyrazol-5-yl | 1-(CH$_2$CH$_2$OCH$_3$) | 3-CF$_3$ |
| e-52 | pyrazol-5-yl | 1-(CH$_2$CH$_2$OEt) | 3-CF$_3$ |
| e-53 | pyrazol-5-yl | 1-(CH$_2$CH(OEt)$_2$) | 3-CF$_3$ |
| e-54 | pyrazol-5-yl | 1-(CH$_2$CH$_2$CH(OCH$_3$)$_2$) | 3-CF$_3$ |
| e-55 | pyrazol-5-yl | 1-(CH$_2$CH$_2$CH(OEt)$_2$) | 3-CF$_3$ |
| e-56 | pyrazol-5-yl | 1-(CH$_2$([1,3]dioxolan-2-yl)) | 3-CF$_3$ |
| e-57 | pyrazol-5-yl | 1-(CH$_2$(tetrahydro-furan-2-yl)) | 3-CF$_3$ |
| e-58 | pyrazol-5-yl | 1-(CH$_2$CH$_2$([1,3]dioxolan-2-yl)) | 3-CF$_3$ |
| e-59 | pyrazol-5-yl | 1-(CH$_2$CH$_2$([1,3]dioxan-2-yl)) | 3-CF$_3$ |
| e-60 | pyrazol-5-yl | 1-Ac | 3-CF$_3$ |
| e-61 | pyrazol-5-yl | 1-(C(=O)Et) | 3-CF$_3$ |
| e-62 | pyrazol-5-yl | 1-(C(=O)$^n$Pr) | 3-CF$_3$ |
| e-63 | pyrazol-5-yl | 1-(CH$_2$CH(OCH$_3$)$_2$)-3-(3,5-F$_2$—Ph) | — |
| e-64 | pyrazol-5-yl | 1-(CH$_2$([1,3]dioxolan-2-yl))-3-(3,5-F$_2$—Ph) | — |
| e-65 | pyrazol-5-yl | 1-(pyridin-2-yl)-3-(thiophen-2-yl) | — |
| e-66 | pyrazol-5-yl | 1-(CH$_2$CH$_2$CH=CH$_2$) | 3-CF$_3$ |
| e-67 | pyrazol-5-yl | 1-(CH$_2$CH$_2$CH(Et)$_2$) | 3-CF$_3$ |
| e-68 | pyrazol-5-yl | 1-$^i$Pen | 3-CF$_3$ |

TABLE 19

(IIIe)

| Compound No. | $(R^{10})_m$ | $(R^{11})_n$ |
|---|---|---|
| f-1 | 2-(OCH$_2$$^i$Pr) | 4-CF$_3$ |
| f-2 | 2-(OCH$_2$$^c$Pr) | 4-CF$_3$ |
| f-3 | 2-(CH$_2$OCH(OCH$_3$)CH$_3$) | 4-CF$_3$ |
| f-4 | 2-(CO$_2$$^i$Pr) | 4-CF$_3$ |
| f-5 | 2-(OEt) | 4-CF$_3$ |
| f-6 | 2-(O$^n$Pr) | 4-CF$_3$ |
| f-7 | 2-(O$^n$Bu) | 4-CF$_3$ |
| f-8 | 2-(O$^s$Bu) | 4-CF$_3$ |
| f-9 | 2-(O$^i$Bu) | 4-CF$_3$ |
| f-10 | 2-(O$^n$Pen) | 4-CF$_3$ |
| f-11 | 2-(O$^n$Hex) | 4-CF$_3$ |
| f-12 | 2-(OCH$_2$$^c$Bu) | 4-CF$_3$ |
| f-13 | 2-(OCH$_2$$^c$Pen) | 4-CF$_3$ |
| f-14 | 2-(OCH$_2$$^c$Hex) | 4-CF$_3$ |
| f-15 | 2-(OCH$_2$CH$_2$$^c$Pr) | 4-CF$_3$ |
| f-16 | 2-(OCH$_2$CH$_2$$^c$Bu) | 4-CF$_3$ |
| f-17 | 2-(CH$_2$OCH$_3$) | 4-CF$_3$ |
| f-18 | 2-(CH$_2$OC$_2$H$_5$) | 4-CF$_3$ |
| f-19 | 2-(CH(OCH$_3$)CH$_3$) | 4-CF$_3$ |
| f-20 | 2-(C$_2$H$_4$OCH$_3$) | 4-CF$_3$ |
| f-21 | 2-(CH$_2$OCH$_2$CH(CH$_3$)CH$_3$) | 4-CF$_3$ |
| f-22 | 2-(OCH$_2$OCH$_3$) | 4-CF$_3$ |
| f-23 | 2-(OCH(OCH$_3$)CH$_3$) | 4-CF$_3$ |
| f-24 | 2-(OC$_2$H$_4$OCH$_3$) | 4-CF$_3$ |
| f-25 | 2-(OCH$_2$CH(OCH$_3$)CH$_3$) | 4-CF$_3$ |
| f-26 | 2-(OCH$_2$OC$_2$H$_5$) | 4-CF$_3$ |
| f-27 | 2-(OCH(OC$_2$H$_5$)CH$_3$) | 4-CF$_3$ |
| f-28 | 2-(OC$_2$H$_4$OC$_2$H$_5$) | 4-CF$_3$ |
| f-29 | 2-(CH$_2$OCH$_2$OCH$_3$) | 4-CF$_3$ |
| f-30 | 2-(CH$_2$OC$_2$H$_4$OCH$_3$) | 4-CF$_3$ |
| f-31 | 2-(C$_2$H$_4$OCH(OCH$_3$)CH$_3$) | 4-CF$_3$ |
| f-32 | 2-(CO$_2$CH=CH$_2$) | 4-CF$_3$ |
| f-33 | 2-(CO$_2$CH=C(CH$_3$)CH$_3$) | 4-CF$_3$ |
| f-34 | 2-(CO$_2$CH=C(CH$_3$)CH$_3$) | 4-CF$_3$ |
| f-35 | 2-(CO$_2$C≡CH) | 4-CF$_3$ |
| f-36 | 2-(CO$_2$C$_2$≡CH) | 4-CF$_3$ |
| f-37 | 2-(CO$_2$C(CH$_3$)C≡CH) | 4-CF$_3$ |
| f-38 | 2-(O—N=CH$_2$) | 4-CF$_3$ |
| f-39 | 2-(O—N=CHCH$_3$) | 4-CF$_3$ |
| f-40 | 2-(O—N=C(CH$_3$)$_2$) | 4-CF$_3$ |
| f-41 | 2-(O—N=CHEt) | 4-CF$_3$ |
| f-42 | 2-(O—N=CH(CH$_3$)Et) | 4-CF$_3$ |
| f-43 | 2-(O$^i$Pen) | 4-CF$_3$ |
| f-44 | 2-(OCH$_2$CH(CH$_3$)CH$_2$CH$_3$) | 4-CF$_3$ |
| f-45 | 2-(CO$_2$CH(CH$_3$)CH$_2$CH$_3$) | 4-CF$_3$ |

TABLE 19-continued $$(\text{R}^{10})_m \overset{2}{\underset{(\text{R}^{11})_n}{\diagup}} \diagdown O \diagdown \diagdown N-OH \quad (\text{IIIe})$$

| Compound No. | $(\text{R}^{10})_m$ | $(\text{R}^{11})_n$ |
|---|---|---|
| f-46 | 2-(OCH$_2$CF$_3$) | 4-CF$_3$ |
| f-47 | 2-(OCH$_2$CH$_2$CF$_3$) | 4-CF$_3$ |
| f-48 | 2-(OCH$_2$CHClCH$_3$) | 4-CF$_3$ |
| f-49 | 2-(OCH$_2$CF$_2$CH$_3$) | 4-CF$_3$ |
| f-50 | 2-(OCH$_2$CHFCH$_3$) | 4-CF$_3$ |

Physical constants of a portion of the compounds listed in Tables (14) to (19) are shown in Table (20).

TABLE 20

| Compound No. | Physical Constant [ ] Melting Point ° C. | $^1$H-NMR(CCDCl$_3$, ppm) |
|---|---|---|
| a-10 | solid | 7.13(d, 1H), 7.04(s, 1H), 6.78(d, 1H), 4.44(br, 1H), 3.85(d, 2H), 3.56(brs, 2H), 2.26-2.22(m, 2H), 2.14-2.12(m, 6H), 1.34-1.26(m, 1H), 0.68-0.59(m, 2H), 0.37(q, 2H) |
| e-10 | [134-136] | |

Although the following indicates a few preparation examples of the acaricide of the present invention, additives and addition rates thereof are not limited to those indicated in the examples, but rather can be varied over a wide range. The term "parts" in the preparation examples indicates "parts by weight".

Preparation Example 1

Water-Dispersible Powder

| | |
|---|---|
| Compound of present invention | 40 parts |
| Diatomaceous earth | 53 parts |
| Higher alcohol sulfate ester | 4 parts |
| Alkylnaphthalene sulfonate | 3 parts |

The ingredients were mixed and finely crushed to obtain a water-dispersible powder containing 40% active ingredient.

Preparation Example 2

Emulsion

| | |
|---|---|
| Compound of present invention | 30 parts |
| Xylene | 33 parts |
| Dimethylformamide | 30 parts |
| Polyoxyethylene alkyl aryl ether | 7 parts |

The ingredients were mixed and dissolved to obtain an emulsion containing 30% active ingredient.

The following indicates that the cyclic amine compound or salt thereof of the present invention is useful as an active ingredient of an acaricide using the test examples indicated below.

Test Example 1

Efficacy Test Against *Tetranychus urticae*

Seventeen organic phosphorous-resistant adult female *Tetranychus urticae* mites were inoculated onto the first leaves of a kidney bean plant planted in a No. 3 pot 7 to 10 days after germination. Next, an emulsion was prepared having the formula indicated in the aforementioned Preparation Example 2. This emulsion was diluted with water to a compound concentration of 125 ppm, 31 ppm or 8 ppm after which the diluted liquids were sprayed onto the kidney bean plant. The kidney bean plant was then placed in a constant temperature room at a temperature of 25° C. and humidity of 65%. The adult insect mortality rates were investigated 3 days after spraying. The test was repeated twice.

The aforementioned test was carried out on emulsions respectively containing the cyclic amine compounds of Compound No. 1, 2, 27, 31, 88, 91, 92, 100, 243, 244, 245, 247, 249, 252, 253, A-14, A-44, E-12, G-2, G-34, G-49, G-50, G-55, G-57, J-2, J-6, J-63, J-64, K-4, K-13 and M-1. As a result, the insect mortality rates for all of the compounds in the case of diluting to a concentration of 125 ppm were 80% or higher.

The aforementioned test was also carried out on emulsions respectively containing the cyclic amine compounds of Compound No. 22, 48, 242, 246, 248, J-1 and J-4. As a result, the insect mortality rates for all of these compounds in the case of diluting to a concentration of 31 ppm were also 80% or higher.

The aforementioned test was also carried out on emulsions respectively containing the cyclic amine compounds of Compound No. 3, 8 and 38. As a result, the insect mortality rates for all of these compounds in the case of diluting to a concentration of 8 ppm were also 80% or higher.

Test Example 2

Efficacy Test Against *Panonychus citri*

Ten acaricide-resistant adult female *Panonychus citri* mites were inoculated onto mandarin orange leaf placed in a Petri dish. Next, an emulsion was prepared having the formula indicated in the aforementioned Preparation Example 2. This emulsion was diluted with water to a compound concentration of 125 ppm or 31 ppm after which the diluted liquids were sprayed onto the mandarin orange leaf with a rotary spraying tower. The mandarin orange leaf was then placed in a constant temperature room at a temperature of 25° C. and humidity of 65%. The adult insect mortality rates were investigated 3 days after spraying.

The aforementioned test was carried out on emulsions respectively containing the cyclic amine compounds of Compound No. 27, 249, 252, A-14, E-12, G-34, G-49, G-50, G-57, J-1, J-2, J-63, K-4 and K-13. As a result, the insect mortality rates for all of the compounds in the case of diluting to a concentration of 125 ppm were 80% or higher.

The aforementioned test was also carried out on emulsions respectively containing the cyclic amine compounds of Compound No. 3, 8, 22, 31, 38, 100, 242, 243, 246, 247 and 248.

As a result, the insect mortality rates for all of these compounds in the case of diluting to a concentration of 31 ppm were also 80% or higher.

On the basis of the above results, the cyclic amine compound of the present invention or salt thereof was determined to demonstrate superior acaricidal action against acari.

INDUSTRIAL APPLICABILITY

The cyclic amine compound or salt thereof of the present invention is able to effectively control acari and the like harmful to agricultural crops and in terms of hygiene. In addition, use of the hydroxyamine compound or salt thereof according to the present invention makes it possible to easily synthesize the cyclic amine compound or salt thereof according to the present invention.

The invention claimed is:

1. A cyclic amine compound represented by formula (I), or a salt thereof:

[Chemical Formula 1]

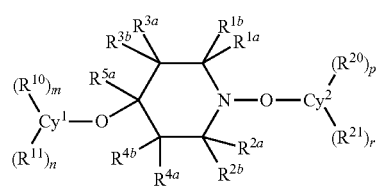

wherein, in formula (I), $Cy^1$ and $Cy^2$ respectively and independently represent a C6-10 aryl group or heterocyclic group, $R^{1a}$ and $R^{2a}$ together form a C1-2 alkylene group, and $R^{1b}$, $R^{2b}$, $R^{3a}$, $R^{3b}$, $R^{4a}$, $R^{4b}$ and $R^{5a}$ respectively and independently represent a hydrogen atom or $R^{3a}$ and $R^{4a}$ together form a C1-2 alkylene group, and $R^{1a}$, $R^{1b}$, $R^{2a}$, $R^{2b}$, $R^{3b}$, $R^{4b}$ and $R^{5a}$ respectively and independently represent a hydrogen atom, $R^{10}$, $R^{11}$, $R^{20}$ and $R^{21}$ respectively and independently represent an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxyl group, oxo group, unsubstituted or substituted C1-6 alkoxy group, unsubstituted or substituted C3-8 cycloalkoxy group, unsubstituted or substituted C2-6 alkenyloxy group, unsubstituted or substituted C2-6 alkynyloxy group, carboxyl group, unsubstituted or substituted C1-7 acyl group, unsubstituted or substituted C1-6 alkoxycarbonyl group, unsubstituted or substituted C2-6 alkenyloxycarbonyl group, unsubstituted or substituted C2-6 alkynyloxycarbonyl group, unsubstituted or substituted C1-7 acyloxy group, unsubstituted or substituted C1-6 alkylideneaminooxy group, unsubstituted or substituted C6-10 aryl group, unsubstituted or substituted heterocyclic group, unsubstituted or substituted C6-10 aryloxy group, unsubstituted or substituted heterocyclyloxy group, amino group, unsubstituted or substituted C1-6 alkylamino group, unsubstituted or substituted C6-10 arylamino group, unsubstituted or substituted heterocyclylamino group, unsubstituted or substituted C1-7 acylamino group, unsubstituted or substituted C1-6 alkoxycarbonylamino group, unsubstituted or substituted aminocarbonyl group, unsubstituted or substituted ureido group, mercapto group, unsubstituted or substituted C1-6 alkylthio group, unsubstituted or substituted C6-10 arylthio group, unsubstituted or substituted heterocyclylthio group, (unsubstituted or substituted C1-6 alkyl)thiocarbonyl group, (unsubstituted or substituted C1-6 alkoxy)thiocarbonyl group, (unsubstituted or substituted C1-6 alkylthio)carbonyl group, (unsubstituted or substituted C1-6 alkylthio)thiocarbonyl group, tri-C1-6 alkyl-substituted silyl group, tri-C6-10 aryl-substituted silyl group, cyano group, nitro group or halogen atom, $R^{10}$ or $R^{11}$ on $Cy^1$ may respectively or mutually, or together with an atom that bonds on $Cy^1$, form a ring, and $R^{20}$ or $R^{21}$ on $Cy^2$ may respectively or mutually, or with an atom that bonds on $Cy^2$, form a ring, m represents the number of $R^{10}$ and is an integer of 0 to 5, and when m is 2 or more, $R^{10}$ may be mutually the same or different, n represents the number of $R^{11}$ and is an integer of 0 to 5, and when n is 2 or more, $R^{11}$ may be mutually the same or different, p represents the number of $R^{20}$ and is an integer of 0 to 5, and when p is 2 or more, $R^{20}$ may be mutually the same or different, and r represents the number of $R^{21}$ and is an integer of 0 to 5, and when r is 2 or more, $R^{21}$ may be mutually the same or different].

2. The cyclic amine compound or salt thereof according to claim 1, wherein $Cy^1$ in formula (I) represents a phenyl group, pyrazolyl group, thiadiazolyl group, pyridyl group, pyrimidinyl group or pyridazinyl group, and $Cy^2$ represents a phenyl group, pyrazolyl group, thiadiazolyl group, pyridyl group, pyrimidinyl group or pyridazinyl group.

3. The cyclic amine compound or salt thereof according to claim 1, wherein in formula (I), $R^{10}$ represents a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group, $R^{11}$ represents a cyano group, halogen atom, C1-6 haloalkyl group, C2-6 haloalkenyl group or C2-6 haloalkynyl group, $R^{20}$ represents a cyano group, halogen atom, C1-6 haloalkyl group, C2-6 haloalkenyl group or C2-6 haloalkynyl group, and $R^{21}$ represents a C1-6 alkyl group, C1-6 alkoxy C1-6 alkyl group, C1-6 alkoxy C1-6 alkoxy C1-6 alkyl group, C3-8 cycloalkyl group, C2-6 alkenyl group, C2-6 alkynyl group, hydroxyl group, C1-6 alkoxy group, C1-6 haloalkoxy group, C2-6 haloalkenyloxy group, C2-6 haloalkynyloxy group, C1-6 alkoxy C1-6 alkoxy group, C3-8 cycloalkyl C1-6 alkoxy group, C1-7 acyl group, C1-6 alkoxycarbonyl group, C2-6 alkenyloxycarbonyl group, C2-6 alkynyloxycarbonyl group, C1-6 alkylideneaminooxy group, heterocyclic group, C6-10 aryloxy group, heterocyclyloxy group, C1-7 acylamino group, C1-6 alkoxycarbonylamino group, 3-(C1-6 alkyl)ureido group, unsubstituted or substituted C7-11 aralkyl group, unsubstituted or substituted C7-11 aralkyloxy group or nitro group.

4. The cyclic amine compound or salt thereof according to claim 1 wherein, the formula (I) is formula (II):

[Chemical Formula 2]

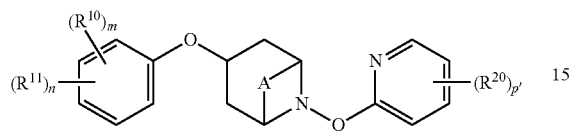

(II)

(wherein, in formula (II), $R^{10}$, m, $R^{11}$, n and $R^{20}$ are same as previously defined in formula (I), A represents a C1-2 alkylene group, and p' represents the number of $R^{20}$ and is an integer of any of 0 to 4, and when p' is 2 or more, $R^{20}$ may be mutually the same or different).

5. A process of producing an acaricidal effect using an effective amount of at least one compound selected from the cyclic amine compound or salt thereof according to claim 1.

* * * * *